(12) United States Patent
Merutka

(10) Patent No.: US 9,315,545 B2
(45) Date of Patent: Apr. 19, 2016

(54) HEPCIDIN MIMETIC PEPTIDES AND USES THEREOF

(71) Applicant: MERGANSER BIOTECH, INC., Newtown Square, PA (US)

(72) Inventor: Gene Scott Merutka, Phoenixville, PA (US)

(73) Assignee: MERGANSER BIOTECH, INC., King of Prussia, PA (US)

( * ) Notice: Subject to any disclaimer, the term of this patent is extended or adjusted under 35 U.S.C. 154(b) by 0 days.

(21) Appl. No.: 14/680,562

(22) Filed: Apr. 7, 2015

(65) Prior Publication Data

US 2015/0284429 A1    Oct. 8, 2015

Related U.S. Application Data

(60) Provisional application No. 61/976,489, filed on Apr. 7, 2014, provisional application No. 62/085,817, filed on Dec. 1, 2014.

(51) Int. Cl.
*C07K 7/06* (2006.01)
*C07K 7/02* (2006.01)

(52) U.S. Cl.
CPC .... *C07K 7/06* (2013.01); *C07K 7/02* (2013.01)

(58) Field of Classification Search
None
See application file for complete search history.

(56) References Cited

U.S. PATENT DOCUMENTS

| | | | |
|---|---|---|---|
| 6,194,395 B1 * | 2/2001 | Schultz | A61K 9/0014 514/45 |
| 8,435,941 B2 | 5/2013 | Ganz et al. | |
| 2005/0158301 A1 * | 7/2005 | Carney | C12Y 304/21005 424/94.64 |
| 2007/0134746 A1 | 6/2007 | Kulaksiz | |
| 2008/0020978 A1 * | 1/2008 | Gegg, Jr. | C07K 14/57527 424/1.69 |
| 2008/0213277 A1 | 9/2008 | Sasu et al. | |
| 2010/0330595 A1 | 12/2010 | Kulaksiz | |
| 2011/0183362 A1 | 7/2011 | Lauth et al. | |
| 2011/0287448 A1 | 11/2011 | Kulaksiz | |
| 2012/0040894 A1 | 2/2012 | Ganz et al. | |
| 2013/0203662 A1 | 8/2013 | Ganz et al. | |
| 2014/0271690 A1 * | 9/2014 | Wang | C07K 14/4711 424/185.1 |

FOREIGN PATENT DOCUMENTS

| | | |
|---|---|---|
| WO | 2004058044 | 7/2004 |
| WO | 2010065815 | 6/2010 |
| WO | 2013086143 | 6/2013 |
| WO | 2014/145561 A2 | 9/2014 |

OTHER PUBLICATIONS

Janecka et al ('Structural studies of position 2 modified endomorphin-2 analogs by NMR spectroscopy and molecular modeling' Polish Journal of Chemistry v83(7) 2009, abstract only 1 page).*
Hunter et al., The solution of human hepcidin, a peptide hormone with antimicrobial activity that is involved in iron uptake and hereditary hemochromatosis, Journal of Biological Chemistry, Oct. 4, 2002, 37597-37603, vol. 227.
Cartens, The Analysis of the Interaction between Hepcidin and Ferroportin, Thesis—University of Troms, May 20, 2009, 58pp.
Bracher et al., The relative rates of thiol-thioester exchange and hydrolysis for alkyl and aryl thioalkanoates in water, Oring Life Evol Biosph 2011 41:399-412.
Burgess, Designing amino acids to determine the local conformations of peptides, PNAS USA 1994 91:2649-2653.
Malesevic et al., Spectroscopic detection of pseudo-turns in homodetic cyclic penta- and hexapeptides comprising beta-homoproline, International Journal of Peptide Research and Therapeutics 2006 12(2):165-177. (Abstract Only).
Nemeth et al., The N-terminus of hepcidin is essential for its interaction with ferroportin: structure-function study, Blood 2006 107(1):328-333.
Pegoraro and Moroder, Synthesis of lipopeptides, vol. E 22, Chapter 6.4, p. 333-374, published in 2004.
Preza et al., Minihepcidens are rationally designed small peptides that mimic hepcidin activity in mice and may be useful for the treatment of iron overload, Journal of Clinical Investigation 2011 121(12):4880-4888.
Singh and Whitesides, Thiol-disulfide interchange, Supplement S: The chemistry of sulphur-containing functional groups, John Wiley & Sons Ltd, 1993.
Rijkers et al., A convenient solid phase synthesis of S-palmitoyl transmembrane peptides, Tetrahedron Letters 2005 46:3341-3345.
Yousefi-Salakdeg et al., A method of S- and O-palmitoylation of peptides: synthesis of pulmonary surfactant protein-C models, Biochem. J. 1999 343:557-562.
Betts and Russell, Amino Acid Properties and Consequences of Substitutions, Bioinformatics for Geneticists, Chapter 14, John Wiley & Sons Ltd. 2003.
Clark et al., Understanding the structure/activity relationships of the iron regulatory peptide hepcidin, Chem Biol. 2001 18(3):336-343.
Preza et al., Cellular catabolism of the iron-regulatory peptide hormone hepcidin, PLOS One 2013 8(3):e58934.
Ramos et al., Minihepcidins prevent iron overlaod in a hepcidin-deficient mouse model of severe hemochromatosis, Blood 2012 120(18):3829-3836.
Fernandes et al., The molecular basis of hepcidin-resistant hereditary hemochromatosis, Blood 2009 114(2):437-443.
Clark et al., Design, synthesis and characterization of cyclic analogues of the iron regulatory peptide hormone hepcidin, Peptide Science 2013 100(5):519-526.
Fung et al., Thiol-derivatized minihepcidins retain biological activity, Bioorganic & Medicinal Chem. Lett. 2015 25:763-766.

* cited by examiner

*Primary Examiner* — Christina Bradley
*Assistant Examiner* — Ronald Niebauer
(74) *Attorney, Agent, or Firm* — Pepper Hamilton LLP

(57) ABSTRACT

Compounds and methods are described herein that can be used to treat subjects for conditions related to hepcidin activity, such as but not limited diseases of iron metabolism, beta thalassemia, hemochromatosis, iron-loading anemias, alcoholic liver disease, or chronic hepatitis C.

13 Claims, 8 Drawing Sheets

SEQUENCE LISTING

```
<160> NUMBER OF SEQ ID NOS: 11

<210> SEQ ID NO 1
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Iminodiacetic acid
<220> FEATURE:
<221> NAME/KEY: MISC_FEATURE
<222> LOCATION: (4)..(4)
<223> OTHER INFORMATION: DPa
<220> FEATURE:
<221> NAME/KEY: MISC_FEATURE
<222> LOCATION: (5)..(5)
<223> OTHER INFORMATION: beta-homoproline
<220> FEATURE:
```

```
<221> NAME/KEY: MISC_FEATURE
<222> LOCATION: (10)..(10)
<223> OTHER INFORMATION: Ahx-Ida(NH-PAL)-NH2

<400> SEQUENCE: 1

Xaa Thr His Xaa Xaa Arg Cys Arg Trp Xaa
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Iminodiacetic acid
<220> FEATURE:
<221> NAME/KEY: MISC_FEATURE
<222> LOCATION: (4)..(4)
<223> OTHER INFORMATION: Dpa
<220> FEATURE:
<221> NAME/KEY: MISC_FEATURE
<222> LOCATION: (5)..(5)
<223> OTHER INFORMATION: beta-homoproline
<220> FEATURE:
<221> NAME/KEY: MOD_RES
<222> LOCATION: (7)..(7)
<223> OTHER INFORMATION: Cys-S-CH3
<220> FEATURE:
<221> NAME/KEY: MISC_FEATURE
<222> LOCATION: (10)..(10)
<223> OTHER INFORMATION: Ahx-Ida(NH-PAL)-NH2

<400> SEQUENCE: 2

Xaa Thr His Xaa Xaa Arg Cys Arg Trp Xaa
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Iminodiacetic acid
<220> FEATURE:
<221> NAME/KEY: MISC_FEATURE
<222> LOCATION: (4)..(4)
<223> OTHER INFORMATION: Dpa
<220> FEATURE:
<221> NAME/KEY: MISC_FEATURE
<222> LOCATION: (5)..(5)
<223> OTHER INFORMATION: beta-homoproline
<220> FEATURE:
<221> NAME/KEY: MOD_RES
<222> LOCATION: (7)..(7)
<223> OTHER INFORMATION: Cys-C(=O)CH3
<220> FEATURE:
```

```
<221> NAME/KEY: MISC_FEATURE
<222> LOCATION: (10)..(10)
<223> OTHER INFORMATION: Ahx-Ida(NH-PAL)-NH2

<400> SEQUENCE: 3

Xaa Thr His Xaa Xaa Arg Cys Arg Trp Xaa
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Iminodiacetic acid
<220> FEATURE:
<221> NAME/KEY: MISC_FEATURE
<222> LOCATION: (4)..(4)
<223> OTHER INFORMATION: Dpa
<220> FEATURE:
<221> NAME/KEY: MISC_FEATURE
<222> LOCATION: (5)..(5)
<223> OTHER INFORMATION: beta-homoproline
<220> FEATURE:
<221> NAME/KEY: MOD_RES
<222> LOCATION: (7)..(7)
<223> OTHER INFORMATION: Cys-CH2-CH3
<220> FEATURE:
<221> NAME/KEY: MISC_FEATURE
<222> LOCATION: (10)..(10)
<223> OTHER INFORMATION: Ahx-Ida(NH-PAL)-NH2

<400> SEQUENCE: 4

Xaa Thr His Xaa Xaa Arg Cys Arg Trp Xaa
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Iminodiacetic acid
<220> FEATURE:
<221> NAME/KEY: MISC_FEATURE
<222> LOCATION: (4)..(4)
<223> OTHER INFORMATION: Dpa
<220> FEATURE:
<221> NAME/KEY: MISC_FEATURE
<222> LOCATION: (5)..(5)
<223> OTHER INFORMATION: L-nipecotic acid
<220> FEATURE:
<221> NAME/KEY: MOD_RES
<222> LOCATION: (7)..(7)
<223> OTHER INFORMATION: Cys-S-CH3
<220> FEATURE:
<221> NAME/KEY: MISC_FEATURE
<222> LOCATION: (10)..(10)
```

<223> OTHER INFORMATION: Ahx-Ida(NH-PAL)-NH2

<400> SEQUENCE: 5

Xaa Thr His Xaa Xaa Arg Cys Arg Trp Xaa
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Iminodiacetic acid
<220> FEATURE:
<221> NAME/KEY: MISC_FEATURE
<222> LOCATION: (4)..(4)
<223> OTHER INFORMATION: Dpa
<220> FEATURE:
<221> NAME/KEY: MISC_FEATURE
<222> LOCATION: (5)..(5)
<223> OTHER INFORMATION: L-nipecotic acid
<220> FEATURE:
<221> NAME/KEY: MISC_FEATURE
<222> LOCATION: (10)..(10)
<223> OTHER INFORMATION: Ahx-Ida(NH-PAL)-NH2

<400> SEQUENCE: 6

Xaa Thr His Xaa Xaa Arg Cys Arg Trp Xaa
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Iminodiacetic acid
<220> FEATURE:
<221> NAME/KEY: MISC_FEATURE
<222> LOCATION: (4)..(4)
<223> OTHER INFORMATION: Dpa
<220> FEATURE:
<221> NAME/KEY: MISC_FEATURE
<222> LOCATION: (5)..(5)
<223> OTHER INFORMATION: D-nipecotic acid
<220> FEATURE:
<221> NAME/KEY: MOD_RES
<222> LOCATION: (7)..(7)
<223> OTHER INFORMATION: Cys-S-CH3
<220> FEATURE:
<221> NAME/KEY: MISC_FEATURE
<222> LOCATION: (10)..(10)
<223> OTHER INFORMATION: Ahx-Ida(NH-PAL)-NH2

<400> SEQUENCE: 7

Xaa Thr His Xaa Xaa Arg Cys Arg Trp Xaa
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)

```
<223> OTHER INFORMATION: Iminodiacetic acid
<220> FEATURE:
<221> NAME/KEY: MISC_FEATURE
<222> LOCATION: (4)..(4)
<223> OTHER INFORMATION: Dpa
<220> FEATURE:
<221> NAME/KEY: MISC_FEATURE
<222> LOCATION: (5)..(5)
<223> OTHER INFORMATION: isonipecotic acid
<220> FEATURE:
<221> NAME/KEY: MOD_RES
<222> LOCATION: (7)..(7)
<223> OTHER INFORMATION: Cys-S-CH3
<220> FEATURE:
<221> NAME/KEY: MISC_FEATURE
<222> LOCATION: (10)..(10)
<223> OTHER INFORMATION: Ahx-Ida(NH-PAL)-NH2

<400> SEQUENCE: 8

Xaa Thr His Xaa Xaa Arg Cys Arg Trp Xaa
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Acetyl-Gly-Iminodiacetic acid
<220> FEATURE:
<221> NAME/KEY: MISC_FEATURE
<222> LOCATION: (4)..(4)
<223> OTHER INFORMATION: Dpa
<220> FEATURE:
<221> NAME/KEY: MISC_FEATURE
<222> LOCATION: (5)..(5)
<223> OTHER INFORMATION: beta-homoproline
<220> FEATURE:
<221> NAME/KEY: MOD_RES
<222> LOCATION: (7)..(7)
<223> OTHER INFORMATION: Cys-S-CH3
<220> FEATURE:
<221> NAME/KEY: MISC_FEATURE
<222> LOCATION: (10)..(10)
<223> OTHER INFORMATION: Ahx-Ida(NH-PAL)-NH2

<400> SEQUENCE: 9

Xaa Thr His Xaa Xaa Arg Cys Arg Trp Xaa
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Iminodiacetic acid
<220> FEATURE:
<221> NAME/KEY: MISC_FEATURE
<222> LOCATION: (4)..(4)
<223> OTHER INFORMATION: Dpa
<220> FEATURE:
<221> NAME/KEY: MISC_FEATURE
<222> LOCATION: (5)..(5)
<223> OTHER INFORMATION: beta-alanine
<220> FEATURE:
<221> NAME/KEY: MOD_RES
<222> LOCATION: (7)..(7)
<223> OTHER INFORMATION: Cys-S-CH3
```

```
<220> FEATURE:
<221> NAME/KEY: MISC_FEATURE
<222> LOCATION: (10)..(10)
<223> OTHER INFORMATION: Ahx-Ida(NH-PAL)-NH2

<400> SEQUENCE: 10

Xaa Thr His Xaa Xaa Arg Cys Arg Trp Xaa
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Iminodiacetic acid
<220> FEATURE:
<221> NAME/KEY: MISC_FEATURE
<222> LOCATION: (4)..(4)
<223> OTHER INFORMATION: Dpa
<220> FEATURE:
<221> NAME/KEY: MISC_FEATURE
<222> LOCATION: (5)..(5)
<223> OTHER INFORMATION: D-nipecotic acid
<220> FEATURE:
<221> NAME/KEY: MISC_FEATURE
<222> LOCATION: (10)..(10)
<223> OTHER INFORMATION: Ahx-Ida(NH-PAL)-NH2

<400> SEQUENCE: 11

Xaa Thr His Xaa Xaa Arg Cys Arg Trp Xaa
1               5                   10
```

HEPCIDIN MIMETIC PEPTIDES AND USES THEREOF

CROSS-REFERENCE TO RELATED APPLICATIONS

This application claims priority to U.S. Provisional Application No. 61/976,489, filed, Apr. 7, 2014 and U.S. Provisional Application No. 62/085,817, filed Dec. 1, 2014, each of which is hereby incorporated by reference in its entirety.

BACKGROUND

Hepcidin, a peptide hormone produced by the liver, is a regulator of iron metabolism and controls the transfer of iron from iron stores or the diet to red blood cells for incorporation into hemoglobin in humans and other mammals. Hepcidin acts by binding to the iron export channel ferroportin, and causing its internalization and degradation. When hepcidin removes ferroportin from the cell surface, the transfer or iron from either cellular stores within the body or dietary content in the intestine is prevented. Human hepcidin is a 25-amino acid peptide (Hep25). See Krause et al. (2000) FEBS Lett 480: 147-150, and Park et al. (2001) J Biol Chem 276:7806-7810, which is hereby incorporated by reference in its entirety and, for example, for the sequence of Hep25. The structure of the bioactive 25-amino acid form of hepcidin is a hairpin with 8 cysteines that form 4 disulfide bonds as described by Jordan et al. (2009) J Biol Chem 284:24155-67, which is hereby incorporated by reference in its entirety and, for example, for the structure and other information about the sequence. The N-terminal region has been shown to be required for iron-regulatory function, and deletion of 5 N-terminal amino acid residues results in a loss of iron-regulatory function (Nemeth et al. (2006) Blood 107:328-33). This finding has resulted in the design of drug-like hepcidin mimetic peptides (Preza et al., *Clin Invest.* 2011; 121(12):4880-4888).

Since either deficiency or excess of iron results in disease, hepcidin levels vary in order to maintain iron stores within a physiologically acceptable range. When hepcidin levels are abnormally low, iron transfer through ferroportin is correspondingly high. Consequently iron absorption from the diet is unrestricted and severe iron overload may develop that causes cell damage and organ failure. Conversely, when hepcidin levels are abnormally high, restriction in iron transfer to the developing red cell can cause reduction in erythropoiesis and eventually result in anemia.

Hepcidin mimetic peptides have potential use in a number of different hematological and metabolic diseases in which hepcidin levels are abnormally low including iron loading anemias and hereditary hemochromatosis. Iron-loading anemias such as beta thalassemia and myelodysplastic syndrome are characterized by the presence of ineffective erythropoiesis which contributes to severe anemia and also causes a reduction in hepcidin production, leading to severe iron overload. Complications from iron overload are a major cause of morbidity and mortality for these patients. Hepcidin deficiency is the main cause of iron overload in untransfused patients, and contributes to iron overload in transfused patients. The current treatment for iron overload in these patients is iron chelation which is very burdensome, sometimes ineffective and accompanied by frequent side effects.

Additionally, abnormally low hepcidin levels are associated with other iron overload diseases such as hereditary hemochromatosis or chronic liver disease. Hereditary hemochromatosis (HH) is a genetic iron overload disease that is mainly caused by hepcidin deficiency, or very rarely by hepcidin resistance. This allows excessive absorption of iron from the diet and development of iron overload. Clinical manifestations of HH may include liver disease (hepatic cirrhosis, hepatocellular carcinoma), diabetes, and heart failure. Currently, the only treatment for HH is regular phlebotomy, which is effective but very burdensome for the patients.

Hepcidin mimetic peptides may also be used to regulate the rate of erythropoiesis in diseases where abnormally accelerated erythropoiesis is present, such as polycythemia vera.

The use of hepcidin mimetic peptides for the treatment of such diseases requires compounds that are highly active in producing hepcidin activity following administration but which are sufficiently stable and soluble to be appropriately formulated for administration. There is still a need for compounds to treat such conditions. The embodiments disclosed herein satisfy these needs and others.

SUMMARY

Embodiments disclosed herein provide compounds, or a pharmaceutically acceptable salt thereof, of Formula I:

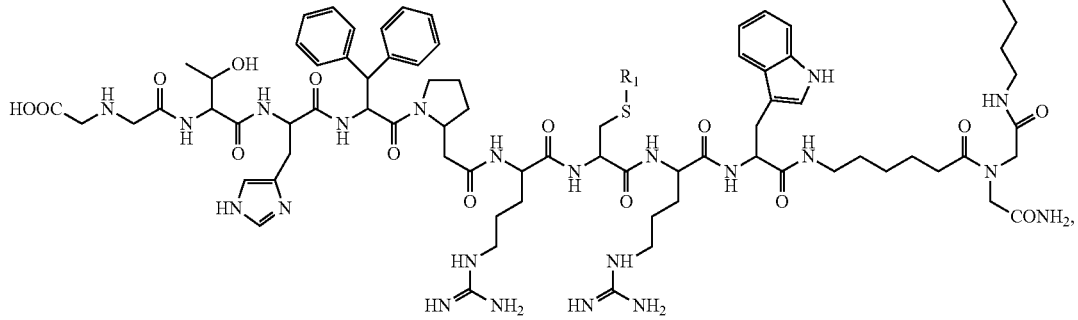

wherein $R_1$ is, —S—$Z_1$; —$Z_2$, —SH, —C(=O)—$Z_3$ or —S—C(=O)—$Z_3$, wherein:

$Z_1$ is substituted or unsubstituted $C_1$-$C_{18}$ alkyl or $C_1$-$C_{18}$ alkenyl, wherein the $C_1$-$C_{18}$ alkyl or $C_1$-$C_{18}$ alkenyl is branched or unbranched;

$Z_2$ is substituted or unsubstituted $C_1$-$C_{18}$ alkyl or $C_1$-$C_{18}$ alkenyl, wherein the $C_1$-$C_{18}$ alkyl or $C_1$-$C_{18}$ alkenyl is branched or unbranched;

$Z_3$ is substituted or unsubstituted $C_1$-$C_{18}$ alkyl or $C_1$-$C_{18}$ alkenyl, wherein the $C_1$-$C_{18}$ alkyl or $C_1$-$C_{18}$ alkenyl is branched or unbranched.

In some embodiments, the compound is Compound 2, or a pharmaceutically acceptable salt thereof:

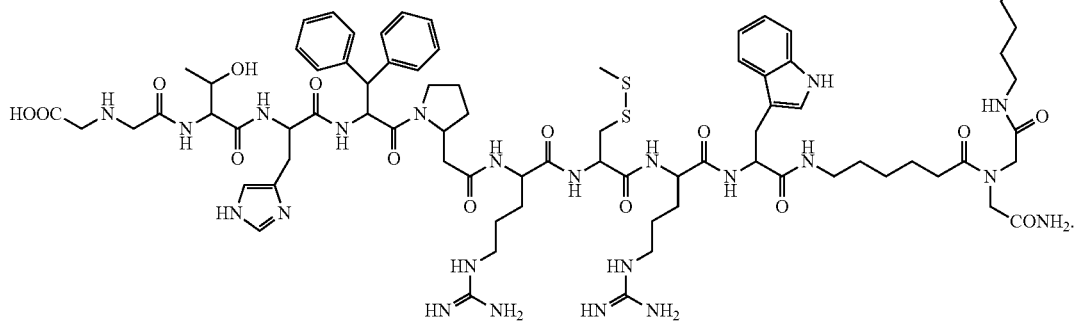

Compound 2

In some embodiments, the compound is Compound 3, or a pharmaceutically acceptable salt thereof:

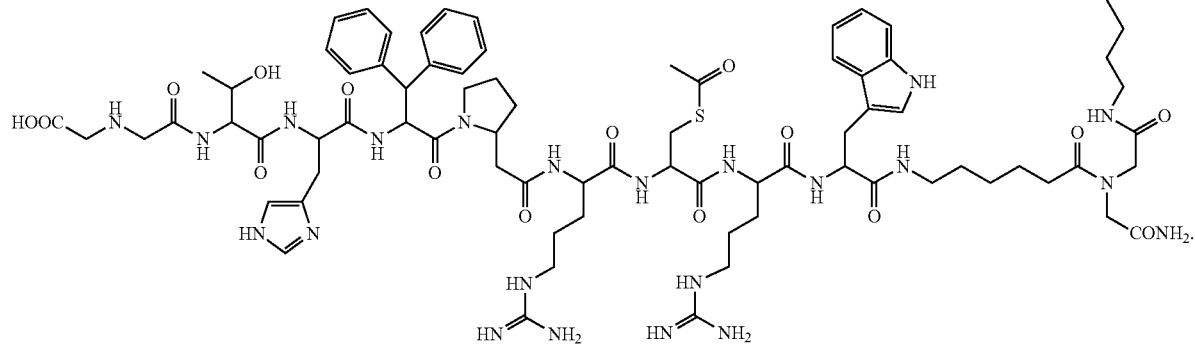

Compound 3

In some embodiments, the compound is Compound 4, or a pharmaceutically acceptable salt thereof:
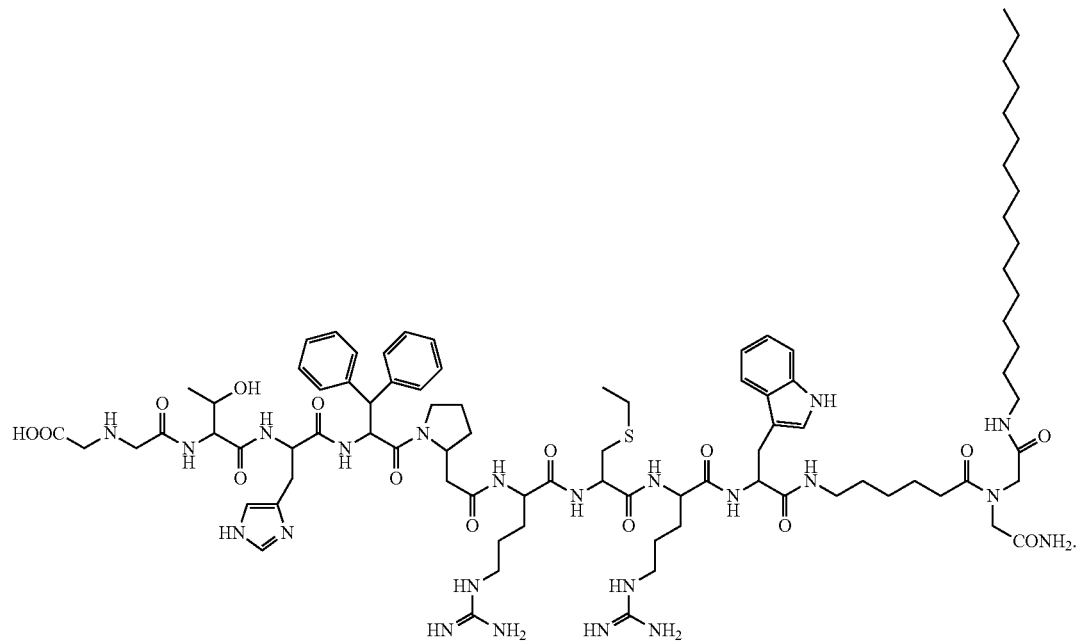
Compound 4
In some embodiments, compounds, or a pharmaceutically acceptable salt thereof, of Formula II are provided:
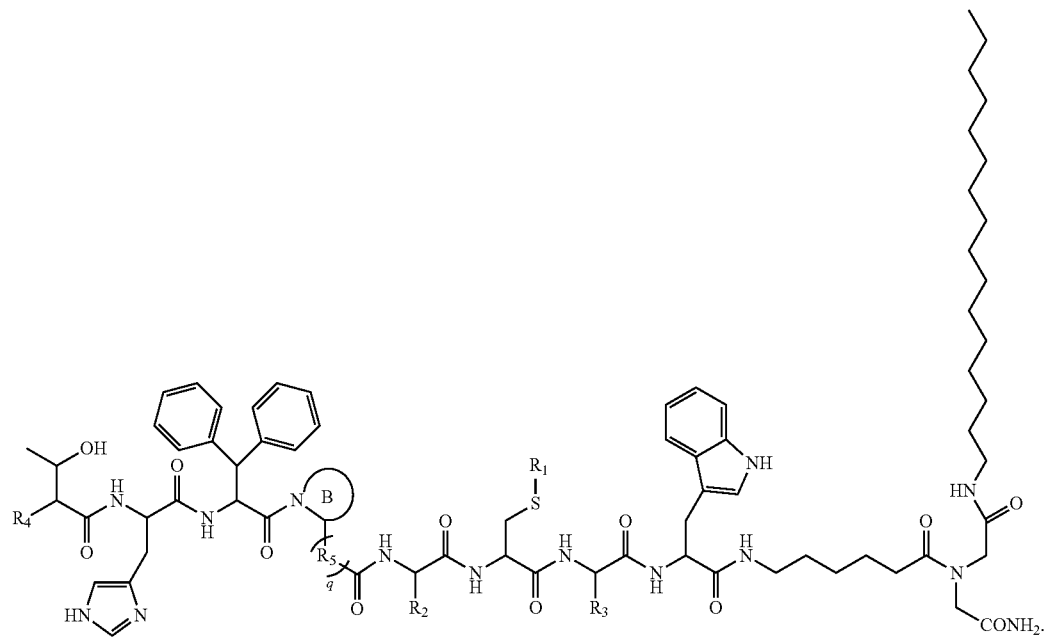
II wherein:

$R_1$ is, H, —S—$Z_1$; —$Z_2$, —SH, —C(=O)—$Z_3$, or —S—C(=O)—$Z_3$, $R_2$ and $R_3$ are each, independently, optionally substituted $C_4$-$C_7$ alkyl,

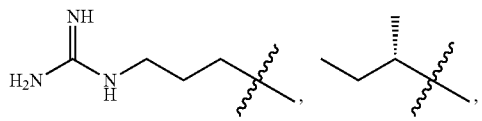

D-Arg, D-Ile, Leu, D-Leu, Thr, D-Thr, Lys, D-Lys, Val, D-Val, D-Nω,ω-dimethyl-arginine, L-Nω,ω-dimethyl-arginine, D-homoarginine, L-homoarginine, D-norarginine, L-norarginine, citrulline, a modified Arg wherein the guanidinium group is modified or substituted, norleucine, norvaline, beta homo-Ile, Ach, N-Me-Arg, N-Me-Ile;

$R_4$ is Ida, Asp, Acetyl-Asp, N-MeAsp, Acetyl-Gly-Ida, or Acetyl-Gly-Asp or a derivative thereof to remove its negative charge above pH 4;

$R_5$ is $CR_6R_7$, aryl or heteroaryl;

B is absent or forms a 5-7 membered ring; and q is 0-6, wherein when $R_5$ aryl or heteroaryl q is 1 and B is absent;

$Z_1$ is substituted or unsubstituted $C_1$-$C_{18}$ alkyl, wherein the $C_1$-$C_{18}$ alkyl is branched or unbranched;

$Z_2$ is substituted or unsubstituted $C_1$-$C_{18}$ alkyl, wherein the $C_1$-$C_{18}$ alkyl is branched or unbranched;

$Z_3$ is substituted or unsubstituted $C_1$-$C_{18}$ alkyl, wherein the $C_1$-$C_{18}$ alkyl is branched or unbranched;

$R_6$ and $R_7$ are each, independently, H, halo, optionally substituted $C_1$-$C_3$ alkyl, or haloalkyl, provided that when $R_1$ is H, the compound is not Compound 1.

In some embodiments, the compound is compound of Formula II-A, II-B, or II-C, or pharmaceutically acceptable salt thereof:

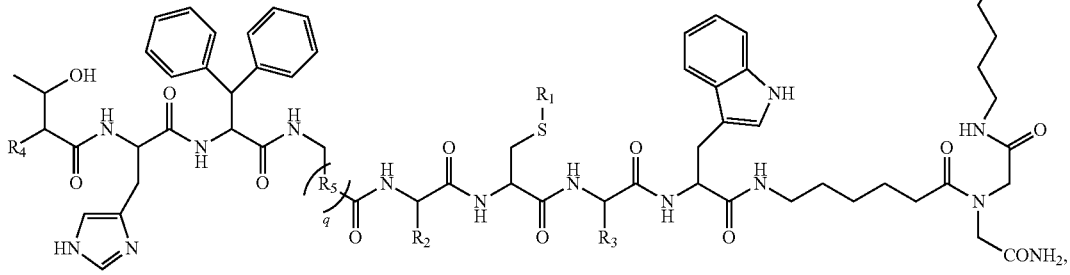

II-A

-continued
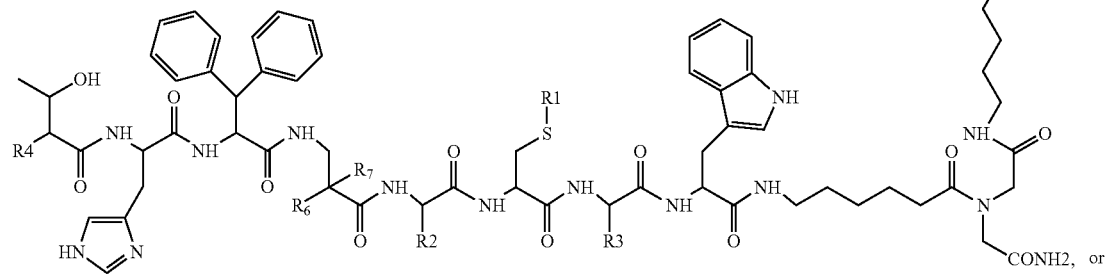
II-B
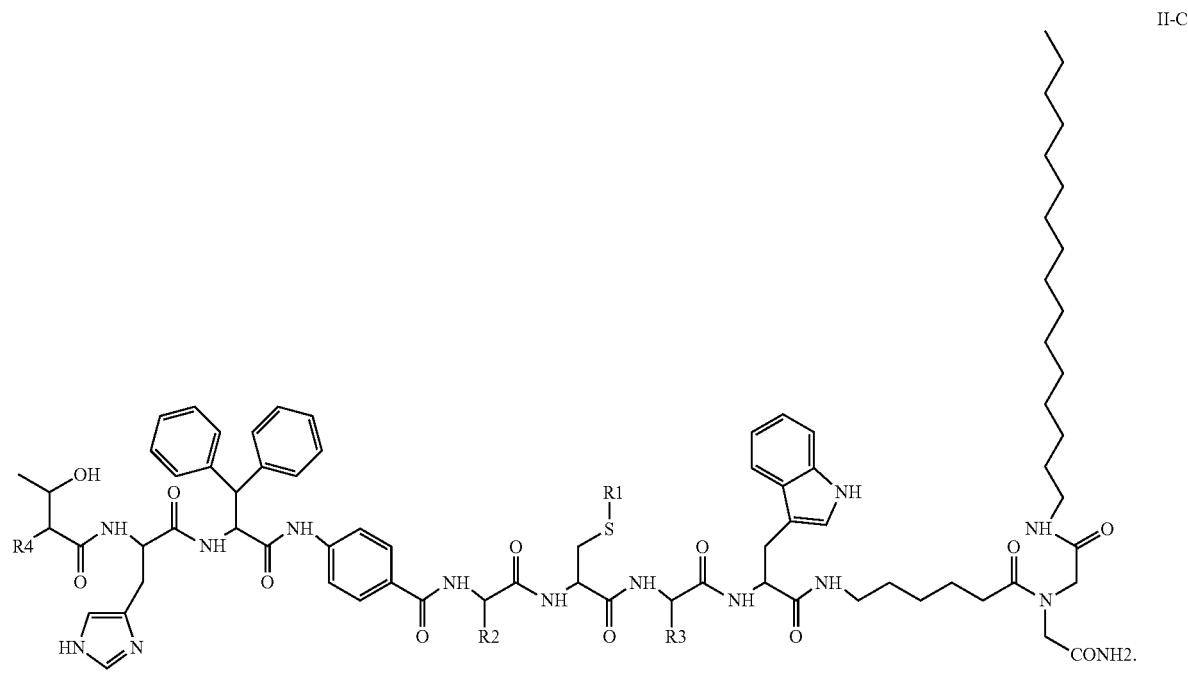
II-C

In some embodiments, compounds, or pharmaceutically acceptable salts thereof, of Formula III are provided:

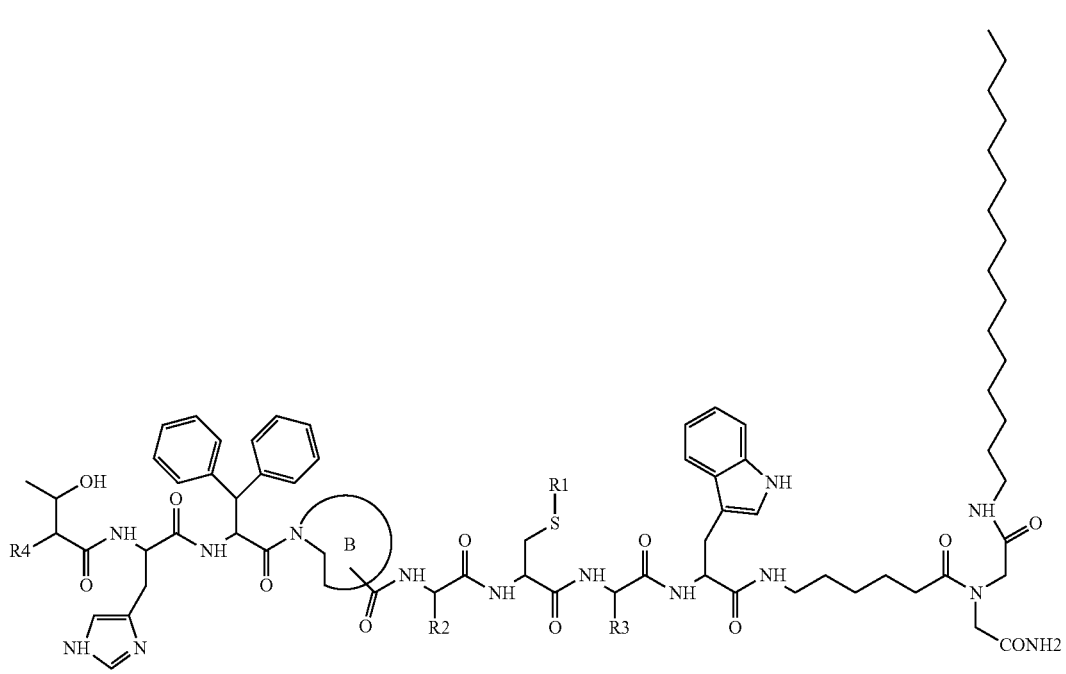

wherein:

$R_1$ is H, —S—$Z_1$, —$Z_2$, —SH, —S—C(=O)—$Z_3$, or —C(=O)—$Z_3$ $R_2$ and $R_3$ are each, independently, optionally substituted $C_4$-$C_7$ alkyl,

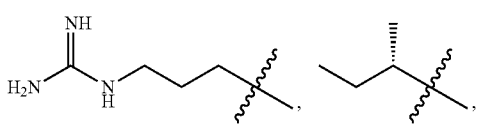

D-Arg, D-Ile, Leu, D-Leu, Thr, D-Thr, Lys, D-Lys, Val, D-Val, D-Nω,ω-dimethyl-arginine, L-Nω,ω-dimethyl-arginine, D-homoarginine, L-homoarginine, D-norarginine, L-norarginine, citrulline, a modified Arg wherein the guanidinium group is modified or substituted, norleucine, norvaline, beta homo-Ile, Ach, N-Me-Arg, N-Me-Ile;

$R_4$ is Ida, Asp, Acetyl-Asp, N-MeAsp, Acetyl-Gly-Ida, or Acetyl-Gly-Asp or a derivative thereof to remove its negative charge above pH 4;

B is absent or forms a 5-7 membered ring; and $Z_1$ is substituted or unsubstituted $C_1$-$C_{18}$ alkyl, wherein the $C_1$-$C_{18}$ alkyl is branched or unbranched;

$Z_2$ is substituted or unsubstituted $C_1$-$C_{18}$ alkyl, wherein the $C_1$-$C_{18}$ alkyl is branched or unbranched;

$Z_3$ is substituted or unsubstituted $C_1$-$C_{18}$ alkyl, wherein the $C_1$-$C_{18}$ alkyl is branched or unbranched;

provided that when $R_1$ is H, the compound is not Compound 1.

In some embodiments, the compound, or a pharmaceutically acceptable salt thereof, has a formula of Formula III-A with the variables as defined for Formula III.

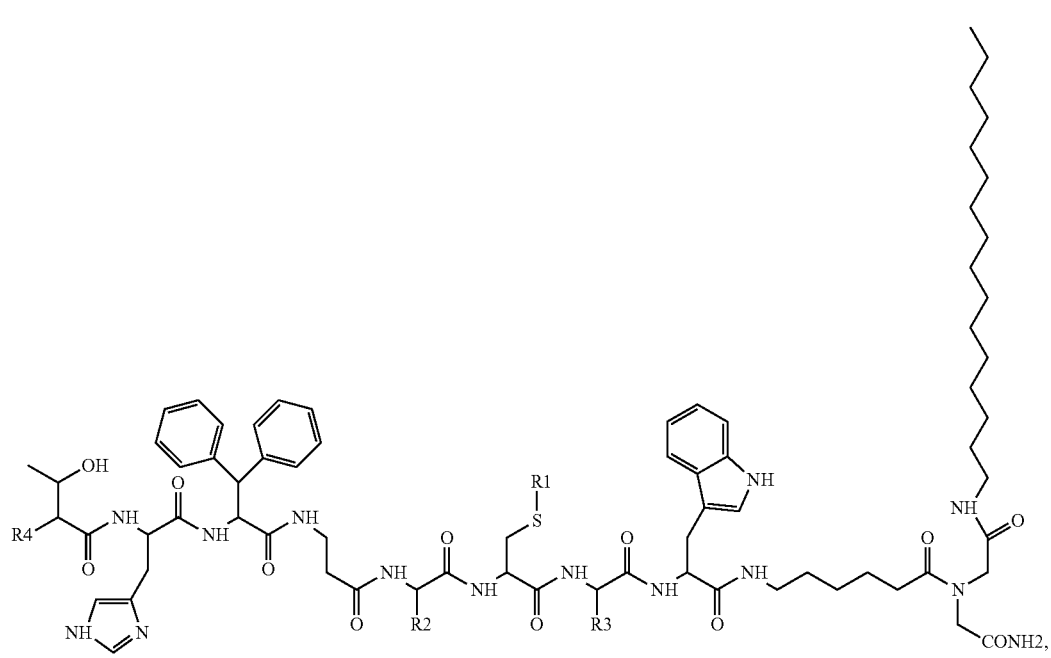
III-A
In some embodiments, the compound is a compound of Formula IV, or a pharmaceutically acceptable salt thereof:
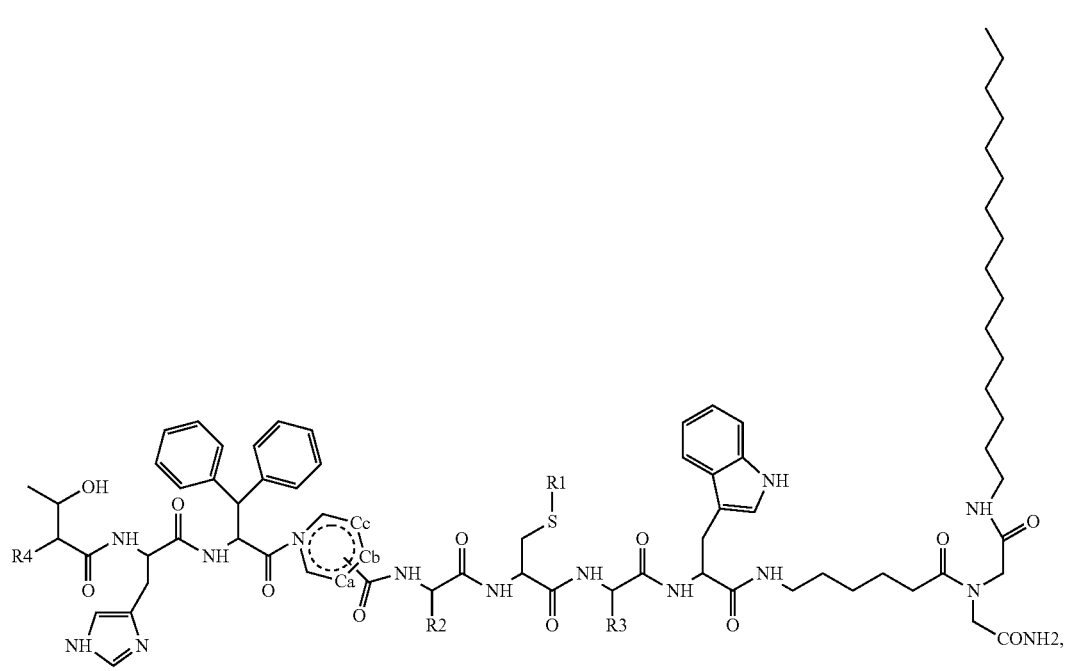
IV
wherein the carbonyl forms a bond with the 6-membered ring at $C_a$, $C_b$, or $C_c$ and with the variables as defined for Formula III.

In some embodiments, the compound is a compound of Formula V, or a pharmaceutically acceptable salt thereof,

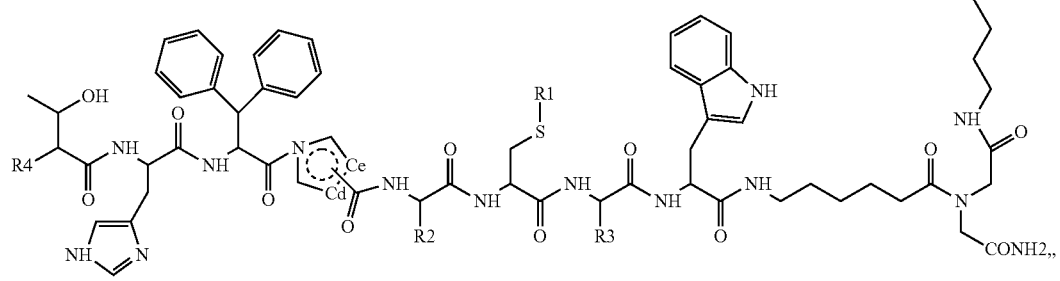

wherein the carbonyl forms a bond with the 5-membered ring at $C_d$ or $C_e$. and with the variables as defined for Formula III.

In some embodiments, the compound is a compound of Formula VI, or a pharmaceutically acceptable salt thereof,

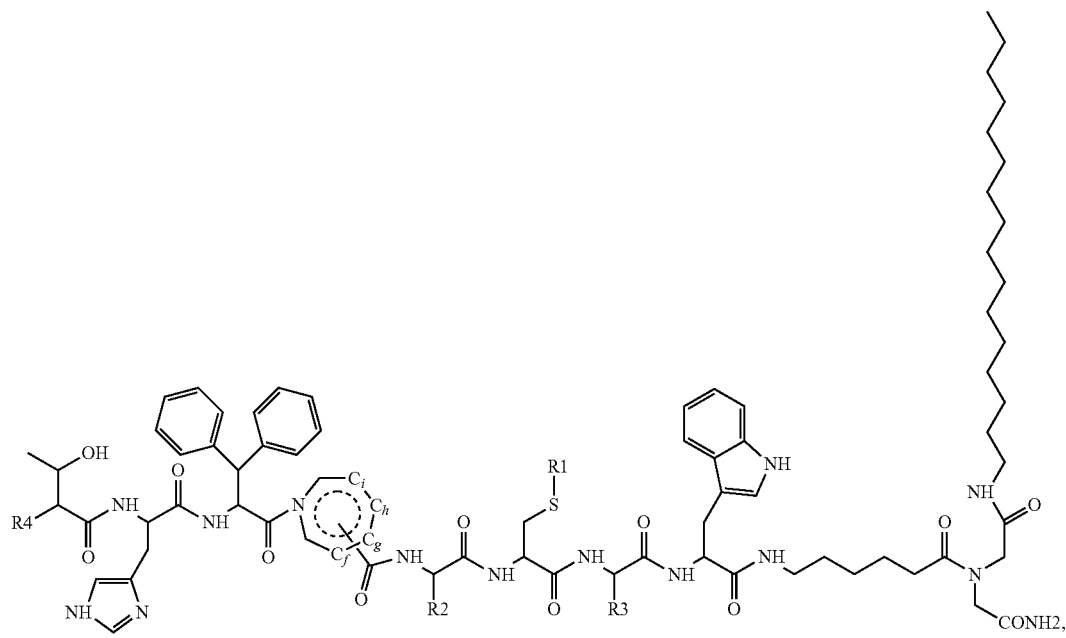

wherein the bond from the carbonyl forms a bond with the 7-membered ring at $C_f$, $C_g$, $C_h$, or $C_i$ and with the variables as defined for Formula III.

In some embodiments, Compound 5, or a pharmaceutically acceptable salt thereof is provided:

Compound 5

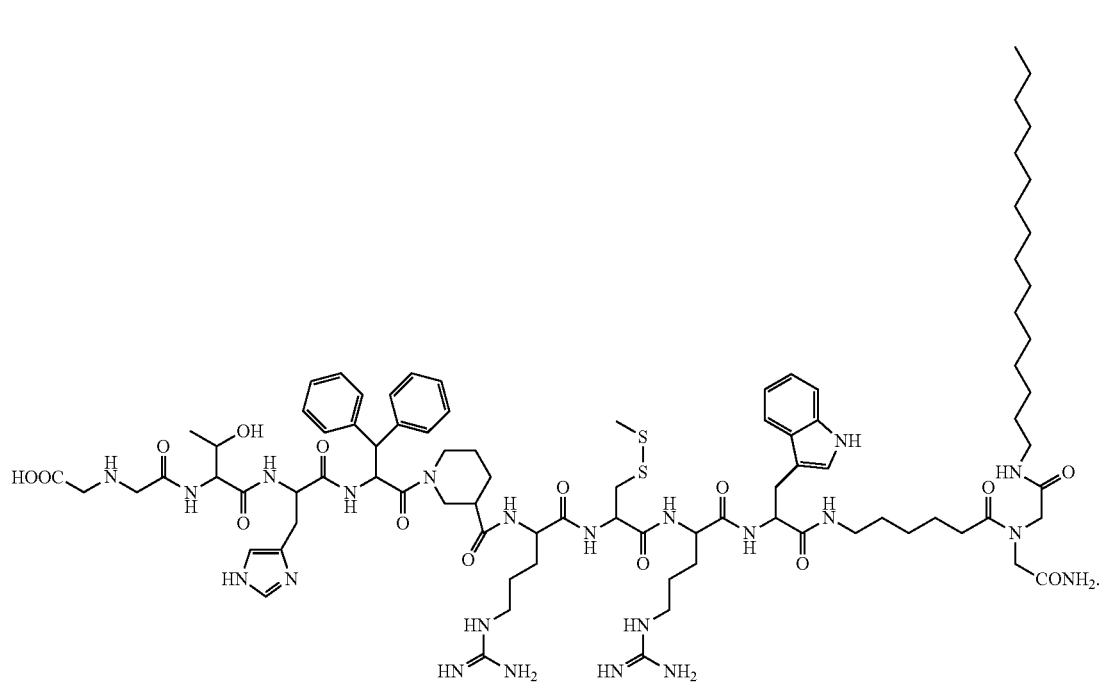

In some embodiments, Compound 6, or a pharmaceutically acceptable salt thereof is provided:

Compound 6

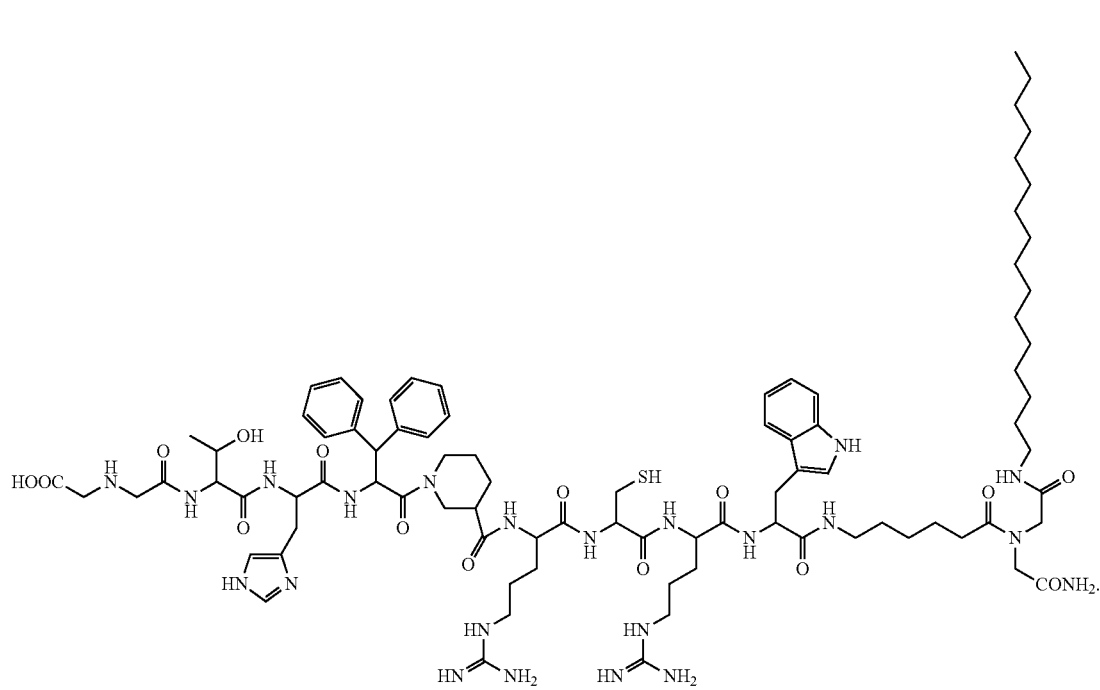

In some embodiments, compounds, or pharmaceutically acceptable salts thereof, selected from the group consisting of: Compound 2, Compound 3, Compound 4, Compound 5, Compound 6, Compound 7, Compound 8, Compound 9, and Compound 10, or a pharmaceutically acceptable salt thereof are provided.

In some embodiments, compounds, or a pharmaceutically acceptable salt thereof, of the formula $P_1$-$P_2$-$P_3$-$P_4$-$P_5$-$P_6$-$P_7$-$P_8$-$P_9$-$P_{10}$ or $P_{10}$-$P_9$-$P_8$-$P_7$-$P_6$-$P_5$-$P_4$-$P_3$-$P_2$-$P_1$, wherein $P_1$ to $P_{10}$ are as defined in the following table are provided:

| Compound # | P₁ | P₂ | P₃ | P₄ | P₅ | P₆ | P₇ | P₈ | P₉ | P₁₀ |
|---|---|---|---|---|---|---|---|---|---|---|
| 2 (SEQ ID NO: 2) | Ida | Thr | His | Dpa | bhPro | Arg | Cys-S—CH₃ | Arg | Trp | X₃ |
| 3 (SEQ ID NO: 3) | Ida | Thr | His | Dpa | bhPro | Arg | Cys-C(=O)CH₃ | Arg | Trp | X₃ |
| 4 (SEQ ID NO: 4) | Ida | Thr | His | Dpa | bhPro | Arg | Cys-CH₂—CH₃ | Arg | Trp | X₃ |
| 5 (SEQ ID NO: 5) | Ida | Thr | His | Dpa | Npc | Arg | Cys-S—CH₃ | Arg | Trp | X₃ |
| 6 (SEQ ID NO: 6) | Ida | Thr | His | Dpa | Npc | Arg | Cys | Arg | Trp | X₃ |
| 7 (SEQ ID NO: 7) | Ida | Thr | His | Dpa | D-Npc | Arg | Cys-S—CH₃ | Arg | Trp | X₃ |
| 8 (SEQ ID NO: 8) | Ida | Thr | His | Dpa | isoNpc | Arg | Cys-S—CH₃ | Arg | Trp | X₃ |
| 9 (SEQ ID NO: 9) | Acetyl-Gly-Ida | Thr | His | Dpa | bhPro | Arg | Cys-S—CH₃ | Arg | Trp | X₃ |
| 10 (SEQ ID NO: 10) | Ida | Thr | His | Dpa | bAla | Arg | Cys-S—CH₃ | Arg | Trp | X₃ | wherein: X₃ is Ahx-Ida(NH-PAL)-NH₂, Ida is Iminodiacetic acid; bhPro is beta-homoproline, Npc is L-nipecotic acid; isoNpc is isonipecotic acid and bAla is beta-alanine.

In some embodiments, compounds, or pharmaceutically acceptable thereof, of formula

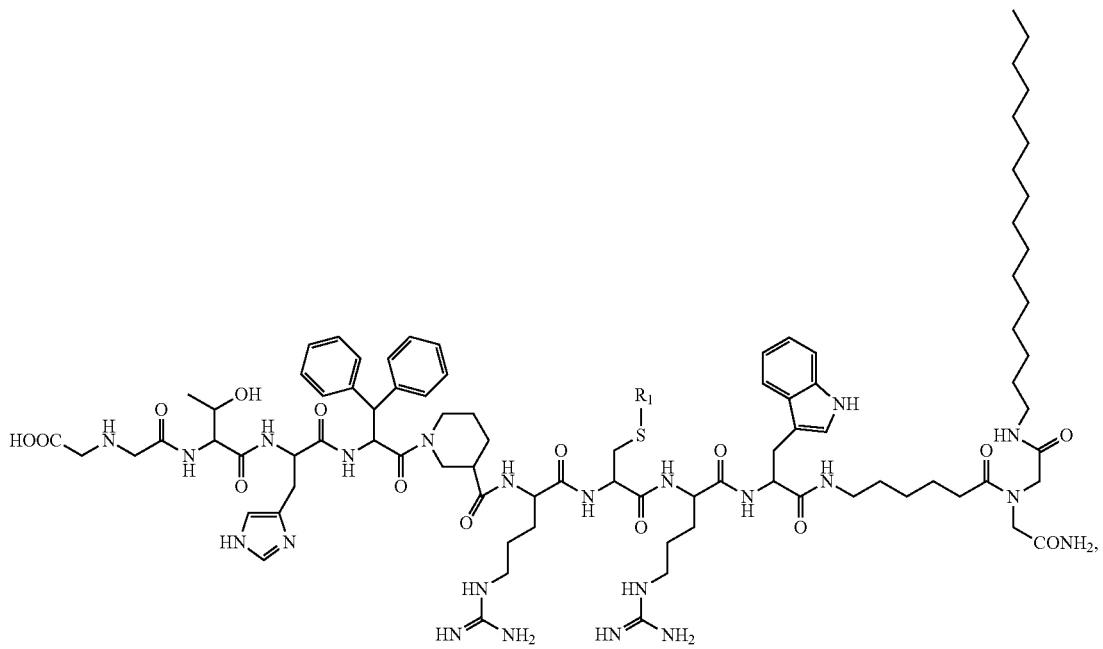

wherein R₁ is —S—CH₃ or H are provided.

In some embodiments, pharmaceutical compositions comprising a compound, or pharmaceutically acceptable thereof, of formula

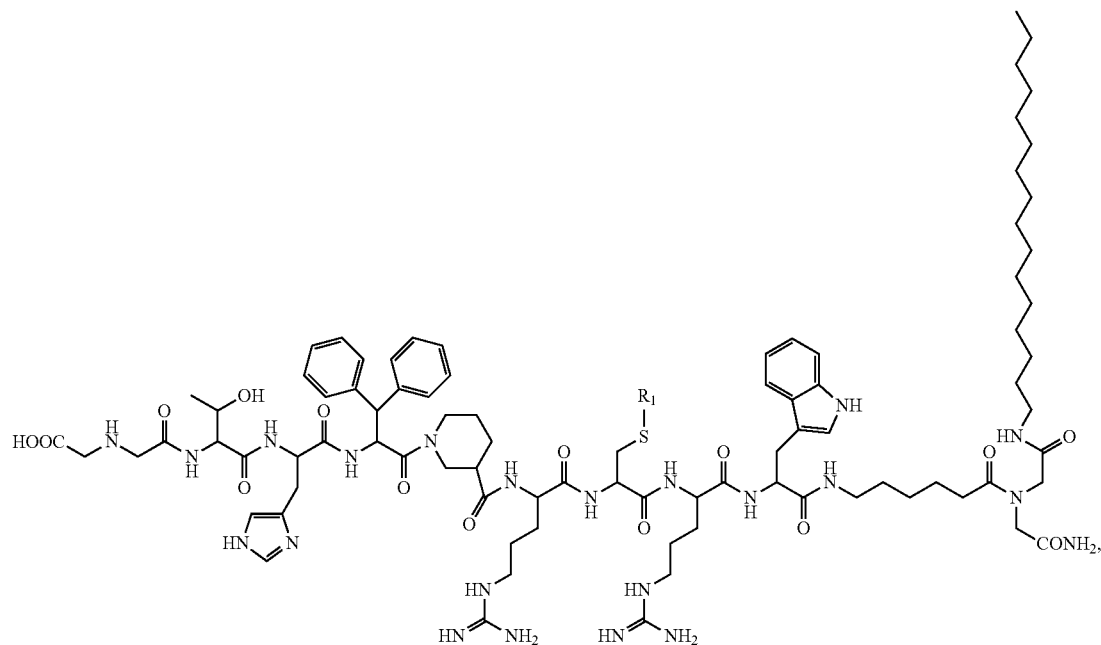

wherein $R_1$ is —S—$CH_3$ or H are provided.

In some embodiments, methods of reducing serum iron concentration in a subject comprising administering to the subject a pharmaceutical composition comprising a compound, or pharmaceutically acceptable thereof, of formula

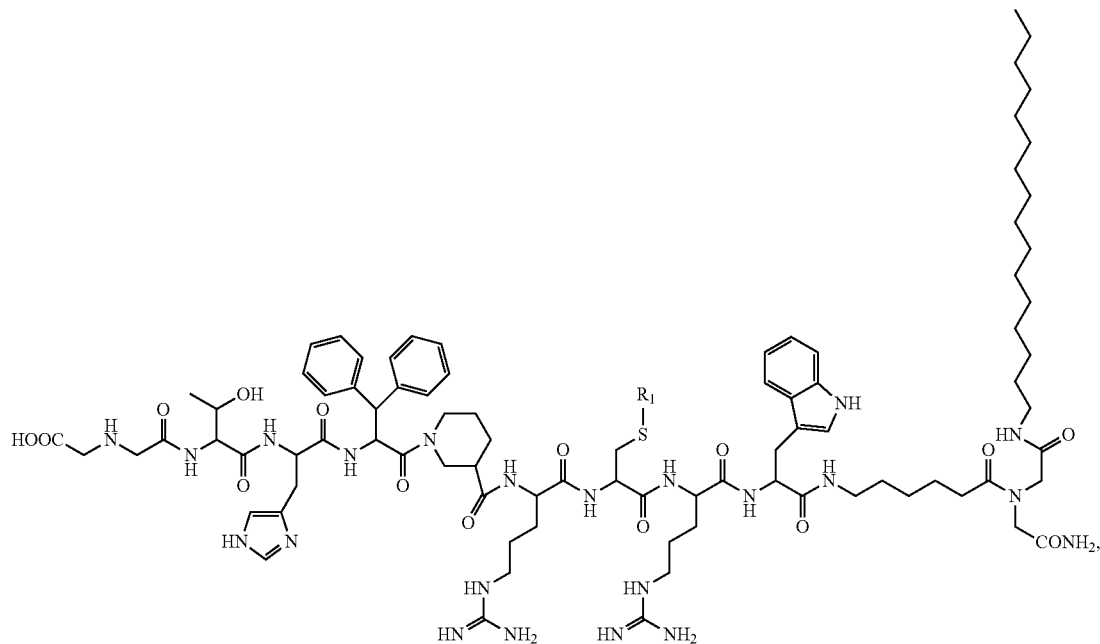

wherein $R_1$ is —S—$CH_3$ or H are provided.

In some embodiments, methods of treating a subject for beta thalassemia comprising administering to the subject a pharmaceutical composition comprising a compound, or pharmaceutically acceptable thereof, of formula

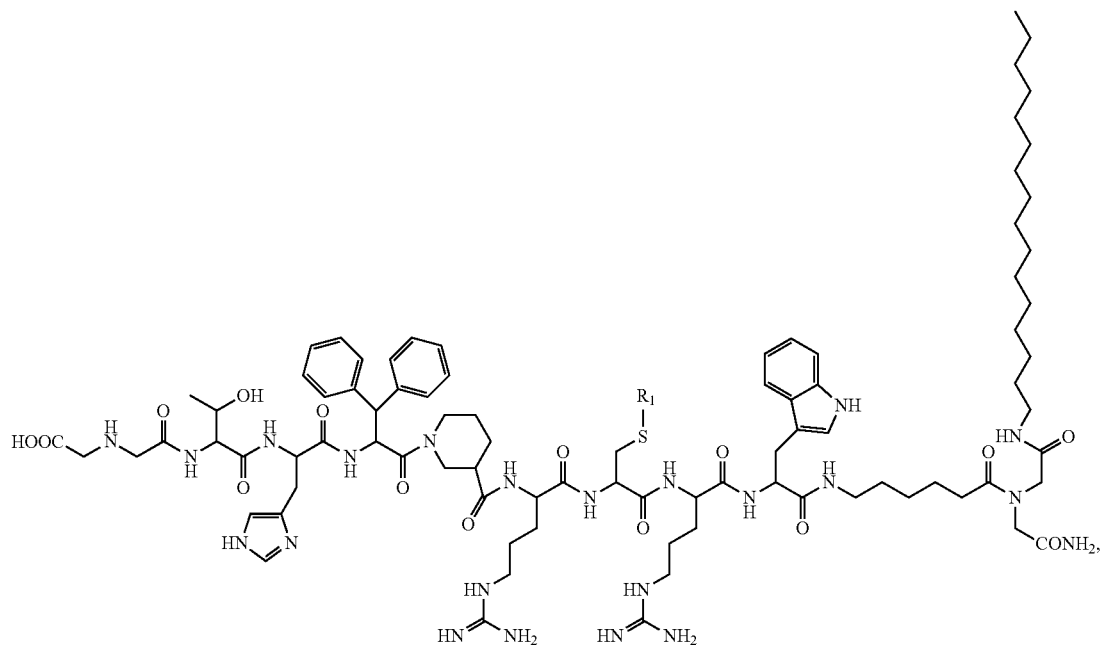

wherein R₁ is —S—CH₃ or H are provided.

In some embodiments, a compound that is administered to a subject is converted into Compound 6, or a pharmaceutically acceptable salt thereof.

In some embodiments, pharmaceutical compositions comprising a compound described herein and a pharmaceutically acceptable carrier are provided. In some embodiments, the pharmaceutical composition does not comprise, or is substantially free of Compound 1.

In some embodiments, methods of treating a subject in need of such treatment or for a disease recited herein are provided. In some embodiments, the methods comprise administering to the subject a compound described herein or a pharmaceutical composition described herein. In some embodiments, the disease is a disease of iron metabolism, beta thalassemia, hemochromatosis, iron-loading anemias, alcoholic liver disease, or chronic hepatitis C.

In some embodiments, the compound that is administered is converted into a compound of Compound 1, or a pharmaceutically acceptable salt thereof.

Compound 1

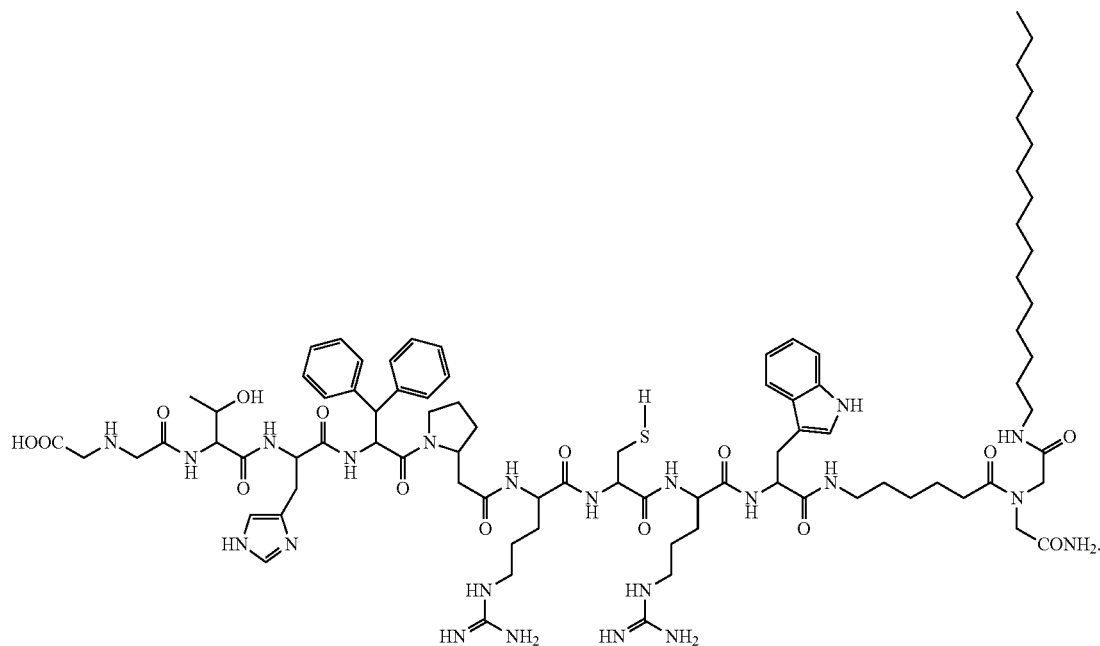

In some embodiments, the compound that is administered is not converted into a compound of Compound 1, or a pharmaceutically acceptable salt thereof.

DETAILED DESCRIPTION

Figure 1:
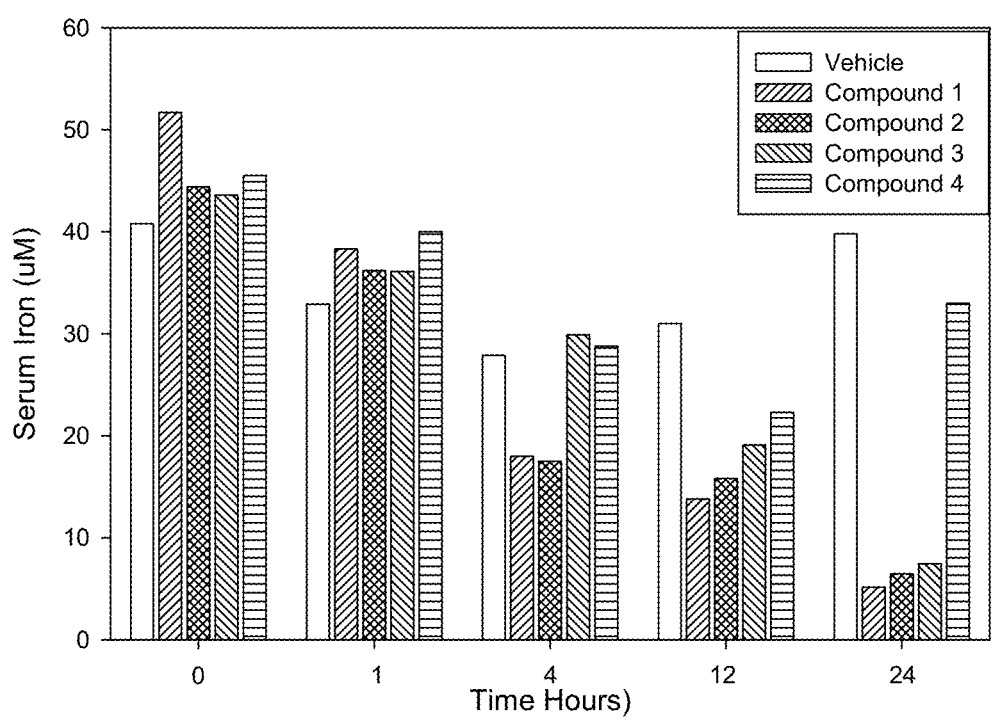
FIG. 1 illustrates the effect administration of compounds 1-4 have on serum iron levels in the rat after subcutaneous administration (7.5 mg/kg)

The compounds and compositions described herein can be used to treat various conditions and diseases described herein. The compound and compositions also have, superior, unexpected, and surprising properties and results including, but not limited to, superior solubility, superior in vitro and in vivo stability, and ability to reduce serum iron concentration. The compounds and compositions also have other unexpected and surprising properties as evidenced in the examples and the description contained herein. The compounds described herein can function as hepcidin mimetics. Such compounds with these characteristics that retain hepcidin mimetic activity allow for easier and more cost effective medicaments and lead to better methods of treatment.

Unless otherwise defined, all technical and scientific terms used herein have the same meaning as commonly understood by one of ordinary skill in the art to which the embodiments disclosed belongs. Although methods and materials similar or equivalent to those described herein can be used in the practice or testing of the present embodiments, suitable methods and materials are described below. All publications, patent applications, patents, and other references mentioned herein are incorporated by reference in their entirety. In the case of conflict, the present specification, including definitions, will control. In addition, the materials, methods, and examples are illustrative only not intended to be limiting. Other features and advantages of the embodiments will be apparent from the following detailed description and claims.

For the purposes of promoting an understanding of the embodiments described herein, reference will be made to certain embodiments and specific language will be used to describe the same. The terminology used herein is for the purpose of describing particular embodiments only, and is not intended to limit the scope of the present disclosure.

Before the present compounds, compositions, proteins, peptides, etc., and methods are described, it is understood that these embodiments are not limited to the particular methodology, protocols, and reagents described, as these may vary. It also is to be understood that the terminology used herein is for the purpose of describing particular embodiments only, and is not intended to limit the scope of the present embodiments or claims.

As used herein, the phrase "in need thereof" means that the animal or mammal has been identified or suspected as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent.

As used herein, the term "subject," "individual" or "patient," used interchangeably, means any animal, including mammals, such as mice, rats, other rodents, rabbits, dogs, cats, swine, cattle, sheep, horses, or primates, such as humans. In some embodiments, the subject is a human.

As used herein, the terms "a" or "an" means that "at least one" or "one or more" unless the context clearly indicates otherwise.

The term "halo" refers to fluoro, chloro, bromo, or iodo. In some embodiments, the halo groups are fluoro, chloro, and bromo. In some embodiments, the halo groups are fluoro and chloro.

The general chemical terms used throughout have their usual meanings. For example, the term alkyl refers to a branched or unbranched saturated hydrocarbon group. The term "n-alkyl" refers to an unbranched alkyl group. The term "$C_x$-$C_y$ alkyl" refers to an alkyl group having from x to y carbon atoms, inclusively, in the branched or unbranched hydrocarbon group. By way of illustration, but without limitation, the term "$C_1$-$C_4$ alkyl" refers to a straight chain or branched hydrocarbon moiety having from 1 to 4 carbon atoms, including methyl, ethyl, n-propyl, isopropyl, n-butyl, isobutyl, sec-butyl, and tert-butyl. The term "$C_1$-$C_4$ n-alkyl" refers to straight chain hydrocarbon moieties having from 1 to 4 carbon atoms including methyl, ethyl, n-propyl, and n-butyl. $C_x$-$C_y$, x can be from 1 to 10 and y is from 2 to 20. The term "$C_3$-$C_6$ cycloalkyl" refers to cyclopropyl, cyclobutyl, cyclopentyl, and cyclohexyl. The term "$C_3$-$C_7$ cycloalkyl" also includes cycloheptyl. Cycloalkylalkyl refers to cycloalkyl moieties linked through an alkyl linker chain, as for example, but without limitation, cyclopropylmethyl, dimethyl cyclopropyl, cyclopropylethyl, cyclopropylpropyl, cyclopropylbutyl, cyclobutylmethyl, cyclobutylethyl, cyclobutylpropyl, cyclopentylmethyl, cyclopentylethyl, cyclopentylpropyl, cyclohexylmethyl, cyclohexylethyl, and cyclohexylpropyl. Each alkyl, cycloalkyl, and cycloalkylalkyl group may be optionally substituted, such as, but not limited to, as specified herein. In some embodiments, the group is mono or di-substituted. In some embodiments, the alkyl is a $C_1$-$C_3$, $C_1$-$C_4$, $C_1$-$C_6$, $C_4$-$C_6$, or $C_1$-$C_{10}$ alkyl. In some embodiments, the substitution is another alkyl group or a halo group. The substitution can also be an aromatic or other ring group.

Carbocycle is either a monocyclic or a bicyclic non-aromatic ring system. A carbocycle can include heteroatoms (i.e., heterocycle). A carbocycle may contain double bonds, but they are not aromatic. Examples of carbocycles include, but are not limited to, cyclopropyl, cyclobutyl, cyclopentyl, cyclohexyl, and cycloheptyl. In some embodiments, the carbocycle is

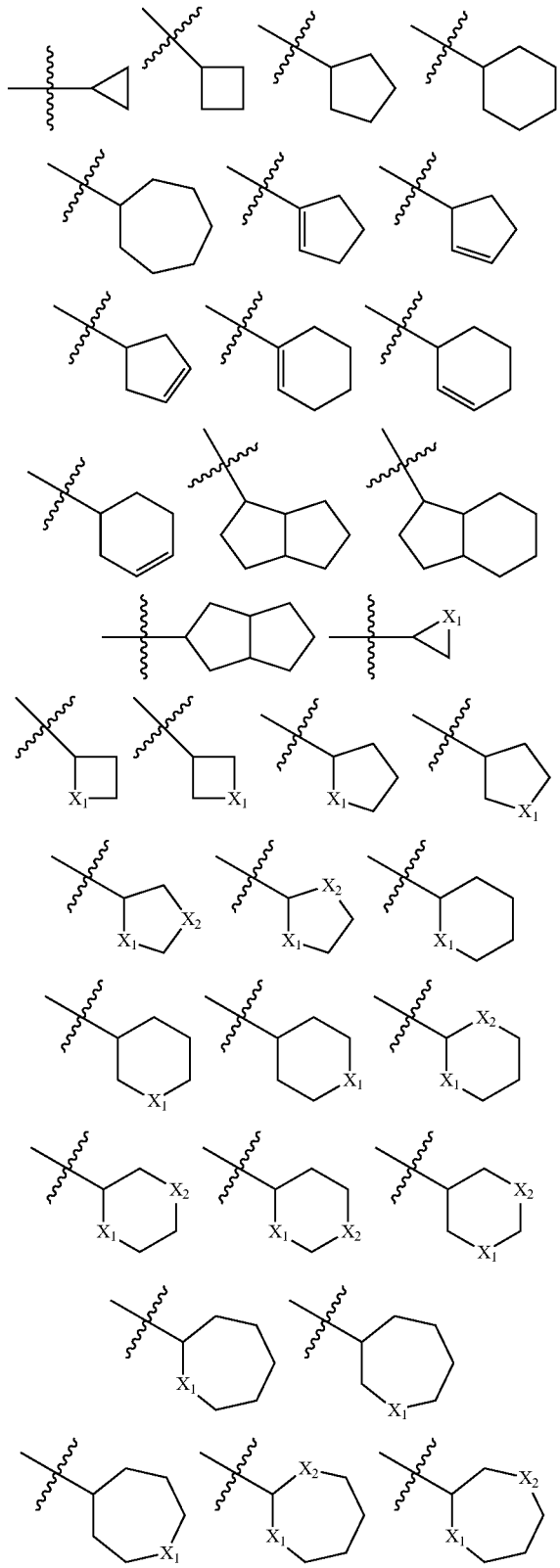
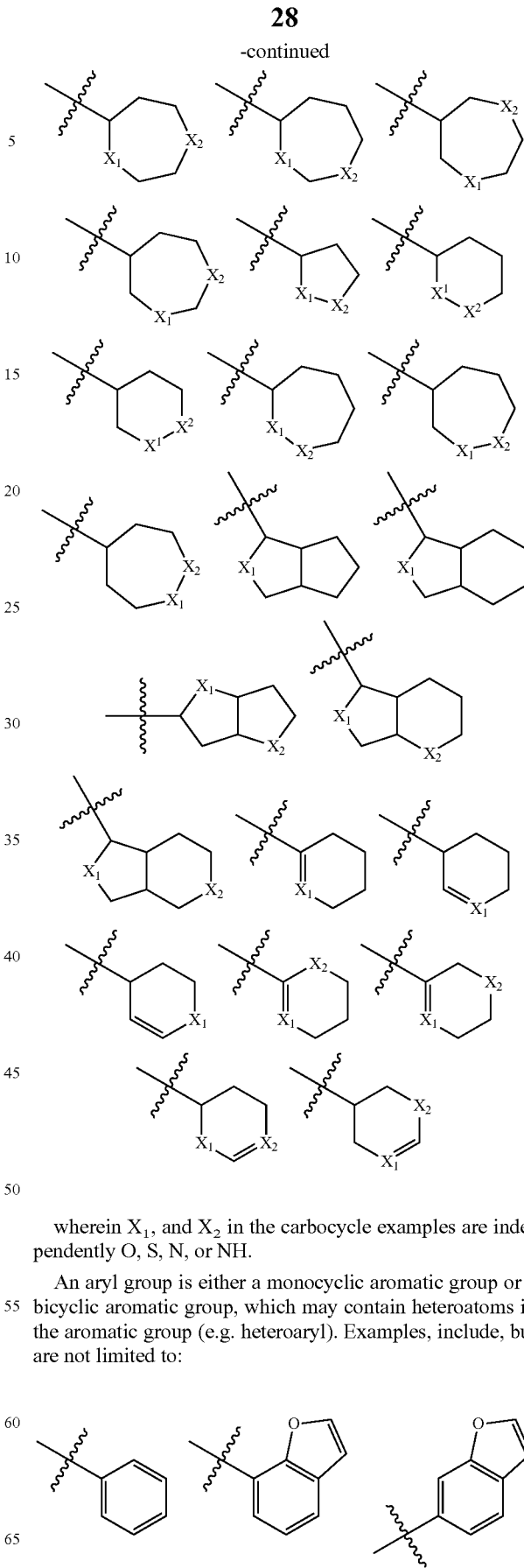

wherein $X_1$, and $X_2$ in the carbocycle examples are independently O, S, N, or NH.

An aryl group is either a monocyclic aromatic group or a bicyclic aromatic group, which may contain heteroatoms in the aromatic group (e.g. heteroaryl). Examples, include, but are not limited to:

29
-continued
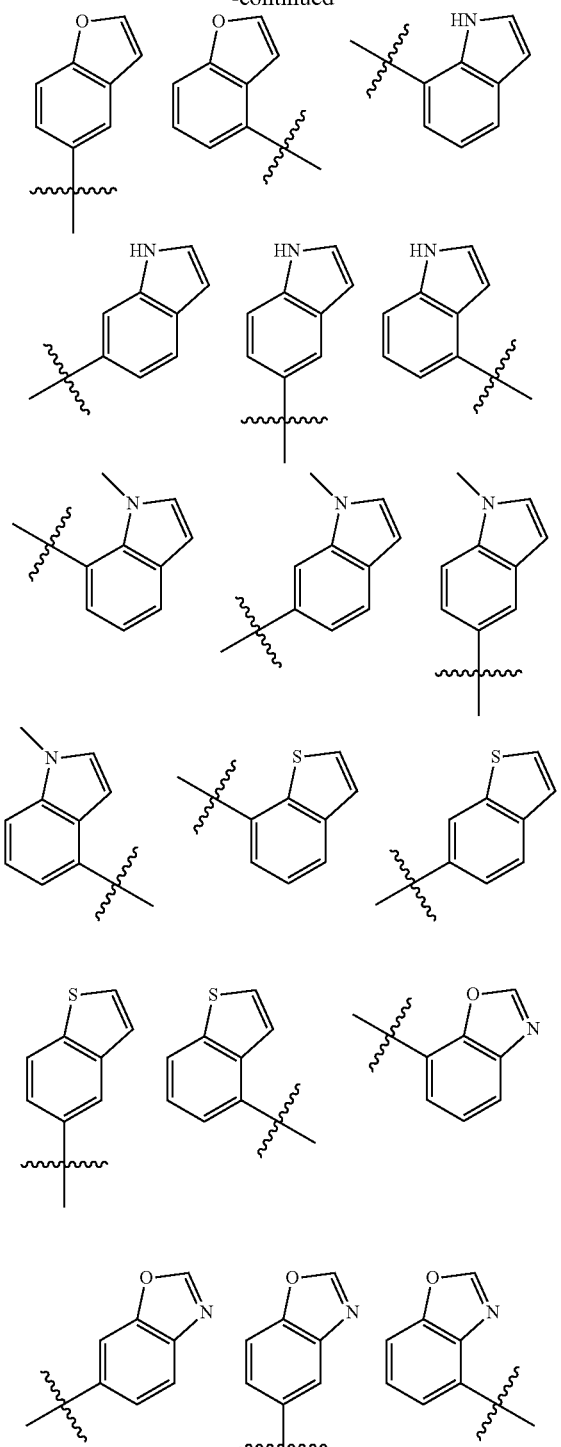
30
-continued
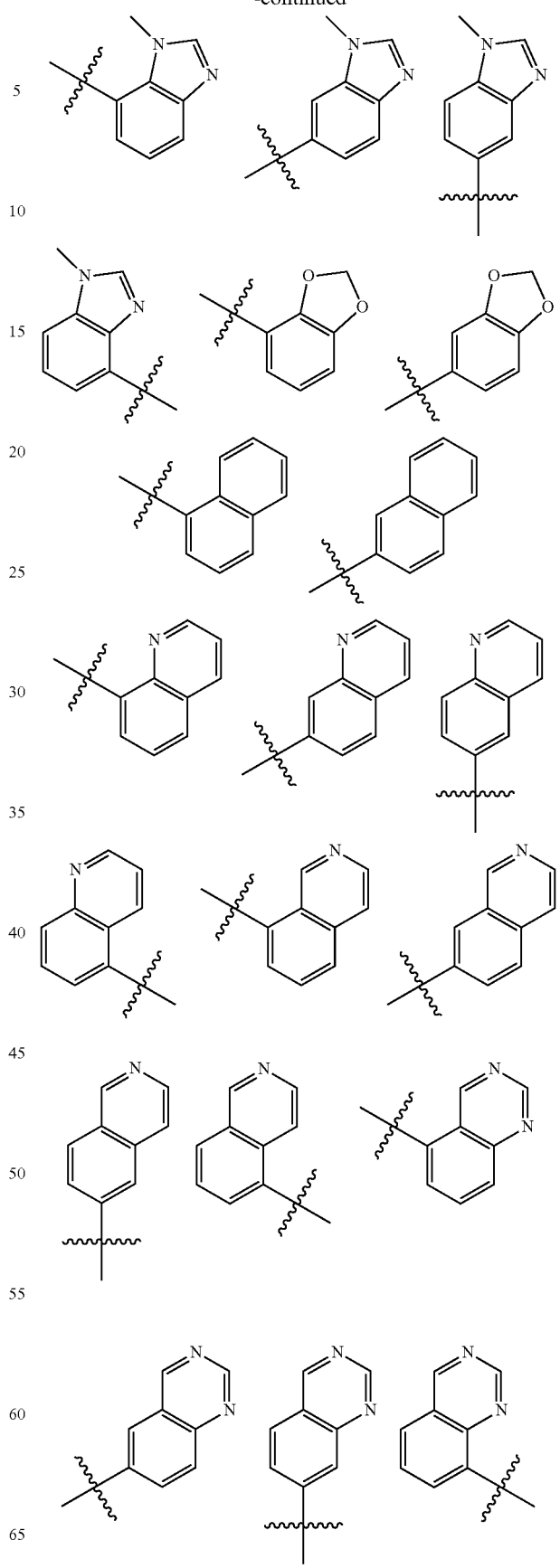

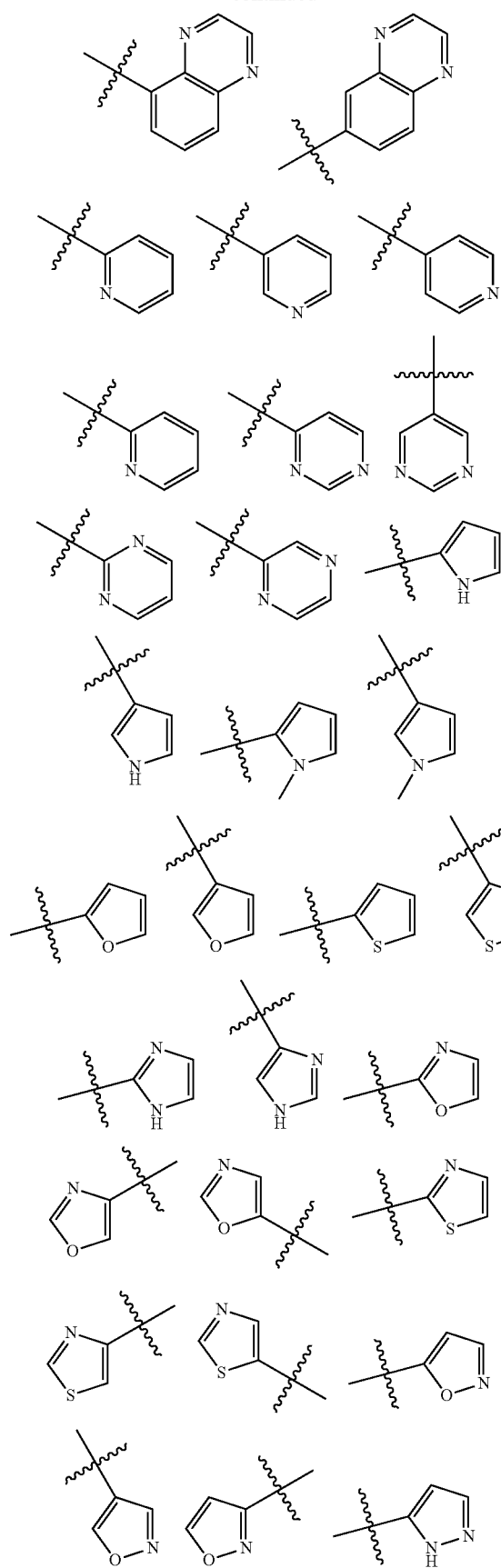
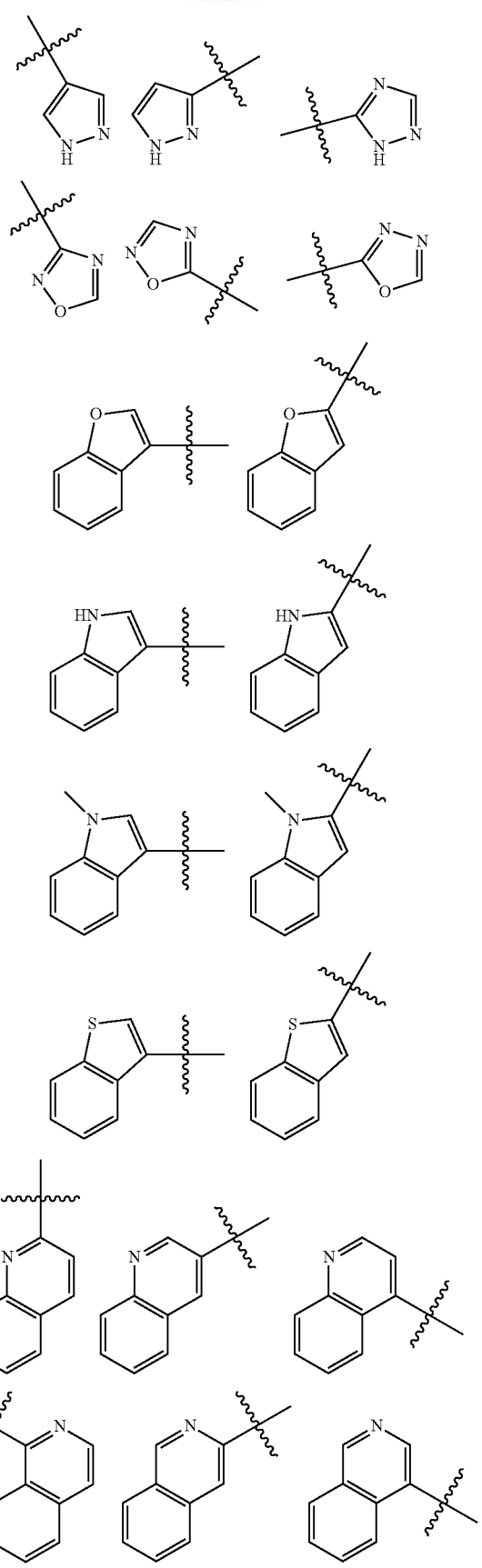

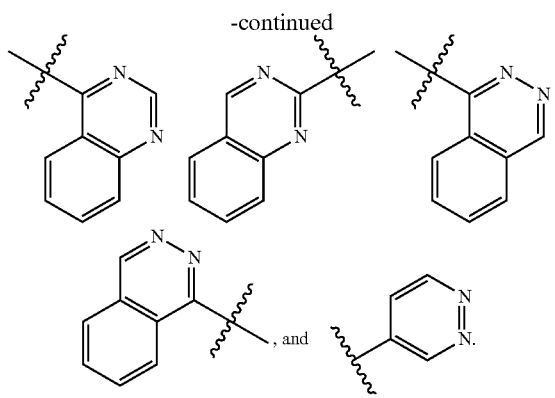

Aryl, alkyl, carbocycle (non-aromatic)/heterocycle (non-aromatic with 1-3 heteroatoms, including O, N, S) can be either unsubstituted, or substituted with small substitution groups. Small substitution groups can be cyano, halogen, alkyl (branched and unbranched alkyl), halogenated alkyl, hydroxyl, alkyloxy, amino, alkylamino, dialkylamino, mercaptanyl, alkylmercaptanyl, alkylsulfonyl, aminosulfonyl, alkylaminosulfonyl, alkylcarbonyl, alkoxycarbonyl, aminocarbonyl, alkylaminocarbonyl, dialkylaminocarbonyl, aryl, arylalkyl, carbocycle or carbocycle-alkyl. In some embodiments, the small substitution groups are selected from F, Cl, Br, $CH_3$, $CH_2CH_3$, $CH_2F$, $CHF_2$, $CF_3$, n-Pr, n-Bu, i-Bu, sec-Bu, i-Pr, t-Bu, CN, OH, OMe, OEt, O-iPr, $OCF_3$, $NH_2$, NHMe, $NMe_2$, methoxycarbonyl, methanesuflonyl, Ph, benzyl, $MeSO_2$, formyl, and acetyl.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments. Where a numerical value is used with the term "about" the numerical value without the term "about" is also disclosed and can be used without the term "about."

As used herein, the term "animal" includes, but is not limited to, humans and non-human vertebrates such as wild, domestic, and farm animals.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the phrase "integer from X to Y" means any integer that includes the endpoints. That is, where a range is disclosed, each integer in the range including the endpoints is disclosed. For example, the phrase "integer from X to Y" discloses 1, 2, 3, 4, or 5 as well as the range 1 to 5.

As used herein, the term "mammal" means a rodent (i.e., a mouse, a rat, or a guinea pig), a monkey, a cat, a dog, a cow, a horse, a pig, or a human. In some embodiments, the mammal is a human.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment.

As used herein, the terms "treat," "treated," or "treating" can refer to therapeutic treatment and/or prophylactic or preventative measures wherein the object is to prevent or slow down (lessen) an undesired physiological condition, disorder or disease, or obtain beneficial or desired clinical results. For purposes of the embodiments described herein, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment can also include eliciting a clinically significant response without excessive levels of side effects. Treatment also includes prolonging survival as compared to expected survival if not receiving treatment.

The definition of some of the abbreviations used herein are given below. Other abbreviations are provided elsewhere in the present document. Any abbreviation not explicitly defined herein is used in accordance with customary usage by one of skill in the art.

| Abbreviation | Chemical name of amino acid or its analog |
|---|---|
| Ala | L-Alanine |
| Asp | L-Aspartic acid |
| Glu | L-Glutamic acid |
| Arg | L-Arginine |
| Lys | L-Lysine |
| Ile | L-Isoleucine |
| Gly | Glycine |
| Tyr | L-Tyrosine |
| Val | L-Valine |
| Phe | L-Phenylalanine |
| His | L-Histidine |
| Pro | L-Proline |

The compounds described herein (e.g. peptides) can also be in cyclic forms, cyclic truncated forms, cyclic truncated dimerized forms, and cyclic truncated trimerized forms of the compounds of the above formulas may be prepared using any known method. A truncated form has one or more amino acid residues removed from either end, or both, of the peptides or mimetics described herein. The peptides may have 1 or 2 amino acids removed from each end independently or internal to the C- and N-terminal of the compounds. As described herein, the compounds described herein can also be represented by the formula of $P_1$-$P_2$-$P_3$-$P_4$-$P_5$-$P_6$-$P_7$-$P_8$-$P_9$-$P_{10}$ or $P_{10}$-$P_9$-$P_8$-$P_7$-$P_6$-$P_5$-$P_4$-$P_3$-$P_2$-$P_1$. Accordingly, in some embodiments of $P_1$-$P_{10}$ 1, 2, 3, or 4 of the subunits is deleted as a terminal or internal deletion. In some embodiments, $P_1$ is absent. In some embodiments, $P_2$ is absent. In some embodiments, $P_3$ is absent. In some embodiments, $P_4$ is absent. In some embodiments, $P_5$ is absent. In some embodiments, $P_6$ is absent. In some embodiments, $P_7$ is absent. In some embodiments, $P_8$ is absent. In some embodiments, $P_9$ is absent. In some embodiments, $P_{10}$ is absent. In some embodiments, two of $P_1$-$P_{10}$ are absent. If one of $P_1$-$P_{10}$ is absent the peptide like bond is formed with the neighboring subunit. For example, if $P_4$ were absent, then $P_3$ would be bound to $P_5$.

According to some embodiments, cyclic forms of the compounds of the above formulas may be prepared by bridging free amino and free carboxyl groups. According to some embodiments, formation of the cyclic compounds may be conducted conventionally by treatment with a dehydrating agent by means known in the art, with suitable protection if needed. According to some embodiments, the open chain (linear form) to cyclic form reaction may involve a trans to cis isomerization of the proline. According to some embodiments, the open chain (linear form) to cyclic form reaction may involve intramolecular-cyclization.

Variants of the peptides described herein also included. The term "variant" refers to a protein or polypeptide in which one or more (i.e., 1, 2, 3, 4, etc.) amino acid substitutions, deletions, and/or insertions are present as compared to the amino acid sequence of an protein or peptide and includes naturally occurring allelic variants or alternative splice variants of an protein or peptide. The term "variant" includes the replacement of one or more amino acids in a peptide sequence with a similar or homologous amino acid(s) or a dissimilar amino acid(s). Some variants include alanine substitutions at one or more of amino acid positions. Other substitutions include conservative substitutions that have little or no effect on the overall net charge, polarity, or hydrophobicity of the protein. Conservative substitutions are set forth in the table below. According to some embodiments, the peptides or peptide mimetics have at least 60%, 65%, 70%, 75%, 80%, 85%, 88%, 95%, 96%, 97%, 98% or 99% sequence identity with the amino acid or amino acid analogue sequences of embodiments described herein.

Conservative Amino Acid Substitutions

| | |
|---|---|
| Basic: | arginine |
| | lysine |
| | histidine |
| Acidic: | glutamic acid |
| | aspartic acid |
| Uncharged Polar: | glutamine |
| | asparagine |
| | serine |
| | threonine |
| | tyrosine |
| Non-Polar: | phenylalanine |
| | tryptophan |
| | cysteine |
| | glycine |
| | alanine |
| | valine |
| | proline |
| | methionine |
| | leucine |
| | isoleucine |

The table below sets out another scheme of amino acid substitution. Substitution may be either the L- or D-form of amino acid. In some embodiments, the substitution is with the L-form.

| Original Residue | Substitutions |
|---|---|
| Ala | Gly; Ser; Thr |
| Arg | Lys; Gln |
| Asn | Gln; His; Ser |
| Asp | Glu; iminodiacetic acid; Asn |
| Cys | Ser |
| Gln | Asn; Ser; Asp; Glu |
| Glu | Asp; Gln; Lys |
| Gly | Ala; Pro; Asn |
| His | Asn; Gln; Tyr |
| Ile | Leu; Val; Met; Val; Phe |
| Leu | Ile; Val; Met; Phe |
| Lys | Arg; Gln; |
| Met | Leu; Tyr; Ile; norleucine; Val; Phe |
| Pro | Beta homo proline; Ser; Thr; nipecotic acid; isonipecotic acid; Ala; Gly; aminobenzoic acid (m, p, or o); alpha homoproline |
| Phe | Met; Leu; Tyr; Trp |
| Ser | Thr; Gly; Asn; Asp |
| Thr | Ser; Asn |
| Trp | Tyr; Phe,; 1-Napthylalanine; 2-Napthylalanine |
| Tyr | Trp; Phe; Trp |
| Val | Ile; Leu; Met; Phe |

Other variants can consist of less conservative amino acid substitutions, such as selecting residues that differ more significantly in their effect on maintaining a) the structure of the polypeptide backbone in the area of the substitution, for example, as a turn, sheet, extended, or helical conformation, (b) the charge or hydrophobicity of the molecule at the target site, or (c) the bulk of the side chain. The substitutions that in general are expected to have a more significant effect on function are those in which a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine. Other variants include those designed to either generate a novel glycosylation and/or phosphorylation site(s), or those designed to delete an existing glycosylation and/or phosphorylation site(s). Variants include at least one amino acid substitution at a glycosylation site, a proteolytic cleavage site and/or a cysteine residue. Variants also include proteins and peptides with additional amino acid residues before or after the protein or peptide amino acid sequence on linker peptides. The term "variant" also encompasses polypeptides that have the amino acid sequence of the proteins/peptides of the present embodiments with at least one and up to 25 (e.g., 1, 2, 3, 4, 5, 6, 7, 8, 9, 10, 15, 20) additional amino acids flanking either the N-terminal or C-terminal end of the amino acid sequence or both. The residue can also be the L- or D-form. For example for the substitution of proline shown in the table above, the Beta-homo proline, nipecotic acid, or isonipecotic acid can be D or L.

The term "variant" also refers to a protein that is at least 60 to 99 percent identical (e.g., 60, 65, 70, 75, 80, 85, 90, 95, 98, 99, inclusive) in its amino acid sequence of the proteins of the present embodiments described herein as determined by standard methods that are commonly used to compare the similarity in position of the amino acids of two polypeptides. The degree of similarity or identity between two proteins can be readily calculated by known methods. Methods to determine identity are designed to give the largest match between the sequences tested. Methods to determine identity and similarity are codified in publicly available computer programs. Variants will typically have one or more (e.g., 2, 3, 4, 5, etc.) amino acid substitutions, deletions, and/or insertions as compared with the comparison protein or peptide, as the case may be.

Identity and similarity of related polypeptides can be readily calculated by known methods. Such methods include, but are not limited to, those described in Computational Molecular Biology, Lesk, A. M., ed., Oxford University Press, New York (1988); Biocomputing: Informatics and Genome Projects, Smith, D. W., ed., Academic Press, New York (1993); Computer Analysis of Sequence Data, Part 1, Griffin, A. M., and Griffin, H. G., eds., Humana Press, New Jersey (1994); Sequence Analysis in Molecular Biology, von Heinje, G., Academic Press (1987); Sequence Analysis Primer, Gribskov, M. and Devereux, J., eds., M. Stockton Press, New York (1991); and Carillo et al., SIAM J. Applied Math., 48:1073 (1988).

In some embodiments, methods to determine identity and/or similarity are designed to give the largest match between the sequences tested. Methods to determine identity and similarity are described in publicly available computer programs. In some embodiments, computer program methods to determine identity and similarity between two sequences include, but are not limited to, the GCG program package, including GAP (Devereux et al., Nucl. Acid. Res., 12:387 (1984); Genetics Computer Group, University of Wisconsin, Madison, Wis., BLASTP, BLASTN, and FASTA (Altschul et al., J. Mol. Biol., 215:403 410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra (1990)). The well-known Smith-Waterman algorithm may also be used to determine identity. To determine similarity between peptides, BLASTP can be used with default settings taking into account the small size of the peptides.

Certain alignment schemes for aligning two amino acid sequences may result in the matching of only a short region of the two sequences, and this small aligned region may have very high sequence identity even though there is no significant relationship between the two full-length sequences. Accordingly, in some embodiments, the selected alignment method (GAP program) will result in an alignment that spans at least 8, 10, 20, 30, 40, or 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually ¹/₁₀ times the gap opening penalty), as well as a comparison matrix such as PAM 250 or BLOSUM 62 are used in conjunction with the algorithm. A standard comparison matrix (see Dayhoff et al., Atlas of Protein Sequence and Structure, 5(3) (1978) for the PAM 250 comparison matrix; Henikoff et al., Proc. Natl. Acad. Sci USA, 89:10915 10919 (1992) for the BLOSUM 62 comparison matrix) is also used by the algorithm. In some embodiments, parameters for a polypeptide sequence comparison include the following: Algorithm: Needleman et al., J. Mol. Biol., 48:443 453 (1970); Comparison matrix: BLOSUM 62 from Henikoff et al., supra (1992); Gap Penalty: 12 Gap Length Penalty: 4 Threshold of Similarity: 0. The GAP program can be used with the above parameters. The aforementioned parameters are the default parameters for polypeptide comparisons (along with no penalty for end gaps) using the GAP algorithm.

Other exemplary algorithms, gap opening penalties, gap extension penalties, comparison matrices, thresholds of similarity, etc. may be used by those of skill in the art, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally used) or between one sequence and a large database of sequences (in which case FASTA or BLASTA are used).

The compounds of the present embodiments include compounds having one of the general formulas described herein, in addition to derivatives and/or mimetics thereof.

The term "derivative" refers to a chemically modified protein or polypeptide that has been chemically modified either by natural processes, such as processing and other post-translational modifications, but also by chemical modification techniques, as for example, by addition of one or more polyethylene glycol molecules, sugars, phosphates, and/or other such molecules, where the molecule or molecules are not naturally attached to wild-type proteins. Derivatives include salts. Such chemical modifications are well described in basic texts and in more detailed monographs, as well as in a voluminous research literature, and they are well known to those of skill in the art. It will be appreciated that the same type of modification may be present in the same or varying degree at several sites in a given protein or polypeptide. Also, a given protein or polypeptide may contain many types of modifications. Modifications can occur anywhere in a protein or polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. They can also be conjugated to vitamins, such as biotin, folate or vitamin B12. See, for instance, Proteins—Structure And Molecular Properties, 2nd Ed., T. E. Creighton, W. H. Freeman and Company, New York (1993) and Wold, F., "Posttranslational Protein Modifications: Perspectives and Prospects," pgs. 1-12 in Posttranslational Covalent Modification Of Proteins, B. C. Johnson, Ed., Academic Press, New York (1983); Seifter et al., Meth. Enzymol. 182:626-646 (1990) and Rattan et al., "Protein Synthesis: Posttranslational Modifications and Aging," Ann. N.Y. Acad. Sci. 663: 48-62 (1992). The term "derivatives" include chemical modifications resulting in the protein or polypeptide becoming branched or cyclic, with or without branching. Cyclic, branched and branched circular proteins or polypeptides may result from post-translational natural processes and may be made by entirely synthetic methods, as well. In some embodiments, the compounds can be covalently attached to carrier proteins such as serum albumin or other plasma proteins.

The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. Examples of peptide mimetics in this broader sense (where part of a peptide is replaced by a structure lacking peptide bonds) are described below. Whether completely or partially non-peptide, peptide mimetics according to the embodiments provide a spatial arrangement of reactive chemical moieties that closely resemble the three-dimensional arrangement of active groups in the peptide on which the peptide mimetic is based. As a result of this similar active-site geometry, the peptide mimetic has effects on biological systems that are similar to the biological activity of the peptide. The mimetics can also be referred to as the compounds.

In some embodiments, the compound, or a pharmaceutically acceptable salt thereof, has the formula of Formula I:

The alkyl groups of $Z_1$, $Z_2$, and $Z_3$ can each independently be substituted with an electron withdrawing or donating group.

In some embodiments, the effect of the electron withdrawing or donating group is to affect the lability of the bond between the sulfur and $R_1$. In some embodiments, In some embodiments, $R_1$ is —S—$CH_3$, —S—C(=O)$CH_3$, —C(=O)$CH_3$, H, or —$CH_2$—$CH_3$.

In some embodiments, the lability is increased as compared to the bond shown in a compound of Compound 2. In some embodiments, the lability is decreased as compared to the bond shown in a compound of Compound 2. The effects on the lability of the bond between the sulfur and $R_1$ can also have an effect on the activity and/or stability of the compounds. For example, as discussed in the Examples section herein, a compound of Compound 2 is more stable than a compound of Compound 3 even though both bonds are exchangeable. Thus, the presence of different electron donating or withdrawing groups can be used to affect the stability and activity of the compounds. The lability of the bond can be measured using plasma or chemical stability assays, such as those described herein. In some embodiments, the group is halo or haloalkyl.

In some embodiments, $Z_1$ is substituted or unsubstituted methyl, ethyl, butyl, or t-butyl. In some embodiments, $Z_1$ is substituted or unsubstituted $C_1$-$C_4$ alkyl.

In some embodiments, $Z_2$ is substituted or unsubstituted methyl, ethyl, butyl, or t-butyl. In some embodiments, $Z_2$ is substituted or unsubstituted $C_1$-$C_4$ alkyl.

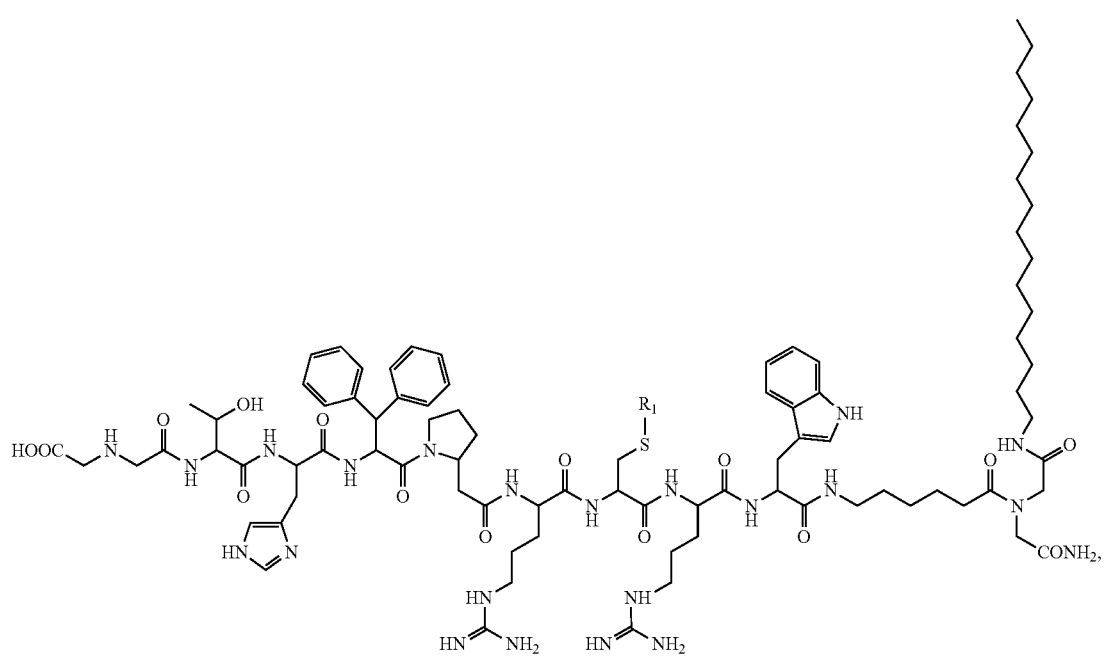

wherein $R_1$ is —S—$Z_1$; —$Z_2$, —SH, —C(=O)—$Z_3$, or —S—C(=O)—$Z_3$,
wherein:
$Z_1$ is substituted or unsubstituted $C_1$-$C_{18}$ alkyl, wherein the $C_1$-$C_{18}$ alkyl is branched or unbranched or $Z_1$ is an electron withdrawing or donating group;
$Z_2$ is substituted or unsubstituted $C_1$-$C_{18}$ alkyl, wherein the $C_1$-$C_{18}$ alkyl is branched or unbranched or $Z_2$ is an electron withdrawing or donating group;
$Z_3$ is substituted or unsubstituted $C_1$-$C_{18}$ alkyl, wherein the $C_1$-$C_{18}$ alkyl is branched or unbranched or $Z_3$ is an electron withdrawing or donating group;

In some embodiments, $Z_3$ is substituted or unsubstituted methyl, ethyl, butyl, or t-butyl. In some embodiments, $Z_3$ is substituted or unsubstituted $C_1$-$C_4$ alkyl.

In some embodiments, $Z_1$, $Z_2$, and $Z_3$ are each, independently, $C_1$-$C_3$, $C_1$-$C_4$, $C_1$-$C_6$, $C_4$-$C_6$, or $C_1$-$C_{10}$ alkyl. In some embodiments, the DPA group shown in Formula I is replaced with a phenylalanine residue. In some embodiments, the bhPro is replaced with a proline residue. In some embodiments, the DPA and bhPro shown in Formula I are replaced with phenylalanine and proline, respectively.

In some embodiments, the compound, or a pharmaceutically acceptable salt thereof, has the formula of:
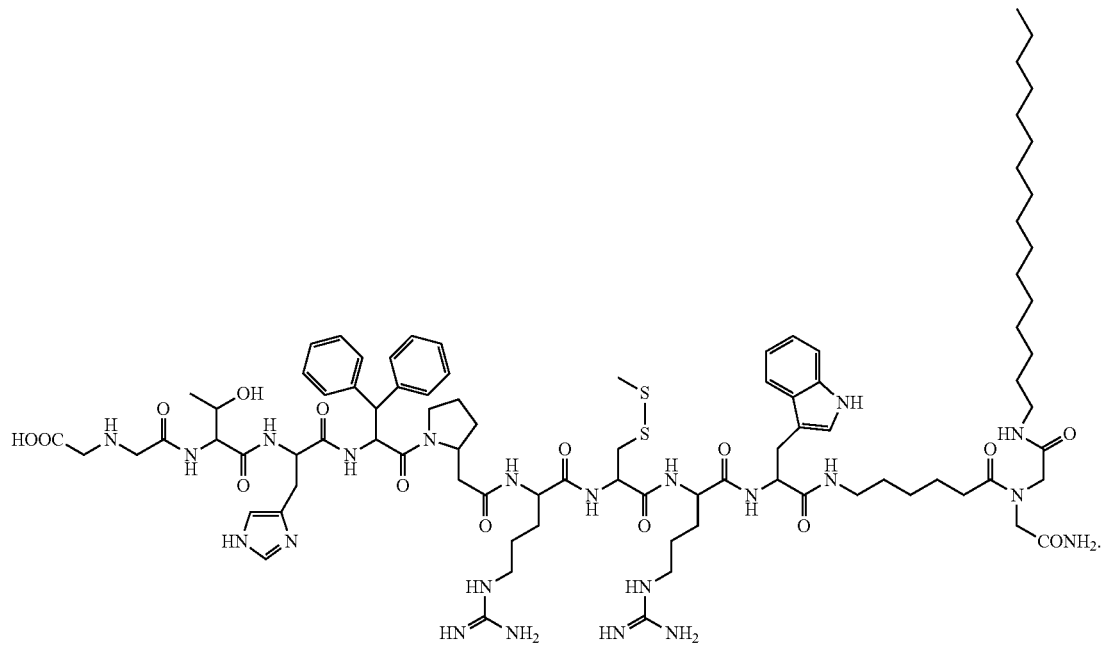
Compound 2
In some embodiments, the compound, or a pharmaceutically acceptable salt thereof, has the formula of:
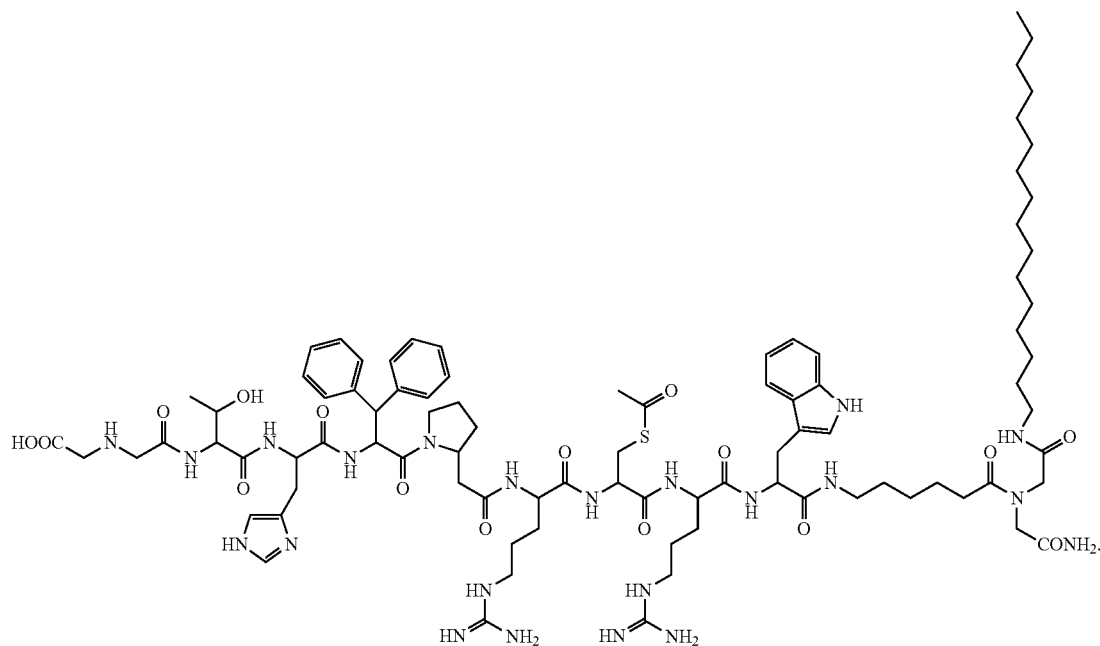
Compound 3

In some embodiments, the compound, or a pharmaceutically acceptable salt thereof, has formula of Compound 4:

Compound 4

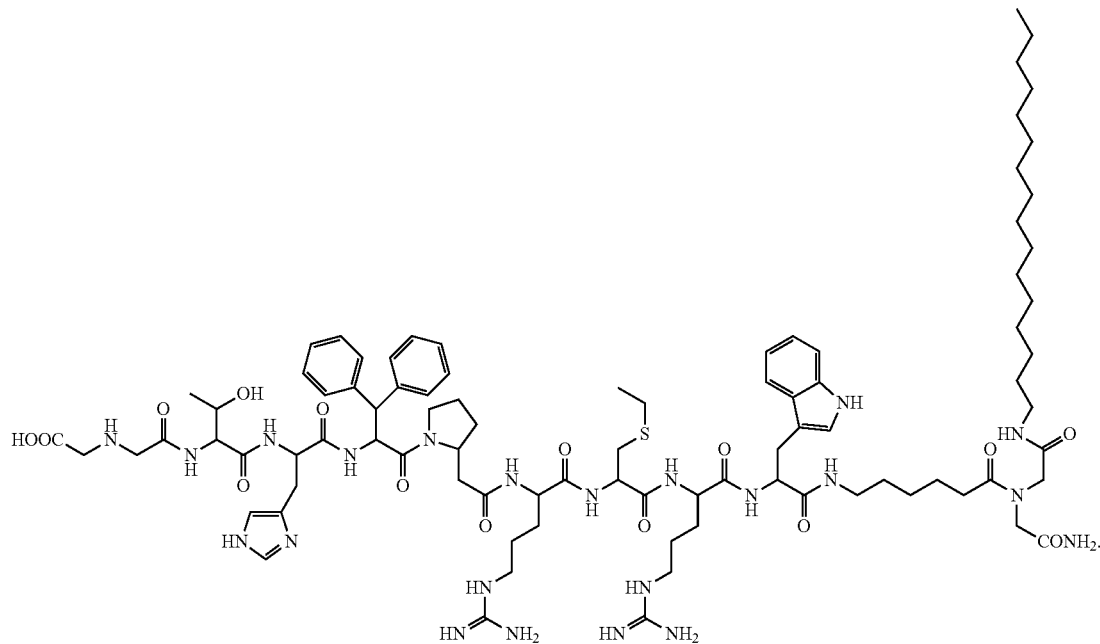

In some embodiments of the compound, or a pharmaceutically acceptable salt thereof, of Formula I, the electron withdrawing group or electron donating group is connected to the sulfur atom through a disulfide bond. In some embodiments, the electron withdrawing group or electron donating group is connected to the sulfur atom through a thioester. In some embodiments, the electron withdrawing group or electron donating group is connected to the sulfur through an irreversible linkage. As used herein, the term "irreversible linkage" refers to a bond that is not cleaved under normal physiological conditions to produce a free sulfhydryl. For example, if $R_1$ were connected to the sulfur through a disulfide bond, the disulfide can be reduced to produce a free sulfhydryl on both the $R_1$ and the molecule shown above. This disulfide bond would not be considered an irreversible linkage. In some embodiments, the compound of Formula I is reduced to produce a free sulfhydryl.

In some embodiments of a compound of Formula I, wherein $R_1$ is —S—$Z_1$; —$Z_2$, —SH, —S—C(=O)—$Z_3$, —C(=O)—$Z_3$ the compound can be converted into a compound, or a pharmaceutically acceptable salt thereof, of Compound 1:

Compound 1

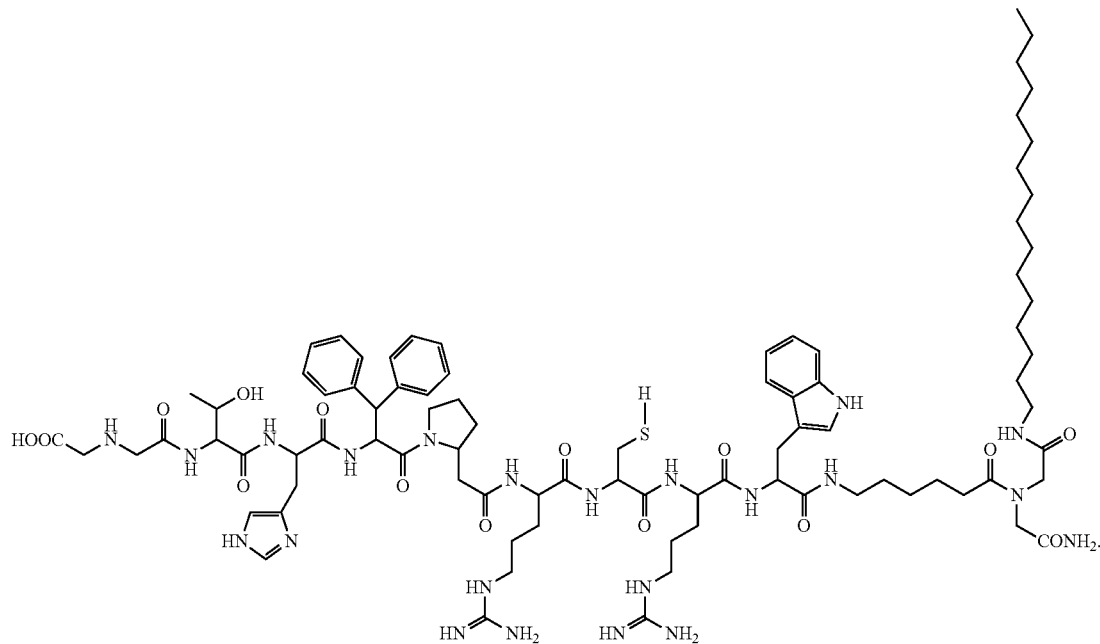

The compounds described herein can be administered or prepared as pharmaceutical compositions to a subject and the compounds can be converted into Compound 1.

In some embodiments, a compound provided herein is not Compound 1, or a pharmaceutically acceptable salt thereof.

In some embodiments, a compound, or a pharmaceutically acceptable salt thereof, of Formula II or III is provided:

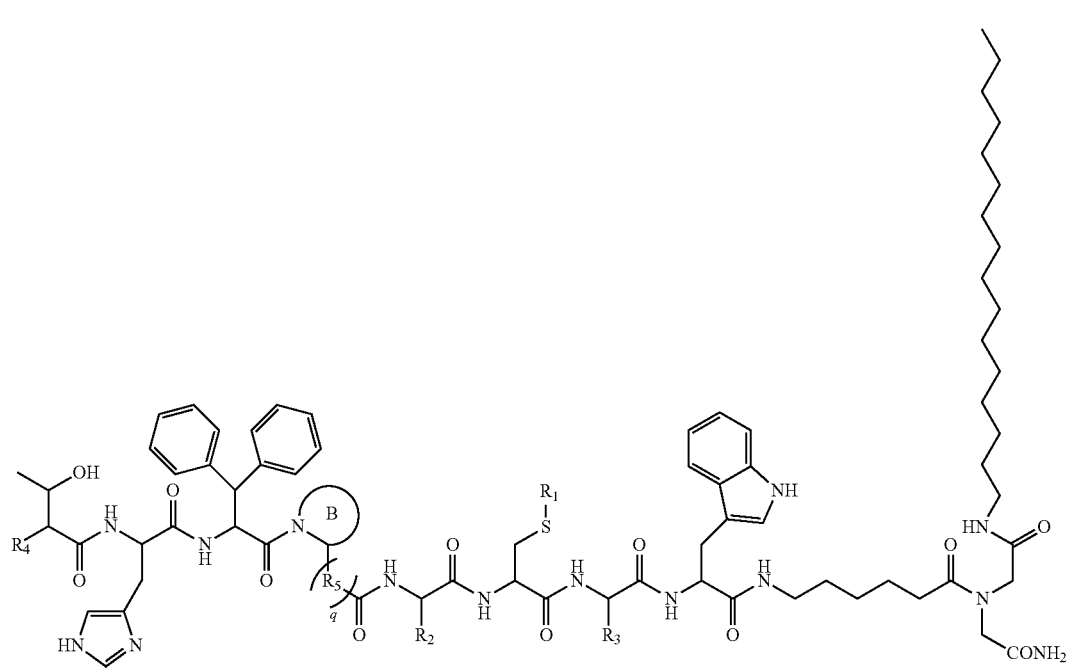

or

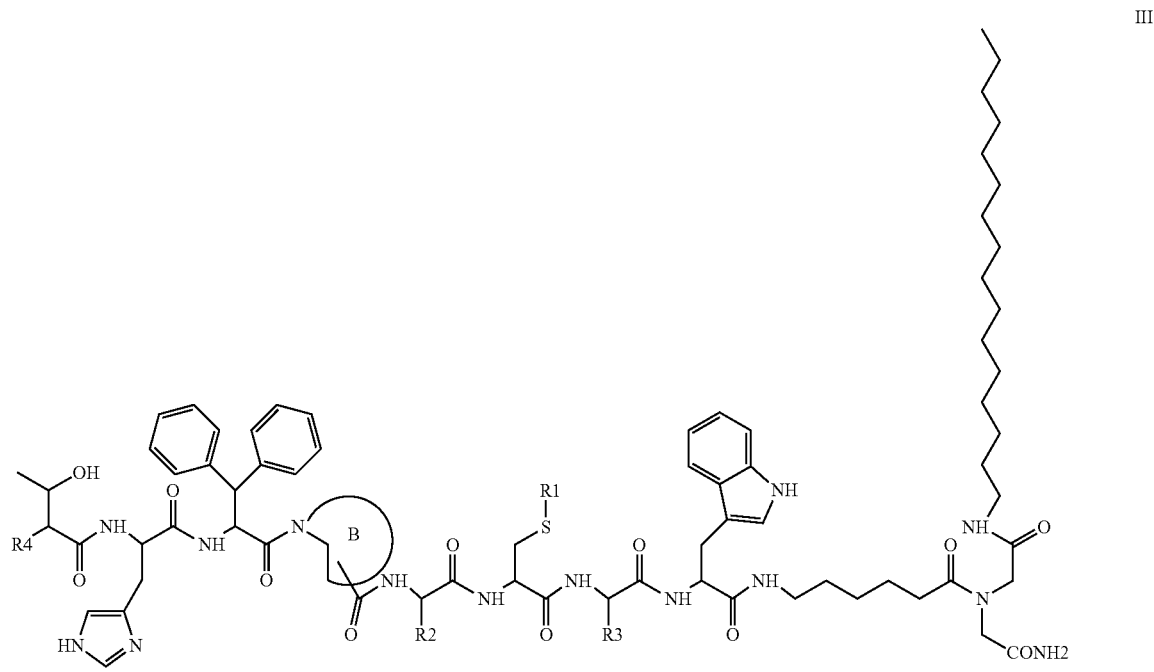

wherein $R_1$ is, H, —S—$Z_1$; —$Z_2$, —SH, —S—C(=O)—$Z_3$, —C(=O)—$Z_3$ $R_2$ and $R_3$ are each, independently, optionally substituted $C_4$-$C_7$ alkyl, D-Arg, D-Ile, Leu, D-Leu, Thr, D-Thr, Lys, D-Lys, Val, D-Val, D-Nω,ω-dimethyl-arginine, L-Nω,ω-dimethyl-arginine, D-homoarginine, L-homoarginine, D-norarginine, L-norarginine, citrulline, a modified Arg wherein the guanidinium group is modified or substituted, norleucine, norvaline, beta homo-Ile, Ach, N-Me-Arg, N-Me-Ile;

$R_4$ is Ida, Asp, Acetyl-Asp, N-MeAsp, Acetyl-Gly-Ida, or Acetyl-Gly-Asp or a derivative thereof to remove its negative charge above pH 4;

$R_5$ is $CR_6R_7$, aryl or heteroaryl;

B is absent or forms a 5-7 membered ring; and provided that when $R_1$ is H, the compound is not a compound of Compound 1.

For the avoidance of doubt, the "C" in $CR_6R_7$, when referenced in regards to $R_5$, is a carbon and not a cysteine residue.

In some embodiments, $R_1$ is —S—$CH_3$, —S—C(=O)$CH_3$, —C(=O)$CH_3$, H, or —$CH_2$—$CH_3$. In some embodiments, a compound of Formula II or III is reduced to produce a free sulfhydryl. For example, where $R_1$ is —S—$CH_3$, the compound can be reduced in vitro or in vivo to where $R_1$ is H. Accordingly, in some embodiments, a compound of Formula II or III can be converted into a compound where $R_1$ is H when the bond with the sulfur is reversible (i.e., exchangeable). In some embodiments, the compounds of Formula II or III can be administered or prepared as pharmaceutical compositions to a subject and the compounds can be converted into compound where $R_1$ is H (reduced sulfhydryl).

As used herein, "B is absent or forms a 5-7 membered ring" refers to the ring portion being absent or present. If the ring is absent, the backbone of peptide bond is still present in the structure. In some embodiments, the nitrogen in the ring formed by B is replaced with a carbon.

For example, if B is absent in Formula II, the compound, or a pharmaceutically acceptable thereof, can be represented as a compound, or a pharmaceutically acceptable thereof, of Formula II-A:

II-A q is 0-6, wherein when $R_5$ aryl or heteroaryl q is 1 and B is absent;

wherein:

$Z_1$ is substituted or unsubstituted $C_1$-$C_{18}$ alkyl, wherein the $C_1$-$C_{18}$ alkyl is branched or unbranched;

$Z_2$ is substituted or unsubstituted $C_1$-$C_{18}$ alkyl, wherein the $C_1$-$C_{18}$ alkyl is branched or unbranched;

$Z_3$ is substituted or unsubstituted $C_1$-$C_{18}$ alkyl, wherein the $C_1$-$C_{18}$ alkyl is branched or unbranched;

$R_6$ and $R_7$ are each, independently, H, halo, optionally substituted $C_1$-$C_3$ alkyl, or haloalkyl, aryl, heteroaryl, or carbocycle.

with the variables as defined above for a compound of Formula II. In some embodiments, a compound of Formula II-A is reduced to produce a free sulfhydryl. For example, where $R_1$ is —S—$CH_3$, the compound can be reduced in vitro or in vivo to where $R_1$ is H. Accordingly, in some embodiments, a compound of Formula II-A can be converted into a compound where $R_1$ is H when the bond with the sulfur is reversible (i.e., exchangeable). In some embodiments, the compounds of Formula II-A can be administered or prepared as pharmaceutical compositions to a subject and the compounds can be converted into compound where $R_1$ is H (reduced sulfhydryl).

In some embodiments, when B is absent in Formula II or III, the compound, or a pharmaceutically acceptable thereof, can be represented as a compound, or a pharmaceutically acceptable thereof, of Formula II-B, II-C, or III-A:
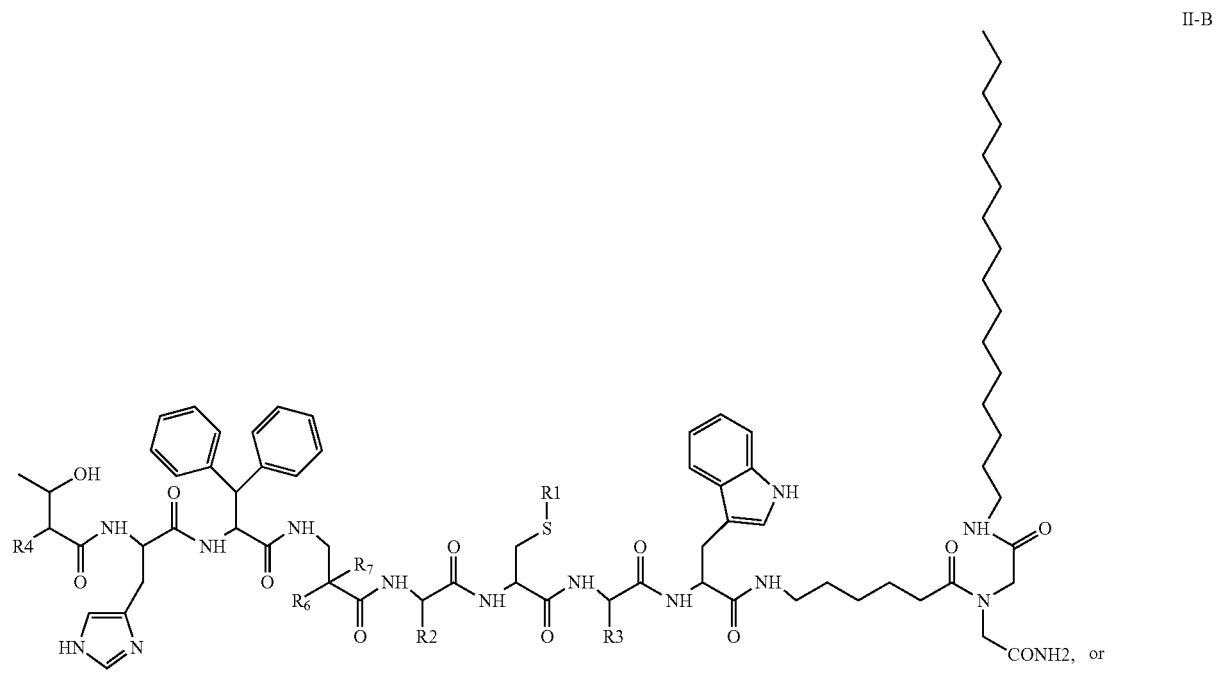
II-B
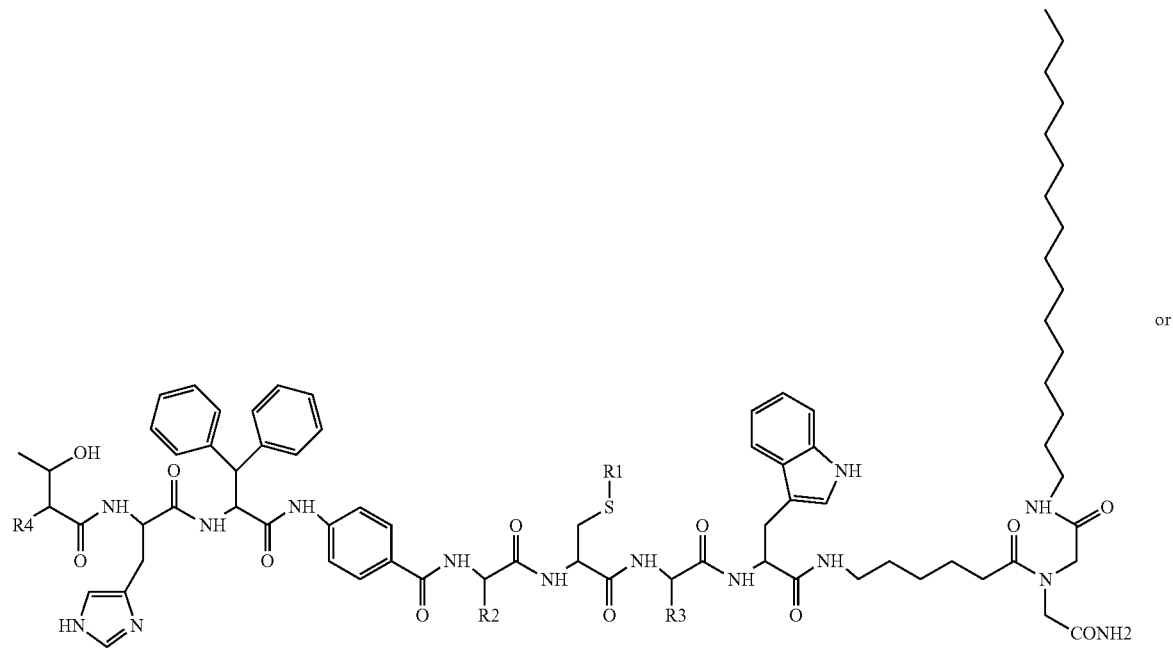
II-C
or

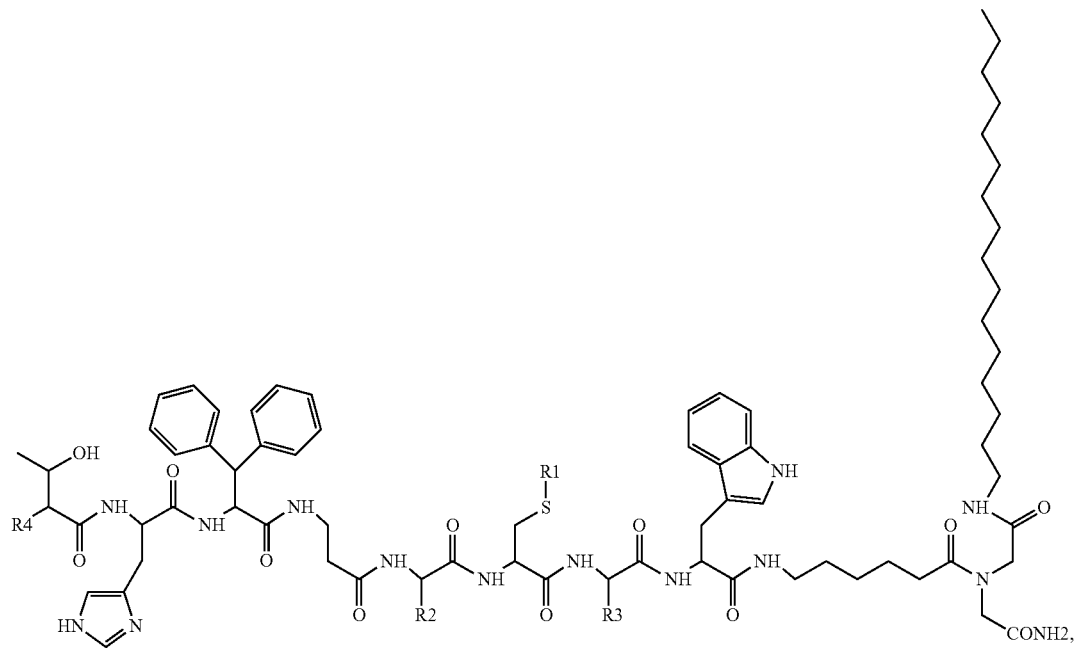

with the variables as defined above for a compound of Formula II and Formula III. Additionally, in some embodiments, the phenyl ring shown in the peptide like backbone chain can be connected in the ortho and meta positions in addition to the para positions that is shown.

In some embodiments, a compound of Formula II-B, II-C, or III-A is reduced to produce a free sulfhydryl. For example, where $R_1$ is —S—$CH_3$, the compound can be reduced in vitro or in vivo to where $R_1$ is H. Accordingly, in some embodiments, a compound of Formula II-B, II-C, or III-A can be converted into a compound where $R_1$ is H when the bond with the sulfur is reversible (i.e., exchangeable). In some embodiments, the compounds of Formula II-B, II-C, or III-A can be administered or prepared as pharmaceutical compositions to a subject and the compounds can be converted into compound where $R_1$ is H (reduced sulfhydryl).

The ring formed can be "R" or "S" or a racemic mixture based upon the starting material to form the ring. In some embodiments, the compound is essentially pure "R" or essentially pure "S" at the position of the B ring. The different enantiomers can be separated and purified using chiral columns. In some embodiments, the compound are prepared as substantially pure forms based upon the starting material. The different enantiomers can be prepared by using D or L forms of the residue at the particular position.

In some embodiments, B is a 5 membered ring. In some embodiments, B is a 6 membered ring. In some embodiments, B is a 7 membered ring. In some embodiments, the peptide backbone includes carbons at positions 2 and 3 of the B ring. In some embodiments, the peptide backbone includes carbons at positions 2 and 4 of the B ring. In some embodiments, the peptide backbone includes carbons at positions 2 and 5 of the B ring. In some embodiments, the peptide backbone includes carbons at positions 2 and 6 of the B ring.

In some embodiments, B forms a pyrrolidine, piperidine, azepane ring with the N and C to which it is attached. In some embodiments, the ring formed by B is a heterocycle, aromatic, heteroaromatic, or carbocyclic. When it is carbocyclic the nitrogen is replaced with a carbon. The heterocycle can have more than 1 heteroatom. In some embodiments, the heterocycle has 2 or 3 heteroatoms, which includes the nitrogen in the backbone of the molecule.

In some embodiments, $R_6$ and $R_7$ are H. In some embodiments, $R_6$ is H and $R_7$ is halo, optionally substituted $C_1$-$C_3$ alkyl, or haloalkyl. In some embodiments, $R_6$ is H and $R_7$ is aryl. In some embodiments, the aryl is phenyl. In some embodiments, the aryl is a heteroaryl. In some embodiments, the aryl is one of the examples of aryl groups described herein. In some embodiments, $R_6$ is H and $R_7$ is carbocyle, such as but not limited to, cyclopropyl, cyclobutyl, cyclopentyl, cyclohexyl, and cyclopentyl. In some embodiments, $R_6$ is H and $R_7$ is a heterocycle. In some embodiments, when q is 2-6, each occurrence of $R_5$ is different. For example if q is 2, one $R_5$ could be $CH_2$, i.e. $R_6$ and $R_7$ are both H, while the second occurrence of $R_5$ could be $CHCH_3$, i.e. $R_6$ is H and $R_7$ is $CH_3$. In some embodiments, each occurrence of $R_5$ is the same. In some embodiments, each occurrence of $R_5$ is independent of the other. This allows one to build in rotational constraints when q is 2-6 by modifying the substitutions of $R_5$. In some embodiments, when $R_5$ is aryl or heteroaryl, $R_5$ is phenyl.

In some embodiments, the compound, or a pharmaceutically acceptable salt thereof of Formula III is a compound, or a pharmaceutically acceptable salt thereof of Formula IV:

IV

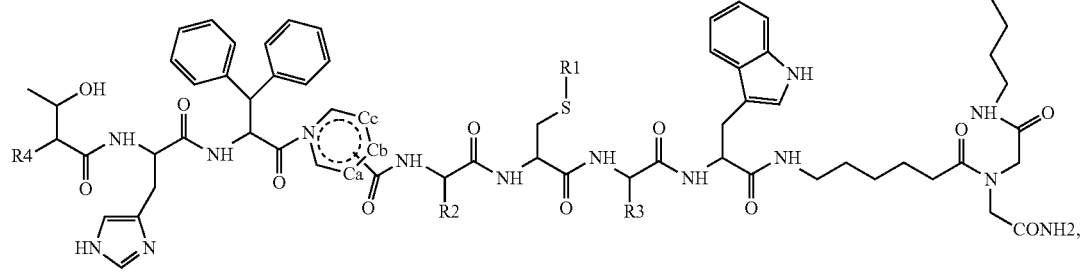

wherein the bond from the carbonyl forms a bond with the 6 membered ring at $C_a$, $C_b$, or $C_c$ (the bond can be a D-form or L-form at this position) and with the variables of $R_1$, $R_2$, $R_3$, and $R_4$ as defined above for a compound of Formula III. The atoms at $C_a$, $C_b$, or $C_c$ are carbons. In some embodiments, the carbonyl forms a bond with the 6-membered ring at $C_a$. In some embodiments, the carbonyl forms a bond with the 6-membered ring at $C_b$. In some embodiments, the carbonyl forms a bond with the 6-membered ring at $C_c$. In some embodiments the 6-membered ring is partially saturated or aromatic. In some embodiments, 6-membered ring is completely saturated. In some embodiments, one or more of the carbons at $C_a$, $C_b$ and $C_c$ is replaced with N or O. In some embodiments, the carbon at $C_a$ is replaced with N or O and $C_b$ and $C_c$ remain carbon. In some embodiments, the carbon at $C_b$ is replaced with N or O and $C_a$ and $C_c$ remain carbon. In some embodiments, the carbon at $C_c$ is replaced with N or O and $C_a$ and $C_b$ remain carbon. In some embodiments, a compound of Formula IV is a compound of Compound 5 or 6 as shown herein. In some embodiments, the nitrogen shown in the ring that includes $C_a$, $C_b$, or $C_c$ is replaced with a carbon.

In some embodiments, a compound of Formula IV is reduced to produce a free sulfhydryl. For example, where $R_1$ is —S—$CH_3$, the compound can be reduced in vitro or in vivo to where $R_1$ is H. Accordingly, in some embodiments, a compound of Formula IV can be converted into a compound where $R_1$ is H when the bond with the sulfur is reversible (i.e., exchangeable). In some embodiments, the compounds of Formula IV can be administered or prepared as pharmaceutical compositions to a subject and the compounds can be converted into compound where $R_1$ is H (reduced sulfhydryl).

In some embodiments, the compound, or a pharmaceutically acceptable thereof, of Formula III is a compound, or a pharmaceutically acceptable thereof, of Formula V

V

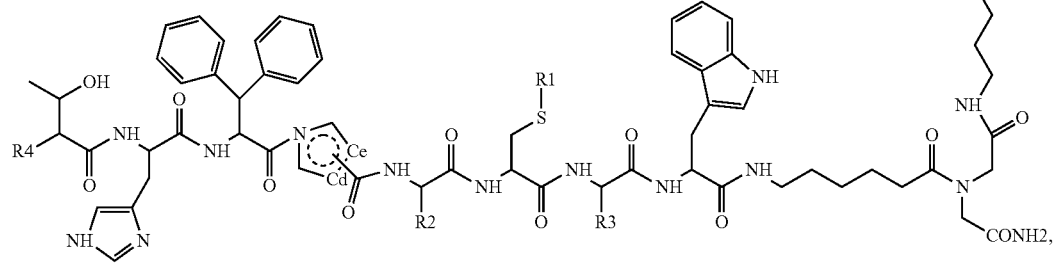

wherein the bond from the carbonyl forms a bond with the 5 membered ring at $C_d$ or $C_e$ (the bond can be a D-form or L-form at this position) and with the variables of $R_1$, $R_2$, $R_3$, and $R_4$ as defined above for a compound of Formula III. The atoms at $C_d$ and $C_e$ are carbons. In some embodiments the 5-membered ring is partially saturated or aromatic. In some embodiments, 5-membered ring is completely saturated. In some embodiments, one or both of the carbons at $C_d$, and $C_e$ is replaced with N or O. In some embodiments, the carbon at $C_d$ is replaced with N or O and $C_e$ remains carbon. In some embodiments, the carbon at $C_e$ is replaced with N or O and $C_d$ remains carbon.

In some embodiments, a compound of Formula V is reduced to produce a free sulfhydryl. For example, where $R_1$ is —S—$CH_3$, the compound can be reduced in vitro or in vivo to where $R_1$ is H. Accordingly, in some embodiments, a compound of Formula IV can be converted into a compound where $R_1$ is H when the bond with the sulfur is reversible (i.e., exchangeable). In some embodiments, the compounds of Formula V can be administered or prepared as pharmaceutical compositions to a subject and the compounds can be converted into compound where $R_1$ is H (reduced sulfhydryl).

In some embodiments, the compound, or a pharmaceutically acceptable thereof, is a compound, or a pharmaceutically acceptable thereof, of Formula VI

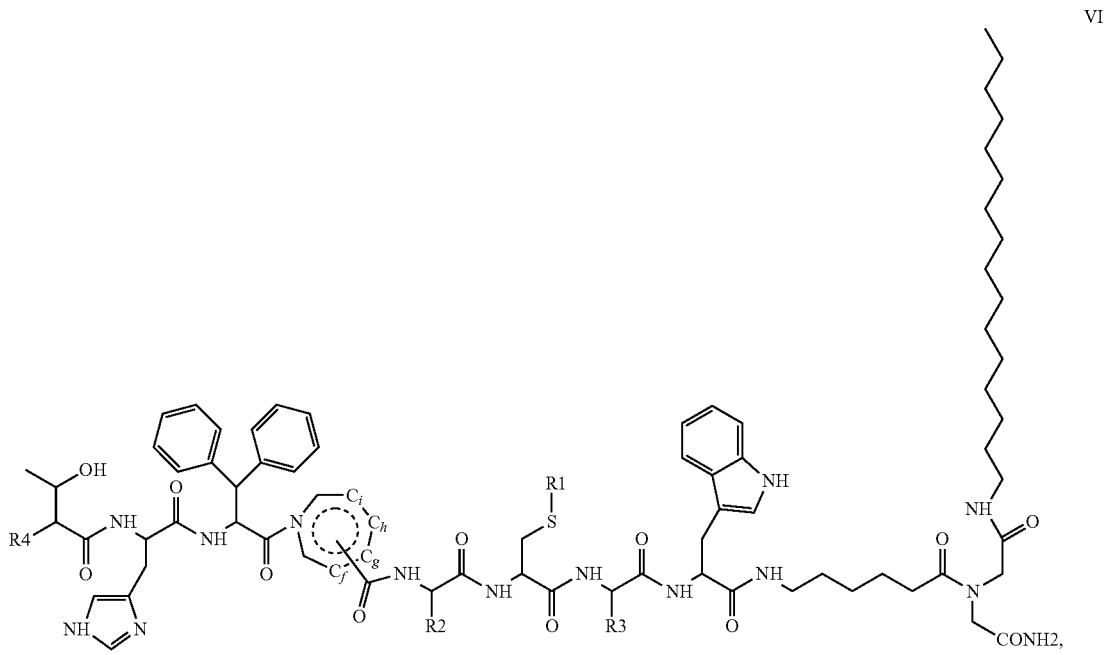

VI wherein the bond from the carbonyl forms a bond with the 7 membered ring at $C_f$, $C_g$, $C_h$, or $C_i$, (this can be a D-form or L-form at this position) and with the variables of $R_1$, $R_2$, $R_3$, and $R_4$ as defined above for a compound of Formula III. In some embodiments, the bond from the carbonyl forms a bond with $C_f$. The atoms at $C_f$, $C_g$, $C_h$, or $C_i$ are carbons. In some embodiments the 7-membered ring is partially saturated or aromatic. In some embodiments, 7-membered ring is completely saturated. In some embodiments, one or more of the carbons at $C_f$, $C_g$, $C_h$, or $C_i$ is replaced with N or O. In some embodiments, one of the carbons at $C_f$, $C_g$, $C_h$, or $C_i$ is replaced with N or O. In some embodiments, two of the carbons at $C_f$, $C_g$, $C_h$, or $C_i$ is replaced with N or O. In some embodiments, the carbon at $C_f$ is replaced with N or O and $C_g$, $C_h$, or $C_i$ remain carbon.

In some embodiments, the compound, or a pharmaceutically acceptable thereof, is a compound, or a pharmaceutically acceptable thereof, of Formula VI-A

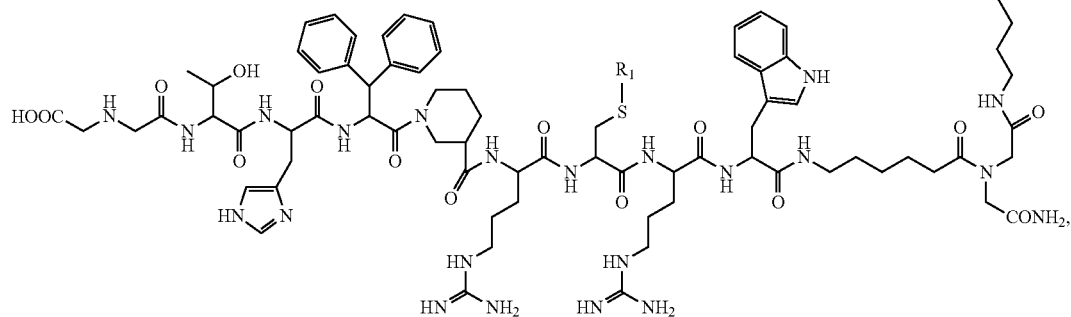

wherein $R_1$ is, H, —S—$Z_1$; —$Z_2$, —SH, —C(=O)—$Z_3$, or —S—C(=O)—$Z_3$, $R_2$ and $R_3$ are each, independently, optionally substituted $C_4$-$C_7$ alkyl,

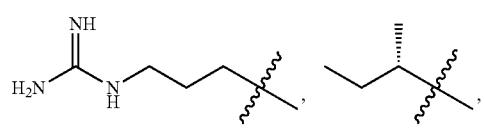

D-Arg, D-Ile, Leu, D-Leu, Thr, D-Thr, Lys, D-Lys, Val, D-Val, D-Nω,ω-dimethyl-arginine, L-Nω,ω-dimethyl-arginine, D-homoarginine, L-homoarginine, D-norarginine, L-norarginine, citrulline, a modified Arg wherein the guanidinium group is modified or substituted, nor-leucine, norvaline, beta homo-Ile, Ach, N-MeArg, N-MeIle, wherein:

$Z_1$ is substituted or unsubstituted $C_1$-$C_{18}$ alkyl, wherein the $C_1$-$C_{18}$ alkyl is branched or unbranched;

$Z_2$ is substituted or unsubstituted $C_1$-$C_{18}$ alkyl, wherein the $C_1$-$C_{18}$ alkyl is branched or unbranched;

$Z_3$ is substituted or unsubstituted $C_1$-$C_{18}$ alkyl, wherein the $C_1$-$C_{18}$ alkyl is branched or unbranched.

In some embodiments, $R_1$ is —S—$CH_3$, —S—C(=O)$CH_3$, —C(=O)$CH_3$, H, or —$CH_2$—$CH_3$.

In some embodiments, the disulfide or bond formed by $R_1$ is reduced to H. In some embodiments, a compound of Formula VI-A is reduced to produce a free sulfhydryl. For example, where $R_1$ is —S—$CH_3$, the compound can be reduced in vitro or in vivo to where $R_1$ is H. Accordingly, in some embodiments, a compound of Formula VI-A can be converted into a compound where $R_1$ is H when the bond with the sulfur is reversible (i.e., exchangeable). In some embodiments, the compounds of Formula VI-A can be administered or prepared as pharmaceutical compositions to a subject and the compounds can be converted into compound where $R_1$ is H (reduced sulfhydryl).

In some embodiments, the compound, or a pharmaceutically acceptable thereof, is a compound, or a pharmaceutically acceptable thereof, of Compound 6.

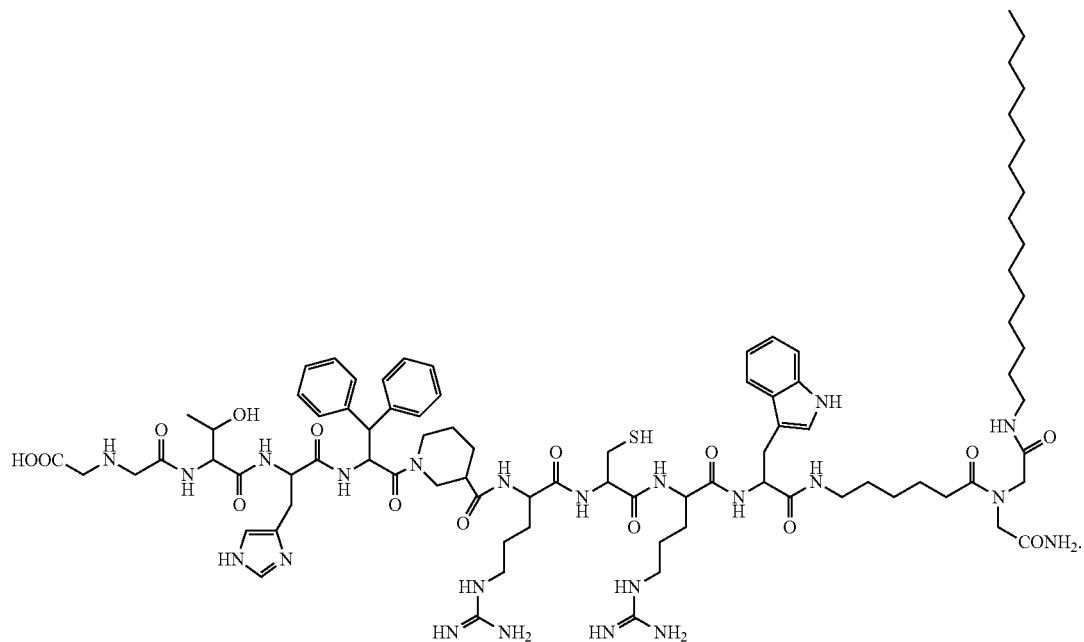

Compound 6

In some embodiments, $R_2$ and $R_3$ are

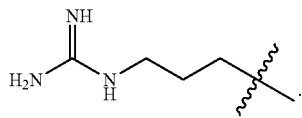

In some embodiments, $R_2$ and $R_3$ are

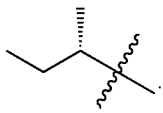 [SMILES: *[C@@H](C)CC]

In some embodiments, one of $R_2$ and $R_3$ is

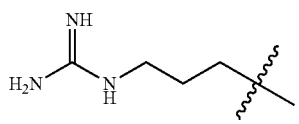 [SMILES: *CCCNC(=N)N]

and the other is

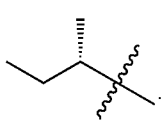 [SMILES: *[C@@H](C)CC]

In some embodiments of the compounds and formulas described herein, $R_4$ is Ida or a derivative thereof to remove its negative charge above pH 4. In some embodiments, $R_4$ is Asp, Acetyl-Asp, N-MeAsp, Acetyl-Gly-Ida, or Acetyl-Gly-Asp, or a derivative thereof to remove its negative charge above pH 4. In some embodiments, the side chain carboxyl group of $R_4$ is modified to remove its negative charge above pH 4. In some embodiments, the side chain carboxyl group is covalently bonded to a glycine residue to form N-acetyl glycine.

In some embodiments, $R_2$ and $R_3$ are

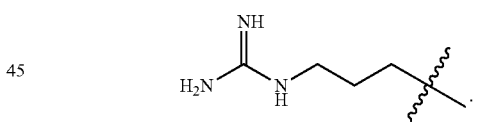

In some embodiments,

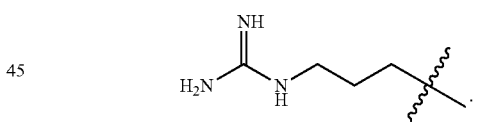

is modified to reduce the charge. The modifications described herein to produce derivatives that do not have a negative charge above pH4 at $R_4$ are for example only and other suitable modifications can be used.

In some embodiments of the compounds and formulas described herein, q is 0, 1, 2, 3, 4, 5, or 6. In some embodiments, q is 0 to 2. In some embodiments q is 1 or 2.

In some embodiments, the compound, or a pharmaceutically acceptable thereof, is a compound, or a pharmaceutically acceptable salts thereof, of Compound 5:

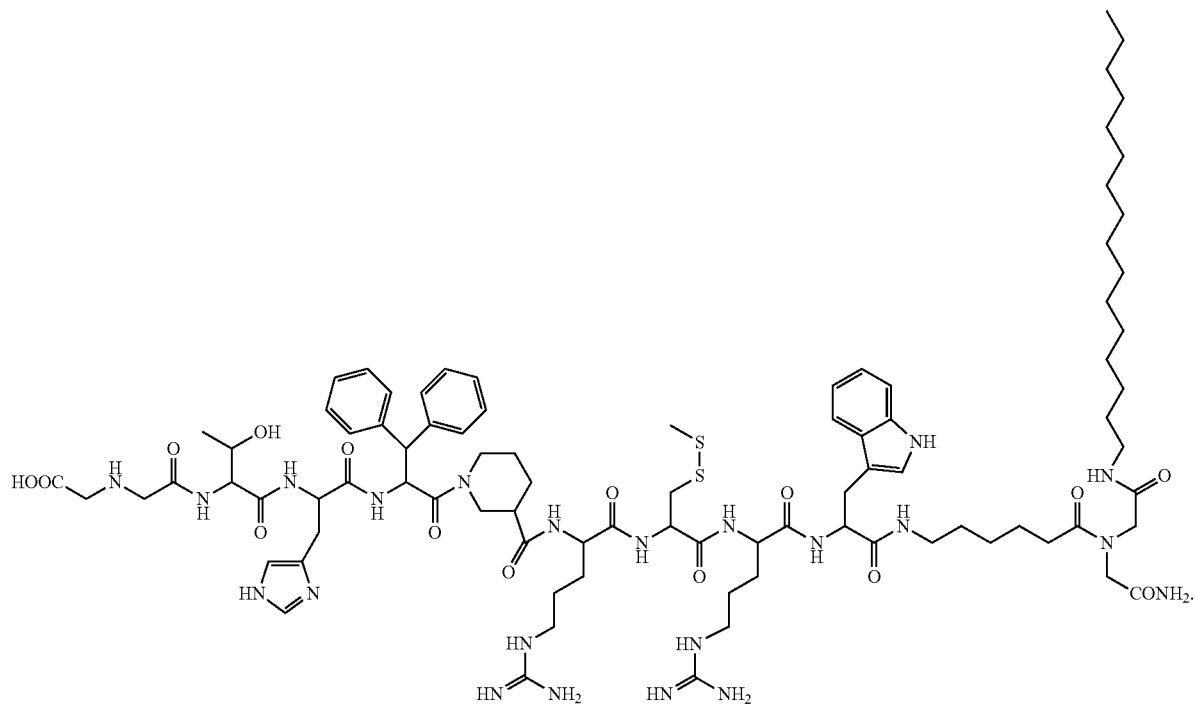

Compound 5

In some embodiments, the compound, or a pharmaceutically acceptable thereof, of Compound 5 is reduced to a compound, or a pharmaceutically acceptable thereof, of Compound 6. In some embodiments, upon administration a compound, as described herein, of a compound of Formula II is administered when $R_1$ is not H, the compound is reduced to a compound where $R_1$ is H, provided that the compound is not a compound of Compound 1.

The compounds described herein can be prepared according to the methods described herein by modifying the materials to yield the desired compound. Embodiments of such methods are described herein.

Although the compounds described herein can be represented by the formula shown herein, in some embodiments, the compounds can also be represented in form of the formula $P_1$-$P_2$-$P_3$-$P_4$-$P_5$-$P_6$-$P_7$-$P_8$-$P_9$-$P_{10}$, wherein the variables are as defined in the following table:

clarity, the —S—$CH_3$, —$CH_2$—$CH_3$, and —C(=O)$CH_3$ are bonded to the S atom in the cysteine and are not part of the peptide-like backbone. Examples of this attachment can be seen in the chemical formula shown herein, such as the formula of Compounds 2-5. Accordingly, in some compounds a compound, or a pharmaceutically acceptable salt thereof, of Compound 7, 8, 9, or 10 are provided. In some compounds a compound, or a pharmaceutically acceptable salt thereof, of Compound 2, 3, 4, 5, or 6 are provided. In some embodiments, the compound, or a pharmaceutically acceptable salt thereof, is not Compound 1. The compounds can also be produced in the reverse order of $P_{10}$-$P_9$-$P_8$-$P_7$-$P_6$-$P_5$-$P_4$-$P_3$-$P_2$-$P_1$. In some embodiments, the compound is composed all or in part of D-amino acids.

Many of the compounds described herein are shown with a aminohexanoic acid linker. This linker can be substituted with

| Compound # | $P_1$ | $P_2$ | $P_3$ | $P_4$ | $P_5$ | $P_6$ | $P_7$ | $P_8$ | $P_9$ | $P_{10}$ |
|---|---|---|---|---|---|---|---|---|---|---|
| 1 (SEQ ID NO: 1) | Ida | Thr | His | Dpa | bhPro | Arg | Cys | Arg | Trp | $X_3$ |
| 2 (SEQ ID NO: 2) | Ida | Thr | His | Dpa | bhPro | Arg | Cys-S—$CH_3$ | Arg | Trp | $X_3$ |
| 3 (SEQ ID NO: 3) | Ida | Thr | His | Dpa | bhPro | Arg | Cys-C(=O)$CH_3$ | Arg | Trp | $X_3$ |
| 4 (SEQ ID NO: 4) | Ida | Thr | His | Dpa | bhPro | Arg | Cys-$CH_2$—$CH_3$ | Arg | Trp | $X_3$ |
| 5 (SEQ ID NO: 5) | Ida | Thr | His | Dpa | Npc | Arg | Cys-S—$CH_3$ | Arg | Trp | $X_3$ |
| 6 (SEQ ID NO: 6) | Ida | Thr | His | Dpa | Npc | Arg | Cys | Arg | Trp | $X_3$ |
| 7 (SEQ ID NO: 7) | Ida | Thr | His | Dpa | D-Npc | Arg | Cys-S—$CH_3$ | Arg | Trp | $X_3$ |
| 8 (SEQ ID NO: 8) | Ida | Thr | His | Dpa | isoNpc | Arg | Cys-S—$CH_3$ | Arg | Trp | $X_3$ |
| 9 (SEQ ID NO: 9) | Acetyl-Gly-Ida | Thr | His | Dpa | bhPro | Arg | Cys-S—$CH_3$ | Arg | Trp | $X_3$ |
| 10 (SEQ ID NO: 10) | Ida | Thr | His | Dpa | bAla | Arg | Cys-S—$CH_3$ | Arg | Trp | $X_3$ | wherein $X_3$ is Ahx-Ida(NH-PAL)-$NH_2$, Ida is Iminodiacetic acid; bhPro is beta-homoproline, Npc is L-nipecotic acid; isoNpc is isonipecotic acid and bAla is beta-alanine. In the table above, $P_7$ is shown in some embodiments as Cys-S—$CH_3$, Cys-$CH_2$—$CH_3$, and Cys-C(=O)$CH_3$. For the sake of a straight or branched alkyl chain or other linker, such as but not limited to PEG or polyglycine.

Additionally, in some embodiments, the palmitoyl carbon chain shown in the structures can replaced with other carbon chains. The compounds represented herein by the various formula show a chain of 16 carbons that are fully saturated. The carbon chain can be increased by 1-10 carbons or decreased by 1-10 carbons. The carbon chain can also be unsaturated and can comprise one or more double bonds. In some embodiments, the carbon chain is 8-24, 10-24, 12-24, 14-24, 16-24, 18-24, 20-24, 22-24, 8-22, 10-22, 12-22, 14-22, 16-22, 18-22, 20-22, 8-20, 10-20, 12-20, 14-20, 16-20, 18-20, 8-18, 10-18, 12-18, 14-18, 16-18, 8-16, 10-16, 12-16, 14-16, 8-14, 10-14, or 12-14 carbons. In some embodiments, the carbon chain has 8, 10, 12, 14, 16, 18, 20, or 24 carbon atoms. In some embodiments, the carbon chain is completely saturated. In some embodiments, the chain is unsaturated. In some embodiments, the carbon chain has alternating double bonds. In some embodiments, the carbon chain is replaced with a vitamin E and analogues thereof, such as but not limited to vitamin E succinate.

The compounds, or pharmaceutically acceptable salts thereof, described herein can also be prepared as pharmaceutical compositions as described herein and used in the methods described herein. In some embodiments, the pharmaceutical composition is free, or substantially free, of Compound 1, or a pharmaceutically acceptable salt thereof. In some embodiments, a pharmaceutical composition comprises Compound 2, or a pharmaceutically acceptable salt thereof, and is substantially free of Compound 1, or a pharmaceutically acceptable salt thereof. In some embodiments, the pharmaceutical composition comprises Compound 2, or a pharmaceutically acceptable salt thereof, as the only active ingredient. In some embodiments, the pharmaceutical composition contains less than 10%, 9%, 8%, 7%, 6%, 5%, 4%, 3%, 2%, 1%, 0.5%, 0.1% of Compound 1, or a pharmaceutically acceptable salt thereof. The percent can be in relation to the total weight of the pharmaceutical composition (e.g. dosage form) or in relation to the total of active ingredient. As described herein, compounds, or pharmaceutically acceptable salts thereof, can be reduced to the free sulfhydryl form. As such, in some embodiments, the pharmaceutical composition is free of the reduced sulfhydryl form of the compound, or a pharmaceutically acceptable salt thereof. In some embodiments, the pharmaceutical composition is substantially free, of the reduced sulfhydryl form of the compound, or a pharmaceutically acceptable salt thereof. In some embodiments, the pharmaceutical composition contains less than, or about, 10%, 9%, 8%, 7%, 6%, 5%, 4%, 3%, 2%, 1%, 0.5%, 0.1% of the reduced sulfhydryl form of the compound, or a pharmaceutically acceptable salt thereof. The percent can be in relation to the total weight of the pharmaceutical composition (e.g. dosage form) or in relation to the total weight of active ingredient.

In some embodiments, the compounds can be prepared as pharmaceutical compositions. Pharmaceutical compositions for use in the embodiments described herein can be formulated by standard techniques using one or more physiologically acceptable carriers or excipients. In some embodiments, the formulations may contain a buffer and/or a preservative. The compounds and their physiologically acceptable salts and solvates can be formulated for administration by any suitable route, including via inhalation, topically, nasally, orally, parenterally (e.g., intravenously, intraperitoneally, intravesically or intrathecally) or rectally in a vehicle comprising one or more pharmaceutically acceptable carriers, the proportion of which is determined by the solubility and chemical nature of the peptide, chosen route of administration and standard biological practice.

According to some embodiments, pharmaceutical compositions are provided comprising effective amounts of one or more compound(s) described herein together with, for example, pharmaceutically acceptable diluents, preservatives, solubilizers, emulsifiers, adjuvants and/or other carriers. Such compositions include diluents of various buffer content (e.g., TRIS or other amines, carbonates, phosphates, amino acids, for example, glycinamide hydrochloride (especially in the physiological pH range), N-glycylglycine, sodium or potassium phosphate (dibasic, tribasic), etc. or TRIS-HCl or acetate), pH and ionic strength; additives such as ionic and non-ionic detergents and solubilizing agents (e.g., surfactants such as Pluronics, Tween 20, Tween 80 (Polysorbate 80), Cremophor, polyols such as polyethylene glycol, propylene glycol, etc.), anti-oxidants (e.g., ascorbic acid, sodium metabisulfite), preservatives (e.g., Thimersol, benzyl alcohol, parabens, etc.) and bulking substances (e.g., sugars such as sucrose, lactose, mannitol, trehalose, polymers such as polyvinylpyrrolidones or dextran, etc.); and/or incorporation of the material into particulate preparations of polymeric compounds such as polylactic acid, polyglycolic acid, etc. or into liposomes or micelles or vesicles. Hyaluronic acid may also be used. Such compositions can be employed to influence the physical state, stability, rate of in vivo release, and rate of in vivo clearance of a compound described herein. See, e.g., Remington's Pharmaceutical Sciences, 18th Ed. (1990, Mack Publishing Co., Easton, Pa. 18042) pages 1435-1712 which are herein incorporated by reference. The compositions can, for example, be prepared in liquid form, or can be in dried powder, such as lyophilized form. Particular methods of administering such compositions are described infra.

Where a buffer is to be included in the formulations, the buffer is selected from the group consisting of sodium acetate, sodium carbonate, citrate, glycylglycine, histidine, glycine, lysine, arginine, aspartate, glutamate, lactate, sodium dihydrogen phosphate, disodium hydrogen phosphate, sodium phosphate, and tris(hydroxymethyl)-aminomethan, or mixtures thereof. Each one of these specific buffers constitutes an alternative embodiment. In some embodiments, the buffer is glycylglycine, sodium dihydrogen phosphate, disodium hydrogen phosphate, sodium phosphate or mixtures thereof.

Where a pharmaceutically acceptable preservative is to be included in the formulations, the preservative is selected from the group consisting of phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof. Each one of these specific preservatives constitutes an alternative embodiment. In some embodiments, the preservative is phenol or m-cresol.

In some embodiments, the preservative is present in a concentration from about 0.1 mg/ml to about 50 mg/ml, in a concentration from about 0.1 mg/ml to about 25 mg/ml, or in a concentration from about 0.1 mg/ml to about 10 mg/ml.

The use of a preservative in pharmaceutical compositions is well-known to the skilled person. For convenience reference is made to Remington: The Science and Practice of Pharmacy, 19th edition, 1995.

In some embodiments, the formulation may further comprise a chelating agent where the chelating agent may be selected from salts of ethylenediaminetetraacetic acid (EDTA), histidine, citric acid, and aspartic acid, and mixtures thereof. Each one of these specific chelating agents constitutes an alternative embodiment.

In some embodiments, the chelating agent is present in a concentration from 0.1 mg/ml to 5 mg/ml. In some embodiments, the chelating agent is present in a concentration from 0.1 mg/ml to 2 mg/ml. In some embodiments, the chelating agent is present in a concentration from 2 mg/ml to 5 mg/ml. The use of a chelating agent in pharmaceutical compositions is well-known to the skilled person. For convenience reference is made to Remington: The Science and Practice of Pharmacy, 19th edition, 1995.

In some embodiments, the formulation may further comprise a stabilizer selected from the group of high molecular weight polymers or low molecular compounds where such stabilizers include, but are not limited to, polyethylene glycol (e.g. PEG 3350), polyvinylalcohol (PVA), polyvinylpyrrolidone, carboxymethylcellulose, different salts (e.g. sodium chloride), L-glycine, L-histidine, imidazole, arginine, lysine, isoleucine, aspartic acid, tryptophan, threonine thioglycerol, methionine, N-acetylcysteine, and mixtures thereof. Each one of these specific stabilizers constitutes an alternative embodiment. In some embodiments, the stabilizer is selected from the group consisting of L-histidine, imidazole and arginine.

In some embodiments, the high molecular weight polymer is present in a concentration from 0.1 mg/ml to 100 mg/ml. In some embodiments, the high molecular weight polymer is present in a concentration from 0.1 mg/ml to 5 mg/ml. In some embodiments, the high molecular weight polymer is present in a concentration from 5 mg/ml to 10 mg/ml. In some embodiments, the high molecular weight polymer is present in a concentration from 10 mg/ml to 20 mg/ml. In some embodiments, the high molecular weight polymer is present in a concentration from 20 mg/ml to 30 mg/ml. In some embodiments, the high molecular weight polymer is present in a concentration from 30 mg/ml to 50 mg/ml.

In some embodiments, the low molecular weight compound is present in a concentration from about 0.1 mg/ml to 100 mg/ml. In some embodiments, the low molecular weight compound is present in a concentration from about 0.1 mg/ml to 5 mg/ml. In some embodiments, the low molecular weight compound is present in a concentration from 5 mg/ml to 10 mg/ml. In some embodiments, the low molecular weight compound is present in a concentration from 10 mg/ml to 20 mg/ml. In some embodiments, the low molecular weight compound is present in a concentration from 20 mg/ml to 30 mg/ml. In some embodiments, the low molecular weight compound is present in a concentration from 30 mg/ml to 50 mg/ml.

The use of a stabilizer in pharmaceutical compositions is well-known to the skilled person. For convenience reference is made to Remington: The Science and Practice of Pharmacy, 19th edition, 1995.

In some embodiments, the formulation may further comprise a surfactant where a surfactant may be selected from a detergent, ethoxylated castor oil, polyglycolyzed glycerides, acetylated monoglycerides, sorbitan fatty acid esters, poloxamers, such as 188 and 407, polyoxyethylene sorbitan fatty acid esters, polyoxyethylene derivatives such as alkylated and alkoxylated derivatives (tweens, e.g. Tween-20, or Tween-80), monoglycerides or ethoxylated derivatives thereof, diglycerides or polyoxyethylene derivatives thereof, glycerol, cholic acid or derivatives thereof, lecithins, alcohols and phospholipids, glycerophospholipids (lecithins, kephalins, phosphatidyl serine), glyceroglycolipids (galactopyransoide), sphingophospholipids (sphingomyelin), and sphingoglycolipids (ceramides, gangliosides), DSS (docusate sodium, docusate calcium, docusate potassium, SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, zwitterionic surfactants (e.g. N-alkyl-N,N-dimethylammonio-1-propanesulfonates, 3-cholamido-1-propyldimethylammonio-1-propanesulfonate, dodecylphosphocholine, myristoyl lysophosphatidylcholine, hen egg lysolecithin), cationic surfactants (quarternary ammonium bases) (e.g. cetyl-trimethylammonium bromide, cetylpyridinium chloride), non-ionic surfactants, polyethyleneoxide/polypropyleneoxide block copolymers (Pluronics/Tetronics, Triton X-100, Dodecyl β-D-glucopyranoside) or polymeric surfactants (Tween-40, Tween-80, Brij-35), fusidic acid derivatives—(e.g. sodium tauro-dihydrofusidate etc.), long-chain fatty acids and salts thereof C6-C12 (e.g. oleic acid and caprylic acid), acylcarnitines and derivatives, $N_\alpha$-acylated derivatives of lysine, arginine or histidine, or side-chain acylated derivatives of lysine or arginine, $N_\alpha$-acylated derivatives of dipeptides comprising any combination of lysine, arginine or histidine and a neutral or acidic amino acid, $N_\alpha$-acylated derivative of a tripeptide comprising any combination of a neutral amino acid and two charged amino acids, or the surfactant may be selected from the group of imidazoline derivatives, or mixtures thereof. Each one of these specific surfactants constitutes an alternative embodiment.

The use of a surfactant in pharmaceutical compositions is well-known to the skilled person. For convenience reference is made to Remington: The Science and Practice of Pharmacy, 19th edition, 1995.

In some embodiments, pharmaceutically acceptable sweeteners comprise at least one intense sweetener such as saccharin, sodium or calcium saccharin, aspartame, acesulfame potassium, sodium cyclamate, alitame, a dihydrochalcone sweetener, monellin, stevioside or sucralose (4,1', 6'-trichloro-4,1',6'-trideoxygalactosucrose), or saccharin, sodium or calcium saccharin, and optionally a bulk sweetener such as sorbitol, mannitol, fructose, sucrose, maltose, isomalt, trehalose, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, and, in some embodiments, is about 0.06% in the low-dosage formulations and about 0.08% in the high-dosage ones. The bulk sweetener can effectively be used in larger quantities ranging from about 10% to about 35%, or from about 10% to 15% (w/v).

The formulations may be prepared by conventional techniques, e.g. as described in Remington's Pharmaceutical Sciences, 1985 or in Remington: The Science and Practice of Pharmacy, 19th edition, 1995, where such conventional techniques of the pharmaceutical industry involve dissolving and mixing the ingredients as appropriate to give the desired end product.

As used herein, the term "pharmaceutically acceptable" means approved by a regulatory agency of the Federal or a State government or listed in the U.S. Pharmacopeia or other generally recognized pharmacopeia (e.g., Remington's Pharmaceutical Sciences, Mack Publishing Co. (A. R. Gennaro edit. 1985)) for use in animals, and more particularly in humans.

As described herein any of the compounds described herein can be also be prepared salt forms, such as a pharmaceutically acceptable salt. The term "pharmaceutically acceptable salt" means a salt prepared from a base or an acid which is acceptable for administration to a patient, such as a mammal (for example, salts having acceptable mammalian safety for a given dosage regime). However, it is understood that the salts covered herein are not always required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids.

Administration of the compounds may be carried out using any method known in the art. For example, administration may be transdermal, parenteral, intravenous, intra-arterial, subcutaneous, intramuscular, intracranial, intraorbital, ophthalmic, intraventricular, intracapsular, intraspinal, intracisternal, intraperitoneal, intracerebroventricular, intrathecal, intranasal, aerosol, by suppositories, or oral administration. In some embodiments, a pharmaceutical composition can be for administration for injection, or for oral, pulmonary, nasal, transdermal, ocular administration. In some embodiments, the formulation is a long lasting depo formulation.

For oral administration, the peptide or a therapeutically acceptable salt thereof can be formulated in unit dosage forms such as capsules or tablets. The tablets or capsules may be prepared by conventional means with pharmaceutically acceptable excipients, including binding agents, for example, pregelatinised maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulphate. Tablets can be coated by methods well known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid or vitamin e and its derivatives (e.g. tocotrienols). The preparations can also contain buffer salts, flavoring, coloring, and/or sweetening agents as appropriate. If desired, preparations for oral administration can be suitably formulated to give controlled release of the active compound.

For topical administration, the composition can be formulated in a pharmaceutically acceptable vehicle containing 0.1 to 10 percent or 0.5 to 5 percent, of the active compound(s). Such formulations can be in the form of a cream, lotion, sublingual tablet, aerosols and/or emulsions and can be included in a transdermal or buccal patch of the matrix or reservoir type as are conventional in the art for this purpose.

For parenteral administration, the compounds can be administered by either intravenous, subcutaneous, or intramuscular injection, in compositions with pharmaceutically acceptable vehicles or carriers. The compounds can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use.

For administration by injection, it is common to use the compound(s) in solution in a sterile aqueous vehicle which may also contain other solutes such as buffers or preservatives as well as sufficient quantities of pharmaceutically acceptable salts or of glucose to make the solution isotonic (±10%) and pH between 4.0 and 8.0. In some embodiments, the pharmaceutical compositions may be formulated with a pharmaceutically acceptable carrier to provide sterile solutions or suspensions for injectable administration. In particular, injectables can be prepared in conventional forms, either as liquid solutions or suspensions, solid forms suitable for solution or suspensions in liquid prior to injection or as emulsions. In some embodiments, the formulation can be greater than 50%, 70%, 75%, 80%, 85%, 90%, or 95% non-aqueous. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized. Suitable pharmaceutical carriers are described in "Remington's pharmaceutical Sciences" by E. W. Martin.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch. For intranasal administration the compounds may be used, for example, as a liquid spray, as a powder or in the form of drops.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or injection (for example, subcutaneous or intramuscular). Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

The compounds may be administered to a patient at therapeutically effective doses to prevent, treat, or control diseases and disorders mediated, in whole or in part, as described herein. Pharmaceutical compositions comprising one or more of compounds may be administered to a patient in an amount sufficient to elicit an effective protective or therapeutic response in the patient. An amount adequate to accomplish this is defined as "therapeutically effective dose" or "therapeutically effective amount."

Toxicity and therapeutic efficacy of such compounds can be determined, for example, by standard pharmaceutical procedures in cell cultures or experimental animals, for example, by determining the LD50 (the dose lethal to 50% of the population) and the ED50 (the dose therapeutically effective in 50% of the population). The dose ratio between toxic and therapeutic effects is the therapeutic index and can be expressed as the ratio, LD50/ED50. Compounds that exhibit large therapeutic indices can be used. While compounds that exhibit toxic side effects can be used, care should be taken to design a delivery system that targets such compounds to the site of affected tissue to minimize potential damage to normal cells and, thereby, reduce side effects.

The data obtained from cell culture assays and animal studies can be used to formulate a dosage range for use in humans. In some embodiments, the dosage of such compounds is within a range of circulating concentrations that include the ED50 with little or no toxicity. The dosage can vary within this range depending upon the dosage form employed and the route of administration. For any compound used in the methods, the therapeutically effective dose can be estimated initially from cell culture assays. A dose can be formulated in animal models to achieve a circulating plasma concentration range that includes the IC50 (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC) and, in some embodiments, combined with mass spectrometry (LC-MS). In general, the dose equivalent of a modulator is from about 1 ng/kg to 20 mg/kg for a typical subject.

The amount and frequency of administration of the compounds and/or the pharmaceutically acceptable salts thereof will be regulated according to the judgment of the attending clinician considering such factors as age, condition and size of the patient as well as severity of the symptoms being treated. An ordinarily skilled physician or veterinarian can readily determine and prescribe the effective amount of the drug required to prevent, counter or arrest the progress of the condition. In general it is contemplated that an effective amount would be from 0.001 mg/kg to 10 mg/kg body weight, and in particular from 0.01 mg/kg to 1 mg/kg body weight. More specifically it is contemplated that an effective amount would be to continuously infuse by intravenous administration from 0.01 micrograms/kg body weight/min to 100 micrograms/kg body weight/min for a period of 12 hours to 14 days. It may be appropriate to administer the required dose as two, three, four or more sub-doses at appropriate intervals throughout the day. Said sub-doses may be formulated as unit dosage forms, for example, containing 0.01 to 500 mg, and in particular 0.1 mg to 200 mg of active ingredient per unit dosage form.

In some embodiments, the pharmaceutical composition comprising the compound, or pharmaceutically acceptable salt thereof, is administered (e.g. infused) for about, or at least, 1, 2, 3, 4, 5, 10, 15, 20, 25, 30, 35, 40, 45, 50, 60, 120, 180, or 240 minutes. In some embodiments, the time of administration is about 5 to about 60 minutes. In some embodiments, the time of administration is about 10 to about 45 minutes. the time of administration is about 20 to about 40 minutes.

In some embodiments, the compound, or pharmaceutically acceptable salt thereof, is administered at a rate of about 0.5 µg/kg/min to about 20 µg/kg/min, about 0.5 µg/kg/min to about 15 µg/kg/min, about 0.5 µg/kg/min to about 10 µg/kg/min, about 0.5 µg/kg/min to about 5 µg/kg/min, about 0.5 µg/kg/min to about 4 µg/kg/min, about 0.5 µg/kg/min to about 3 µg/kg/min, about 0.5 µg/kg/min to about 2 µg/kg/min, about 0.5 µg/kg/min to about 1 µg/kg/min, about 1 µg/kg/min to about 2 µg/kg/min, about 1 µg/kg/min to about 3 µg/kg/min, about 1 µg/kg/min to about 4 µg/kg/min, about 1 µg/kg/min to about 5 µg/kg/min, about 1 µg/kg/min to about 10 µg/kg/min, about 1 µg/kg/min to about 15 µg/kg/min, about 1 µg/kg/min to about 15 µg/kg/min, about 1 µg/kg/min to about 20 µg/kg/min. In some embodiments, the compound, or pharmaceutically acceptable salt thereof, described herein is administered at a rate of about, or at least, 0.5 µg/kg/min, 1 µg/kg/min, 2 µg/kg/min, 3 µg/kg/min, 4 µg/kg/min, 5 µg/kg/min, 6 µg/kg/min, 7 µg/kg/min, 8 µg/kg/min, 9 µg/kg/min, 10 µg/kg/min, 15 µg/kg/min, or 20 µg/kg/min. The dose can be administered for about, or at least, 1-24 hours or any hourly increment in thereof, including the endpoints. In some embodiments, the dose is administered for about 1 to about 7 days, about 2 to about 7 days, about 3 to about 7 days, about 4 to about 7 days, about 5 to about 7 days, or about 6 to about 7 days. In some embodiments, the dose is administered for about 1, about 2, about 3, about 4, about 5, about 6, or about 7 days.

In some embodiments, the pharmaceutical preparation is in a unit dosage form. In such form, the preparation is subdivided into suitably sized unit doses containing appropriate quantities of the active component, e.g., an effective amount to achieve the desired purpose. The quantity of active compound in a unit dose of preparation may be varied or adjusted from about 0.01 mg to about 1000 mg, from about 0.01 mg to about 750 mg, from about 0.01 mg to about 500 mg, and from about 0.01 mg to about 250 mg, according to the particular application. In some embodiments, the dosage is from about 1 to about 50 mg. In some embodiments, the dosage is from about 10 mg to about 50 mg, about 10 mg to about 40 mg, about 10 mg to about 30 mg, about 10 mg to about 20 mg, about 20 mg to about 50 mg, about 20 mg to about 40 mg, or about 20 mg to about 30 mg. In some embodiments, the dosage is about 5, 10, 15, 20, 25, 30, 35, 40, 45, or 50 mg. The actual dosage employed may be varied depending upon the requirements of the patient and the severity of the condition being treated. Determination of the proper dosage regimen for a particular situation is within the skill of the art. For convenience, the total dosage may be divided and administered in portions during the day as required. In some embodiments, the dosage is administered daily, twice a day, twice a week, weekly, biweekly (every two weeks), twice a month, or monthly. The dosing schedule can be modified to fit the therapeutic index of the compound.

In some embodiments, the unit dosage form is administered in an amount to deliver a blood level of the compound, or a pharmaceutically acceptable salt thereof of, or active form thereof (e.g. active metabolite such as, but not limited to, the reduced sulfhydryl form) of about 25 to about 1000 ng/ml.

The compounds and compositions described herein can be used to treat diseases associated with high iron in the blood or iron overload when hepcidin levels are abnormally low. Examples of such conditions include, but are not limited to, beta thalassemia or hemochromatosis. Accordingly, in some embodiments, methods of treating beta thalassemia or hemochromatosis are provided. The compounds and compositions described herein can also be used for the treatment of other diseases of iron metabolism. In some embodiments, the method comprises administering to a subject, or a subject in need thereof, a compound, or a pharmaceutically acceptable salt thereof, of a compound described herein. In some embodiments, the compound is a compound, or pharmaceutically acceptable salt thereof, of Formula I, II, II-A, II-B, II-C, III, III-A, IV, V, VI, VI-A, Compound 1, Compound 2, Compound 3, Compound 4, Compound 5, Compound 6, Compound 7, Compound 8, Compound 9, or Compound 10. In some embodiments, Compound 1, or a pharmaceutically acceptable salt thereof, is not administered to a subject or a subject in need thereof. In some embodiments, the method comprises administering Compound 5, or a pharmaceutically acceptable salt thereof, which is then converted into Compound 6, or a salt thereof, in the subject. In some embodiments, the method comprises administering Compound 2, or a pharmaceutically acceptable salt thereof, which is then converted into Compound 1, or a salt thereof, in the subject.

As used herein, a "disease of iron metabolism" includes diseases where aberrant iron metabolism directly causes the disease, or where iron blood levels are dysregulated causing disease, or where iron dysregulation is a consequence of another disease, or where diseases can be treated by modulating iron levels, and the like. More specifically, a disease of iron metabolism according to this disclosure includes iron overload diseases, iron deficiency disorders, disorders of iron biodistribution, other disorders of iron metabolism and other disorders potentially related to iron metabolism, etc. Diseases of iron metabolism include, for example, hemochromatosis, HFE mutation hemochromatosis, ferroportin mutation hemochromatosis, transferrin receptor 2 mutation hemochromatosis, hemojuvelin mutation hemochromatosis, hepcidin mutation hemochromatosis, juvenile hemochromatosis, neonatal hemochromatosis, hepcidin deficiency, transfusional iron overload, beta thalassemia major, beta thalassemia intermedia, HbE/thalassemia, alpha thalassemia, sideroblastic anemia, myelodysplastic syndrome, sickle cell disease, porphyria, porphyria cutanea tarda, African iron overload, hyperferritinemia, ceruloplasmin deficiency, atransferrinemia, congenital dyserythropoietic anemia, anemia of chronic disease, anemia of inflammation, anemia of infection, hypochromic microcytic anemia, iron-deficiency anemia, iron-refractory iron deficiency anemia, anemia of chronic kidney disease, erythropoietin resistance, iron deficiency of obesity, other anemias, Friedreich ataxia, gracile syndrome, Hallervorden-Spatz disease, Wilson's disease, pulmonary hemosiderosis, alcoholic liver disease, hepatitis C, non-alcoholic liver disease (NASH), hepatocellular carcinoma, cancer, hepatitis, cirrhosis of liver, pica, chronic renal failure, insulin resistance, diabetes, atherosclerosis, neurodegenerative disorders, multiple sclerosis, Parkinson's disease, Huntington's disease, and Alzheimer's disease. Accordingly, in some embodiments, methods of treating such diseases are provided. In some embodiments, the method comprises administering to a subject, or a subject in need thereof, a compound, or a pharmaceutically acceptable salt thereof, of a compound described herein. In some embodiments, the compound is a compound, or pharmaceutically acceptable salt thereof, of Formula I, II, II-A, II-B, II-C, III, III-A, IV, V, VI, VI-A, Compound 1, Compound 2, Compound 3, Compound 4, Compound 5, Compound 6, Compound 7, Compound 8, Compound 9, or Compound 10. In some embodiments, Compound 1, or a pharmaceutically acceptable salt thereof, is not administered to a subject or a subject in need thereof. In some embodiments, the method comprises administering Compound 5, or a pharmaceutically acceptable salt thereof, which is then converted into Compound 6, or a salt thereof, in the subject. In some embodiments, the method comprises administering Compound 2, or a pharmaceutically acceptable salt thereof, which is then converted into Compound 1, or a salt thereof, in the subject.

In some embodiments, the compounds can be used to treat diabetes (Type I or Type II), insulin resistance, glucose intolerance and other disorders may be ameliorated by treating underlying iron metabolism disorders. In some embodiments, the diseases of iron metabolism are iron overload diseases, which include, but are not limited to, hemochromatosis, iron-loading anemias, alcoholic liver diseases and chronic hepatitis C. Accordingly, in some embodiments, methods of treating such diseases are provided. In some embodiments, the method comprises administering to a subject, or a subject in need thereof, a compound, or a pharmaceutically acceptable salt thereof, of a compound described herein. In some embodiments, the compound is a compound, or pharmaceutically acceptable salt thereof, of Formula I, II, II-A, II-B, II-C, III, III-A, IV, V, VI, VI-A, Compound 1, Compound 2, Compound 3, Compound 4, Compound 5, Compound 6, Compound 7, Compound 8, Compound 9, or Compound 10. In some embodiments, Compound 1, or a pharmaceutically acceptable salt thereof, is not administered to a subject or a subject in need thereof. In some embodiments, the method comprises administering Compound 5, or a pharmaceutically acceptable salt thereof, which is then converted into Compound 6, or a salt thereof, in the subject. In some embodiments, the method comprises administering Compound 2, or a pharmaceutically acceptable salt thereof, which is then converted into Compound 1, or a salt thereof, in the subject.

In some embodiments, the compounds described herein can be used to treat diseases associated with accelerated rates of erythropoiesis. An example of such a condition includes, but is not limited to polycythemia vera. Accordingly, in some embodiments, methods of treating such diseases are provided. In some embodiments, the method comprises administering to a subject, or a subject in need thereof, a compound, or a pharmaceutically acceptable salt thereof, of a compound described herein. In some embodiments, the compound is a compound, or pharmaceutically acceptable salt thereof, of Formula I, II, II-A, II-B, II-C, III, III-A, IV, V, VI, VI-A, Compound 1, Compound 2, Compound 3, Compound 4, Compound 5, Compound 6, Compound 7, Compound 8, Compound 9, or Compound 10. In some embodiments, Compound 1, or a pharmaceutically acceptable salt thereof, is not administered to a subject or a subject in need thereof. In some embodiments, the method comprises administering Compound 5, or a pharmaceutically acceptable salt thereof, which is then converted into Compound 6, or a salt thereof, in the subject. In some embodiments, the method comprises administering Compound 2, or a pharmaceutically acceptable salt thereof, which is then converted into Compound 1, or a salt thereof, in the subject.

The compounds described herein can also be used to reduce serum iron concentration. In some embodiments, the compounds reduce serum iron concentration at least 10%, 20%, 30%, 40%, 50%, 60%, 70%, 80% or 90%. The degree of reduction is compared to the levels of serum ion concentration prior to the administration of the compound. Accordingly, in some embodiments, methods of reducing serum iron concentration are provided. In some embodiments, the method comprises administering to a subject, or a subject in need thereof, a compound, or a pharmaceutically acceptable salt thereof, of a compound described herein. In some embodiments, the compound is a compound, or pharmaceutically acceptable salt thereof, of Formula I, II, II-A, II-B, II-C, III, III-A, IV, V, VI, VI-A, Compound 1, Compound 2, Compound 3, Compound 4, Compound 5, Compound 6, Compound 7, Compound 8, Compound 9, or Compound 10. In some embodiments, Compound 1, or a pharmaceutically acceptable salt thereof, is not administered to a subject or a subject in need thereof. In some embodiments, the method comprises administering Compound 5, or a pharmaceutically acceptable salt thereof, which is then converted into Compound 6, or a salt thereof, in the subject. In some embodiments, the method comprises administering Compound 2, or a pharmaceutically acceptable salt thereof, which is then converted into Compound 1, or a salt thereof, in the subject.

The presently described compounds can be administered in combination with other compounds used to treat similar diseases. The compounds can be administered simultaneously or sequentially. Examples of such molecules are described for example in U.S. Patent Application Publication Nos. 20120040894, 20130203662, and PCT Publication No. WO/2013/086143, each of which is hereby incorporated by reference in its entirety. The compounds described herein can be made according to similar methods as well, although any method of preparation can be used.

The compounds described herein can also be prepared or used as a medicament. The compounds can be prepared as a medicament for any condition or disease described herein including, but not limited to, a disease of iron metabolism, beta thalassemia or hemochromatosis and the other conditions described throughout the present document. Embodiments described herein also provide uses of any compound, or pharmaceutically acceptable salt thereof, described herein in the, or for the treatment of any disease or condition described herein. They can also be used for reducing serum iron concentration. In some embodiments, they are used in the preparation of a medicament for reducing serum iron concentration. The compounds, or pharmaceutically acceptable salts thereof, can be used in the manufacture of a medicament in, for example, the treatment of a disease or condition described herein.

In some embodiments, the base peptide, Ida-Thr-His-Dpa-Npc-Arg-Cys-Arg-Trp-Ahx-Ida(NH-Pal)-NH2, is produced by standard by solid-phase synthesis methods. For example, the peptide is assembled on a Fmoc Rink modified polystyrene resin using traditional Fmoc/tBu based chemistry. The protected amino acids can include: Boc-Iminodiacetic acid, Fmoc-ε-Aminohexanoic acid-OH, Fmoc-Arg(Pbf)-OH, Fmoc-β-3-Homoproline-OH (CAS #: 193693-60-6), Fmoc-Cys(Trt)-OH, Fmoc-Diphenylalanine-OH, Fmoc-His(Trt)-OH, Fmoc-Iminodiacetic acid-OH (CAS #112918-82-8), palmityl amine, Fmoc-Thr(tBu)-OH, Fmoc-Trp(Boc)-OH. In some embodiments, in place of Fmoc-β-3-Homoproline-OH, Fmoc-Nipecotic (Fmoc-piperidine-3-carboxylic acid) acid is used to generate a compound of Compound 5 or Compound 6. The Fmoc-Nipecotic acid can be the R or S enantiomer or a racemic mixture (e.g. (R) or D-: CAS #: 193693-67-3; (S) or L-: CAS #: 193693-68-4, each incorporated by reference. In some embodiments, the L-form is used. In some embodiments, the D-form is used. In some embodiments, a compound is synthesized using Fmoc-L-Pipecolic acid (Fmoc-L-homoproline; (R)-Fmoc-piperidine-2-carboxylic acid (CAS #: 86069-86-5) in place of the Fmoc-β-3-Homoproline-OH. In some embodiments, in place of Fmoc-β-3-Homoproline-OH, Fmoc-isoNPC (CAS #: 148928-15-8) or Fmoc-bAla (CASE #35737-10-1) is used to produce the compounds described herein. The Fmoc derivatives of Ida (CAS #: 112918-82-8) and Dpa (CAS #: 201484-50-6) and can be used in the synthesis of the compounds described herein.

Alternatively, in some embodiments, the peptides described herein could be assembled using the cysteine derivative that reflects the modification of the cysteine in the ultimate product, for example, but not limited to, using Fmoc-Cys (S—S—CH3) (sulfenylated Cysteine) instead of Fmoc-Cys (Trt). Fmoc chemistry can be used throughout the peptide chain assembly starting with the addition of the Fmoc-iminodiacetic acid, followed by palmityl amine, then Fmoc-ε-Aminohexanoic acid-OH and subsequent amino acids until the peptide sequence is assembled on the resin. The sidechain protecting groups and the peptide can be removed from the resin and isolated using standard procedures known in the art of peptide synthesis. The peptides can be purified and isolated as a salt, such as a HCl salt. In some embodiments, the peptides can be isolated as the acetate or trifluoroacetate salt forms. In some embodiments, the free cysteine sulfhydryl may be modified at the crude peptide stage or after the base peptide, e.g. (Ida-Thr-His-Dpa-Npc-Arg-Cys-Arg-Trp-Ahx-Ida(NH-Pal)-NH$_2$); SEQ ID NO: 11) is purified. In some embodiments, the sidechain of the Cysteine can be modified with methyl methanethiosulfonate (MMTS), acetic anhydride, or ethyl iodide to produce the sulfenylated (—SCH$_3$), acetylated (—C(O)CH$_3$), and ethylated (—CH$_2$CH$_3$) derivatives, respectively, of the base peptide. Other known modifications or equivalent steps of the methods described herein can also be used in order to make the compounds described herein. The same synthesis can be applied to any of the compounds described herein with modifications based upon the desired compound. For example, in the above synthesis β-3-Homoproline can be replaced with Nipecotic residue (piperidine-3-carboxylic acid) to generate a compound of Compound 5 or Compound 6. As described above, the compound can be the R or S enantiomer at that position or a racemic mixture. In some embodiments, a compound is synthesized using Fmoc-L-Pipecolic acid (Fmoc-L-homoproline; (R)-Fmoc-piperidine-2-carboxylic acid (CAS #: 86069-86-5) in place of the Fmoc-β-3-Homoproline-OH as described above in place of Fmoc-β-3-Homoproline-OH to generate additional compounds.

In the combination therapies, one or more compounds or compositions are coadministered with one or more drugs for the treatment of the diseases described herein and/or to reduce side effects associated with high doses of these therapeutics. The combination therapies described herein can have synergistic and additive therapeutic effects. Synergy is defined as the interaction of two or more agents so that their combined effect is greater than the sum of their individual effects. For example, if the effect of drug A alone in treating a disease is 25%, and the effect of drug B alone in treating a disease is 25%, but when the two drugs are combined the effect in treating the disease is 75%, the effect of A and B is synergistic. Additivity is defined as the interaction of two or more agents so that their combined effect is the same as the sum of their individual effects. For example, if the effect of drug A alone in treating a disease is 25%, and the effect of drug B alone in treating a disease is 25%, but when the two drugs are combined the effect in treating the disease is 50%, the effect of A and B is additive.

An improvement in the drug therapeutic regimen can be described as the interaction of two or more agents so that their combined effect reduces the incidence of adverse event (AE) of either or both agents used in co-therapy. This reduction in the incidence of adverse effects can be a result of, e.g., administration of lower dosages of either or both agent used in the co-therapy. For example, if the effect of Drug A alone is 25% and has an adverse event incidence of 45% at labeled dose; and the effect of Drug B alone is 25% and has an adverse event incidence of 30% at labeled dose, but when the two drugs are combined at lower than labeled doses of each, if the overall effect is 35% (an improvement, but not synergistic or additive) and the adverse incidence rate is 20%, there is an improvement in the drug therapeutic regimen.

EXAMPLES

The following examples are illustrative, but not limiting, of the methods and compositions described herein. Other suitable modifications and adaptations of the variety of conditions and parameters normally encountered in therapy and that are obvious to those skilled in the art are within the spirit and scope of the embodiments.

Example 1

Stability of Compounds

Initially the stability of Compound 1 was previously characterized and there was significant degradation observed by HPLC after about 24 hours at 40° C. (Table 1) where 90% of the main peak (% area under the curve, % AUC) was lost after about 24 hours. The effect of various antioxidants and thiol scavengers that might be used in a medicament were studied.

TABLE 1

Stability of Compound 1 pH 6 formulations at 40° C. (% AUC)

| Form No. | Antioxidant (10 mM) | T0 | T ~24 hours | Difference (%) (T24 − T0) |
|---|---|---|---|---|
|  | None | 94.4 | 4.0 (estimated) | −90 |
| 1 | Ascorbate | 74.5 | 1.9 | −73 |
| 2 | α-lipoic acid (LPA) | 88.0 | 54.1 | −34 |
| 3 | N—Ac-Cysteine | 76.2 | 29.2 | −47 |
| 4 | Methionine | 89.2 | 63.0 | −36 |
| 5 | Thioglycerol | 84.2 | 55.7 | −28 |

Although degradation could be mitigated somewhat by these antioxidants and thiol scavengers, significant degradation was still observed (~30-70%).

Three other compounds were also tested, Compound 2, Compound 3, and Compound 4. Compounds 2, 3, and 4 are modifications of Compound 1 at the sidechain of Cysteine 7. Compound 2 has a disulfide bond attached to Cysteine 7, Compound 3 has thioester bond attached to Cysteine 7, and Compound 4 has an ethyl group attached to the sidechain sulfur of Cysteine 7. The peptides were incubated in sodium acetate buffer pH 6 at two temperature conditions and then analyzed via reversed-phase HPLC. The chromatography performed was with an Ascentis Phenyl 2.7 micron column (4.6×150 mm). The binary gradient (1 ml/min) was 36% to 56% B in 40 minutes followed by an increase to 65% B in 5 minutes where A=0.1% trifluoroacetic acid in water and B=0.1% trifluoroacetic acid in acetonitrile.

As shown in Tables 2 and 3 below and in the accompanying figures, the stability of Compound 2, Compound 3, and Compound 4 was enhanced to varying degrees with the modification of the sidechain of Cysteine 7.

Compound 1, which has a free cysteine, was almost completely degraded after 18 hours at 40° C. (Tables 2, 3). Surprisingly and unexpectedly, the stability differences observed depended upon the type of modification of the cysteine sidechain sulfur. Compound 4, which has a cysteine irreversibly modified on the sulfur, not unexpectedly showed no evidence of degradation involving the cysteine. Unexpectedly, significant differences in stability was observed when different exchangeable chemical bonds were used to block the cysteine. Compound 3, which has a thioester linkage on the cysteine side chain, showed significant amounts of degradation, 30% after 18 hours at 40° C., whereas Compound 2, in which the cysteine is blocked by a disulfide linkage showed excellent stability, with little degradation observed after 18 hours at 40° C.

An additional surprising and unexpected effect was the number of significant degradation peaks observed. Compound 1 has a retention time of about 19 minutes and degrades to a single major peak at about 37 minutes with a minor shoulder. Compound 3, which has the reactive sulfur blocked with a thioester, produces multiple major peaks including one right before the native peak at 21 minutes. Compound 2 shows no significant degradation peak under similar conditions. These data demonstrate that the nature of the chemical group blocking the sulfur on the cysteine produces unexpected differences in chemical stability. Thus, Compound 2 has the surprising and unexpected stability as compared to another reversible sulfur blocking group (e.g. a compound of Compound 3.

TABLE 2

% Purity of the Compound

| Compound | Initial | 6 Hours | | 18 Hours | |
|---|---|---|---|---|---|
|  |  | 25° C. | 40° C. | 25° C. | 40° C. |
| 1 | 96.9 | 58.9 | 11.9 | N/A | <5 |
| 2 | 99.5 | 99.6 | 99.4 | 99.3 | 99.4 |
| 3 | 97.3 | 96.9 | 84.9 | 95.1 | 67.2 |
| 4 | 96.7 | 96.8 | 96.6 | 96.2 | 97.0 |

TABLE 3

Change in Main Peak % Area After 18 H Incubation

| Compound | 25° C. | 40° C. |
|---|---|---|
| 1 | N/A | −95-100 |
| 2 | −0.2 | −0.1 |
| 3 | −2.3 | −30 |
| 4 | −0.5 | 0.3 |

The degradation products seen with various compounds are shown in chromatographs, which can be viewed in U.S. Provisional Application No. 62/085,817, filed Dec. 1, 2014, which is hereby incorporated by reference in its entirety.

Compound 5, which has the same disulphide block of the reactive cysteine as Compound 2 was also evaluated in stability studies over a 4 week period in 50 mM Na Acetate pH 5 at different temperatures. The results are summarized in Table 4. Compound 5 has excellent 4 week stability at both tested temperatures.

TABLE 4

% Purity of Compound 5 in 50 mM NaAcetate, pH 5 at different temperatures.

| Week | % Purity | |
|---|---|---|
|  | 2-8° C. | 25° C. |
| 0 | 96.9 | 96.9 |
| 1 | 96.8 | 96.8 |

TABLE 4-continued

% Purity of Compound 5 in 50 mM NaAcetate,
pH 5 at different temperatures.

| | % Purity | |
|---|---|---|
| Week | 2-8° C. | 25° C. |
| 2 | 96.8 | 96.3 |
| 4 | 96.7 | 96.1 |

The stability of Compound 5 was also examined in 0.01% HCl at elevated temperatures again displaying unexpected and remarkable stability, as shown in Table 5.

TABLE 5

Compound 5 Stability in HCl at 40° C.

| Day | % Purity |
|---|---|
| 0 | 97.1 |
| 7 | 96.8 |

Example 2

Half Life of Compounds in Rat Plasma

The in vitro stability of Compounds 1-4 in rat plasma at 37° C. was examined to give an indication of stability in a whole animal model (Table 6). As expected the plasma stability of Compounds 2-4 was better than Compound 1 since the reactive cysteine has been blocked in these compounds. Based on the chemical stability one would expect Compound 2 to have significantly more stability than Compound 3, however in plasma the opposite was observed. The data indicate that the nature of the blocking group chemical bond effects on plasma stability.

The in vitro stability of Compound 5 is even greater than that for Compound 2 (data not shown), which is an unexpected advantage and could not have been predicted.

TABLE 6

Stability of Compounds in Rat Plasma (37° C.)

| | Cmpd 1 | Cmpd 2 | Cmpd 3 | Cmpd 4 |
|---|---|---|---|---|
| In vitro plasma stability (Ratio of compound/benfluorex (std) degradation) | 0.41 | 0.98 | 1.78 | 2.74 |
| In vitro plasma stability (T ½) | 23 min | 40 min | 73 min | 112 min |

Example 3

Pharmacokinetic and Pharmacodynamic Characterization

Compounds 1-4 were tested in rats to determine compound pharmacokinetics and hepcidin mimetic activity in vivo as measured by serum iron reduction. The effectiveness of the compounds for serum iron reduction should correlate with the treatment of iron metabolism disorders. Individual compounds, in this example and the following examples were generally formulated in DSPE-PEG(2000) (SUNBRIGHT® DSPE-020CN, NOF America Corporation) (30 mg/mL) and dosed subcutaneously at a compound dose of 7.5 mg/kg.

The compound was prepared according to the following typical preparation. The dosing solution was prepared (7.5 mg compound/mL in clear solution) by weighing the compound into vial and an aliquot of ethanol is added into the vial and mixture vortexed. DSPE-020CN was added and the solution was vortexed, and, if necessary, the mixture was heated at 37° C. for 10-15 minutes to fully dissolve the DSPE-020CN. The ethanol was evaporated with nitrogen gas stream for 1-3 hours. Sterile water was then added and the mixture was vortexed or, if necessary, sonicated to give a clear solution.

After subcutaneous injection compound quantities in blood were measured over the subsequent 24 hours via LC/MS. In general the level of compound in blood (exposure) as measured by area under the curve (AUC (0-24)) (Table 7) was consistent with what was observed in in vitro plasma studies (Table 6).

TABLE 7

Compound Exposure After Subcutaneous Administration of Compounds 1-4 in the Rat

| | Compound 1 | Compound 2 | Compound 3 | Compound 4 |
|---|---|---|---|---|
| $AUC_{(0-24)}$ (hr*ng/mL, mean ± SD) | 2753 ± 715 | 1008 ± 373 | 12225 ± 1516 | 25583 ± 5982 |

Serum iron was measured during the 24 h following subcutaneous administration in a rat of Compounds 1-4 and is summarized in FIG. 1. Compounds 1-3 all showed sustained reduction in serum iron, as would be expected from a hepcidin mimetic. The observed effects on serum iron were unexpectedly similar in Compounds 1-3 despite the differences at Cysteine 7 and the differences in blood levels of the compounds (Table 7). Compound 4 showed minimal reduction in serum iron after 24 h despite very high blood levels, indicating lack of significant hepcidin activity compared to the other compounds.

Figure 2:
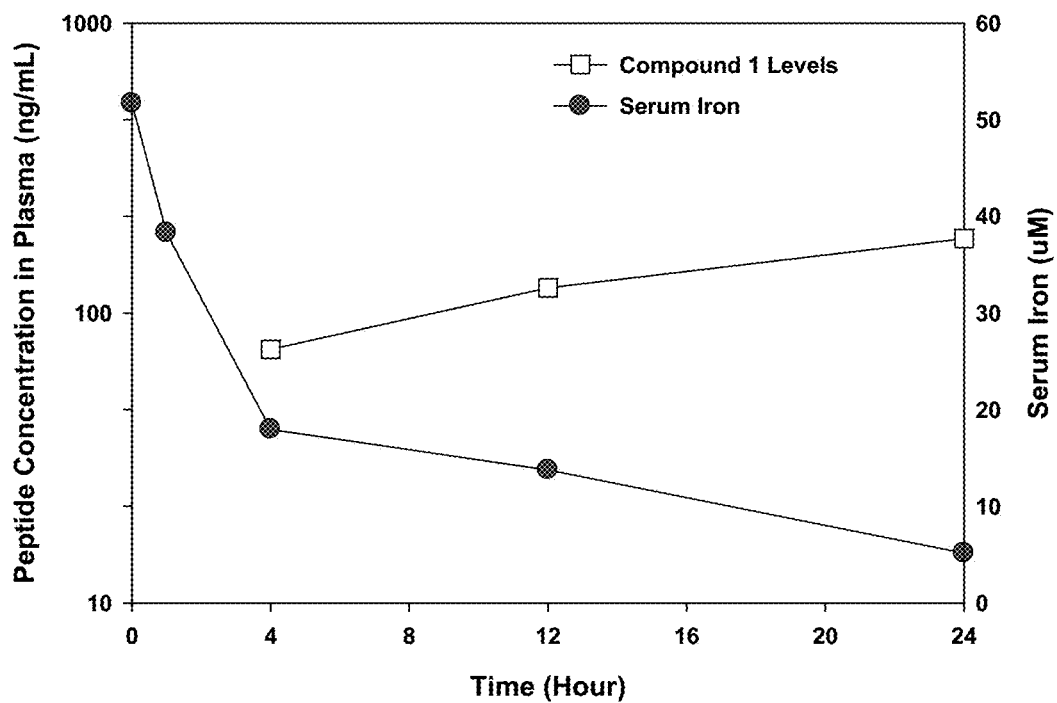
FIG. 2 illustrates time course of blood levels of Compound 1 and change in serum iron following subcutaneous administration of Compound 1 in the rat (7.5 mg/kg).

Another way to present the data is to display both the blood levels of the compound and reduction in iron levels as a function of time. The blood levels of Compound 1 and its effect on iron levels after subcutaneous delivery to the rat are displayed in FIG. 2. Compound 1 causes a significant drop in serum iron level as would be expected from a hepcidin mimetic. The blood level of Compound 1 remains little changed out to at least 24 hours.

Figure 3:
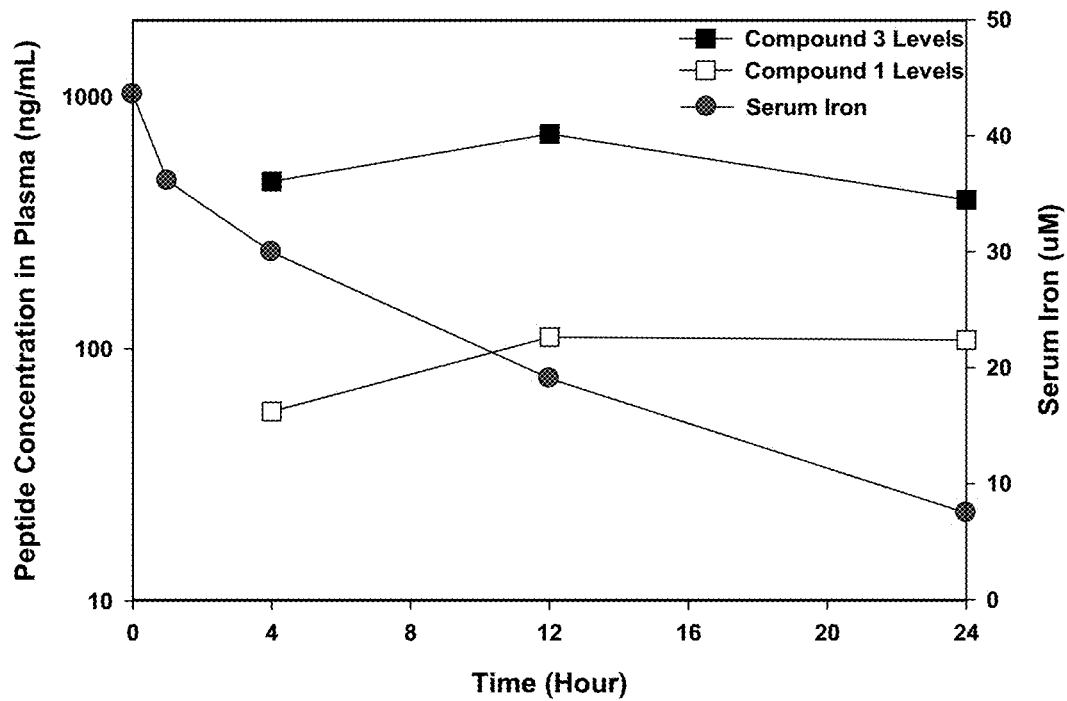
FIG. 3 illustrates time course of blood levels of Compound 1 and Compound 3 and change in serum iron following subcutaneous administration of Compound 3 in the rat (7.5 mg/kg).

A similar effect on serum iron was observed with Compound 3 (FIG. 3). However the plasma blood levels of Compound 3 were observed to be 5-9 times greater than observed in Compound 1. These data would suggest that Compound 3 was less potent that Compound 1. Since Compound 3 contained a reversible blocking group on the cysteine, it was postulated that the peptide might be converting to Compound 1 in vivo by removal of the modification of the cysteine sulfur to generate an active metabolite. Further analysis showed levels of Compound 1 that were comparable to the levels observed when just Compound 1 was dosed, suggesting that unexpectedly Compound 3 was being converted to Compound 1 (FIG. 3).

Figure 4:
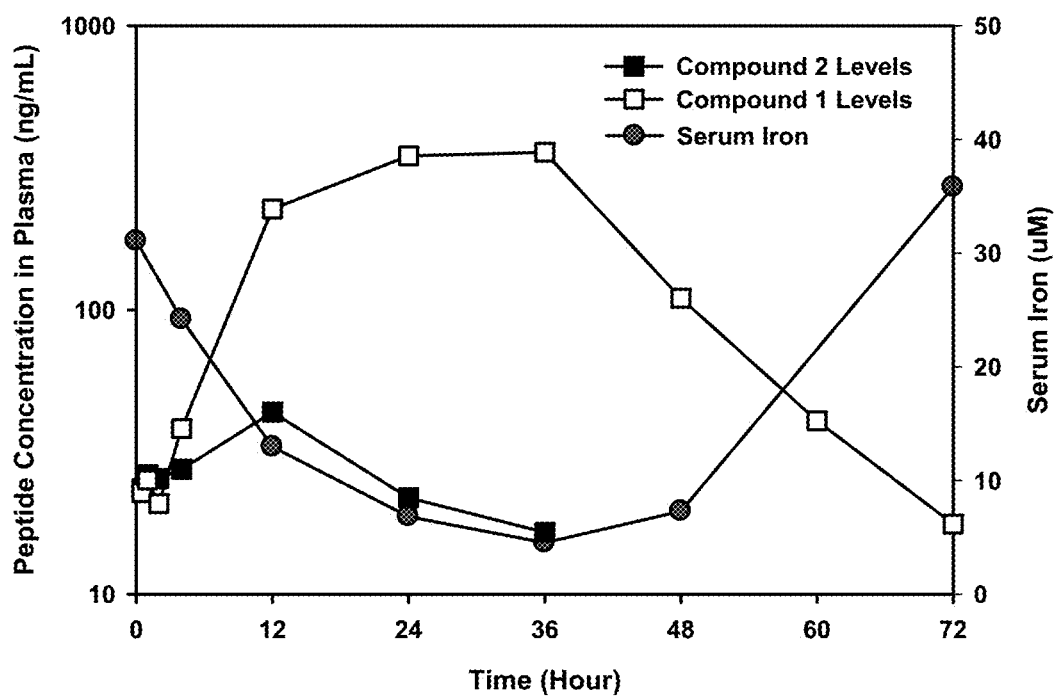
FIG. 4 illustrates time course of blood levels of Compound 1 and 2 and serum iron levels following subcutaneous administration of Compound 2 in the rat (7.5 mg/kg).

Compound 2 was dosed by subcutaneous administration to the rat and results were followed for a longer period of time. A similar serum iron level reduction as Compound 1 was observed (FIG. 4). Additionally, as observed for Compound 3, administration of Compound 2 resulted in blood levels of Compound 1. However in this case the blood level of Compound 1 was unexpectedly higher than expected based on the low levels of the prodrug Compound 2 that were observed (FIG. 4), in contrast to the observations when Compound 3 is dosed (FIG. 3).

Figure 5:
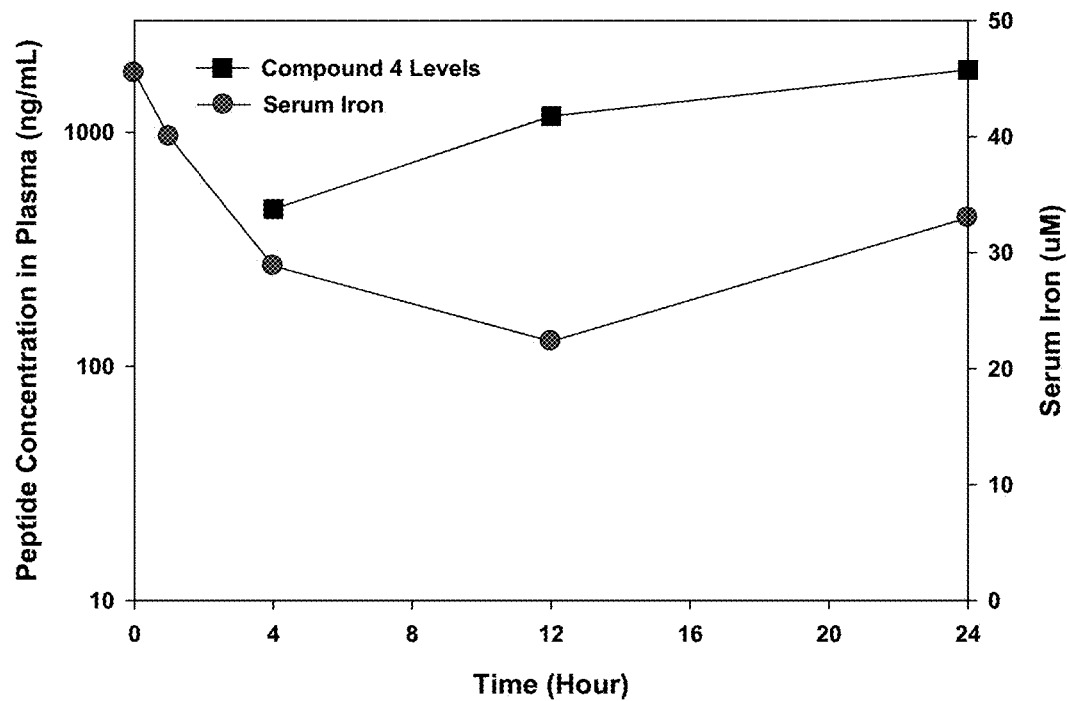
FIG. 5 illustrates time course of blood levels of Compound 4 and serum iron following subcutaneous administration of Compound 4 in the rat (7.5 mg/kg).

Compound 4 displayed little activity in vivo as displayed in FIG. 5. No levels of Compound 1 were detected in the plasma samples of the animals dosed with Compound 4.

Based upon the observed results, peptides with reversibly blocked cysteines have superior formulation stability while retaining hepcidin activity. The biological activity of such compounds is determined by the conversion of the compound to a species that has a free cysteine residue. In the case of Compounds 2 and 3 the active species appears to be Compound 1, but if the amino acid sequence of the peptide is changed other active species can be generated (see Example 5). Based upon these results, it has been demonstrated herein that the nature of the bond on the cysteine sulfur led to unexpected and surprising results not only on the chemical stability but that also affect the in vivo stability and pharmacodynamic properties. As discussed herein, the nature of the bond to the cysteine can be modified and can include the addition of electron donating or withdrawing groups that affect the lability of this bond. The data presented of Compounds 2 and 3 in particular show surprising and unexpected effects both in chemical stability as well as pharmacodynamic properties. Compound 3 has lower chemical stability than Compound 2 (Tables 2 and 3) but better plasma stability (Table 6). In addition Compounds 2 and 3 appears to be converted into Compound 1 as shown in FIGS. 3 and 4 and the generation of active metabolite (Compound 1) from the other compounds is determined by the nature of the bond on the cysteine sulfur. These results for both Compounds 2 and 3 in both in vitro and in vivo characterization could not have been predicted and are surprising.

Example 4

Compound 5 has Unexpected Solubility Characteristics

The solubility of compounds at ambient temperature was tested under various conditions, as shown in Table 8. Different solvent compositions with different properties that are commonly used as a basis for pharmaceutical compositions were added to known quantities of the indicated compound and mixed. If a clear solution was not obtained, additional solvent was added and the solution mixed. This process was repeated until the compound exhibited a clear solution or there was not significant improvement in solubility. Conditions that show a range of solubility suggest the true solubility was within that range. For example "50-100" would indicate that the compound was not soluble at 100 mg/mL but upon additional solvent to have a final concentration of 50 mg/mL, the compound was soluble.

TABLE 8

Solubility of Selected Compounds in a Variety of Solutions

| Solubility Conditions | Compound # | | | | | |
|---|---|---|---|---|---|---|
| | 2 | 9 | 10 | 5 | 7 | 8 |
| | Solubility (mg/mL) at Ambient Temperature | | | | | |
| Water | 50-100 | 50-100 | <25* | >100 | 50-100 | 50-100 |
| 50% propylene glycol, pH 2.7 | 50-100 | 30-50 | <20* | 50-100 | >100 | 30-50 |
| 30% PEG 400 | 25-35 | 20-35 | <10* | 50-100 | >35 | 25-35 |
| 50% EtOH/water | >100 | >100 | <10* | >100 | >100 | >100 |

TABLE 8-continued

Solubility of Selected Compounds in a Variety of Solutions

| Solubility Conditions | Compound # | | | | | |
|---|---|---|---|---|---|---|
| | 2 | 9 | 10 | 5 | 7 | 8 |
| | Solubility (mg/mL) at Ambient Temperature | | | | | |
| 10% Tween 80 pH 2.3-2.8** | 60-100 | 30-50 | 15-20 | >200 | >100 | 40-70 |
| 10% Tween 80 pH 4.5-5.0** | 50-100 | 25-50 | <10* | >100 | >50 | >50 |
| 10% Tween 80 pH 5.5-6.0** | 25-30 | 25-35 | <10* | >100 | 50-100 | 50-100 |
| 2% Tween 80 pH 5** | <50 | NA | NA | >100 | NA | NA |
| 2% Tween pH 6.4** | <10* | NA | NA | >44 | NA | NA |

*Not soluble at stated concentration, large amount of material not in solution,
NA - Not performed;
**This pH range is the pH range observed of the tested samples Compound 5 has unexpectedly superior solubility characteristics under a number of conditions compared to the other compounds tested. The differences are even more striking at the mildly acidic conditions that are most suitable for human administration (>pH 4). The increased solubility of Compound 5 at these conditions would be advantageous in developing a formulation to be delivered to humans. Additionally, it was observed that the compound of Compound 2 showed a marked decrease in solubility above pH 4, which is in the pH range where most aqueous parenteral drugs are preferred to be formulated (pH 4-7) to reduce tissue irritation. Compound 5 showed no such significant change in solubility with pH. The increased solubility was surprising and unexpected since there was no change in the polarity or charge distribution between these compounds.

An additional critical aspect in drug delivery is retention of solubility with time (physical stability), especially under refrigerated conditions. It was surprising and unexpected that under refrigerated conditions, Compound 5 had no changes in solution solubility or solution characteristics, whereas other compounds tested often had quite significant changes in physical form and often solidified into a gel (Table 9). Unexpectedly, clear differences in physical stability were observed between Compound 5 and other compounds with only minor changes in sequence (e.g. Compounds 7 and 8). The combination of unexpected solubility of greater than 100 mg/mL in mildly acidic conditions and lack of significant changes in solution character after refrigeration, are unexpected and advantageous for a pharmaceutical product.

TABLE 9

Appearance of Compound Solutions in Table 8 After Incubation at 2-8° C. for 1 week.

| Solubility Conditions | Compound # | | | | | |
|---|---|---|---|---|---|---|
| | 2 | 9 | 10 | 5 | 7 | 8 |
| | Solution Appearance after 7 days Storage at 2-8° C. | | | | | |
| Water | Gel | Gel | Hazy, syrupy | Clear Liquid | Hazy, syrupy | Clear syrupy |
| 50% propylene glycol, pH 2.7 | Gel | Gel | Gel | Clear Liquid | Gel | Gel |
| 30% PEG 400 | Gel | Syrupy w/ppct. | Hazy Liquid | Clear Liquid | Syrupy | Gel |
| 50% EtOH/water | Gel | Gel | Gel | Clear Liquid | Gel | Gel |
| 10% Tween 80 pH 2.3-2.8 | Gel | Clear Liquid | Gel | Clear Liquid | Gel | Clear Liquid |

TABLE 9-continued

Appearance of Compound Solutions in Table 8 After Incubation at 2-8° C. for 1 week.

| Solubility Conditions | Compound # | | | | | |
|---|---|---|---|---|---|---|
| | 2 | 9 | 10 | 5 | 7 | 8 |
| | Solution Appearance after 7 days Storage at 2-8° C. | | | | | |
| 10% Tween 80 pH 4.5-5.0 | Gel | Clear Liquid | Gel | Clear Liquid | Clear Liquid | Gel |
| 10% Tween 80 pH 5.5-6.0 | Liquid w/ppct. | Liquid w/ppct. | Milky Liquid w/ppct. | Clear Liquid | Clear Liquid | Gel |
| 2% Tween 80 pH 5 | Gel | NA | NA | Clear Liquid | NA | NA |
| 2% Tween pH 6.4 | Gel | NA | NA | Clear Liquid | NA | NA |

Without being bound by any particularly theory, it is theorized that beta homoproline (bhPro) at position 5 gives rise to a more flexible peptide backbone with greater potential to generate a turn structure. This has been observed previously (Malesevic et al. Spectroscopic detection of pseudo-turns in homodetic cyclic penta- and hexapeptides comprising beta-homoproline. *International Journal of Peptide Research and Therapeutics.* 2006; 12(2):165-177). Replacing the bhPro at position 5 with beta alanine (compound 10), allowing for more flexibility and rotational freedom in the peptide backbone, does not improve solubility characteristics. In fact solubility characteristics were unexpectedly reduced. The compounds with bhPro or beta alanine that permit greater flexibility in the peptide backbone all have worse solubility characteristics than compounds 5, 7, and 8 which have a rigid spacer in the backbone. These data suggest that reducing the conformational flexibility at position 5 may account for some of the unexpected solubility characteristics. Other replacements at this position have been described, which suggests other ways to restrict the conformational space at this position. (Burgess, *Proc Natl. Acad. Sci. USA* 91, 2649-2653).

Example 5

Pharmacokinetic and Pharmacodynamic Characterization

Figure 6:
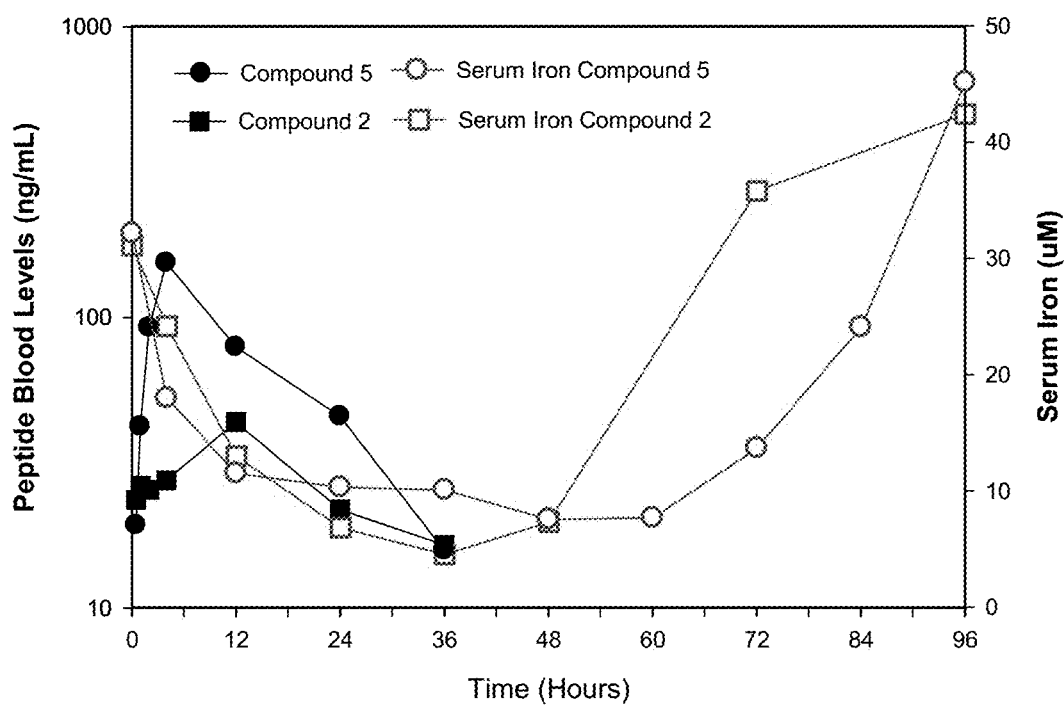
FIG. 6 illustrates a comparison of Compound 2 and Compound 5 blood levels and corresponding resultant serum iron levels after subcutaneous administration in rat (7.5 mg/kg).
Figure 7:
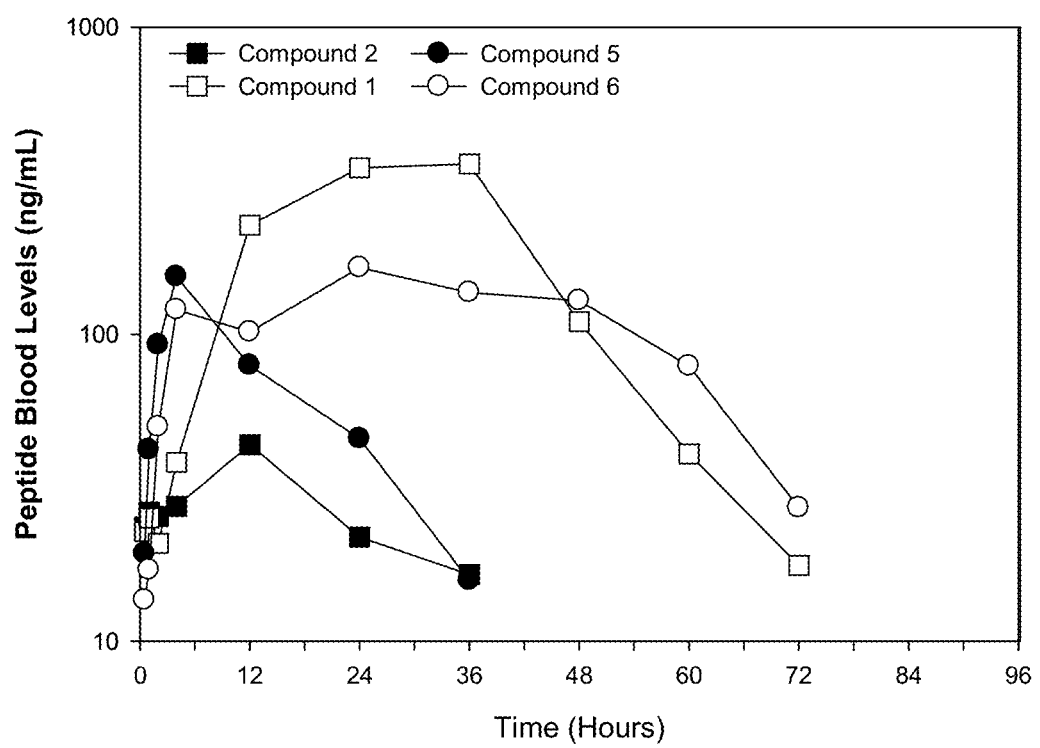
FIG. 7 illustrates blood levels of Compound 2 and Compound 5 and respective metabolites, Compound 1 and Compound 6, after subcutaneous administration in rat, of either Compound 2 or Compound 5 (7.5 mg/kg).
Figure 8:
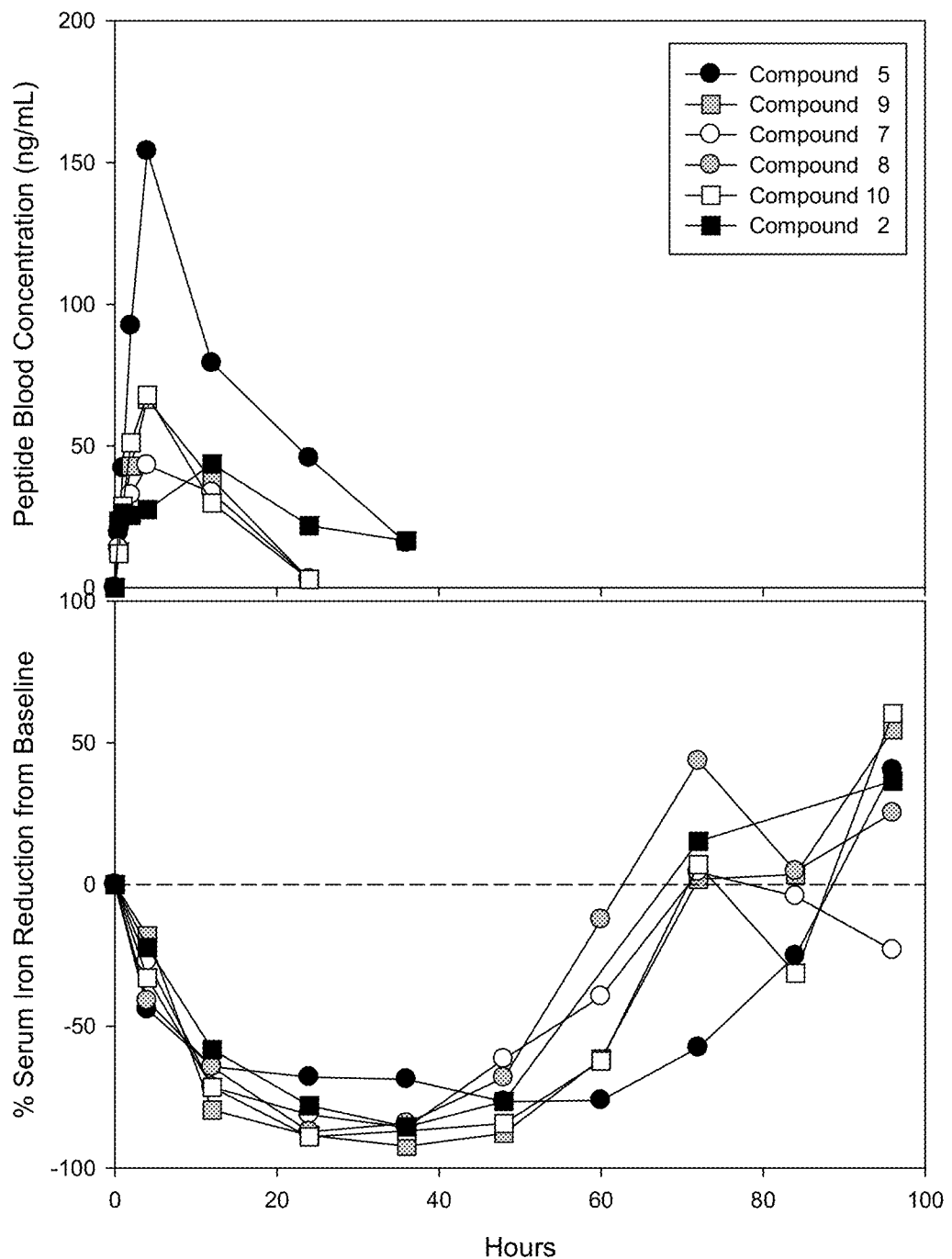
FIG. 8. Top Panel illustrates the blood levels of indicated compounds after subcutaneous administration in rat (7.5 mg/kg); Bottom Panel illustrates the corresponding reduction in serum iron (% reduction from baseline) after administration of the indicated compounds.

Compounds 2 and 5 have the same sequence except at position 5 where Compound 2 has a bhPro residue whereas Compound 5 has a nipecotic acid residue (Npc). These residues are rather dissimilar in their properties and effect on the structure of the peptide backbone. Compound 5 was formulated as described in Example 3 and administered subcutaneously to rats at a dose of 7.5 mg/kg. The compound with Npc at position 5 retained significant hepcidin activity, which is illustrated in FIG. 6. Comparable reduction in serum iron is observed when these compounds are administered subcutaneously, with Compound 5 having an unexpected and surprisingly longer effect. FIG. 7 shows the levels of the corresponding metabolite of each compound after injection, indicating that both compounds are converted into their corresponding active metabolite, compounds with a free sulfhydryl group on the cysteine, with similar exposure levels of these metabolite species.

Example 6

Changes in Position 5 Effect on In Vivo Serum Iron Reduction

Compounds 2, 5, 7, 8, 9, and 10 were formulated as described in Example 3 and delivered subcutaneously to rats at a compound dose of 7.5 mg/kg. Compound 5 had surprisingly higher blood levels relative to the other compounds. However, all tested compounds had comparable effect at reducing serum iron. It is surprising that compounds 5, 7 and 8 which have a more hindered rotationally restricted space, by inclusion of Nipecotic acid (and also L- and D-forms), have comparable activity. This finding is in contrast to what has been previously taught by in vitro structure/activity relationship studies where substitution of an alanine residue at this position leads to about a 20% loss in activity. (Clark R J et al., *Chem Biol.* 2011 Mar. 25; 18(3):336-43). Understanding the structure/activity relationships of the iron regulatory peptide hepcidin, which is hereby incorporated by reference in its entirety.

All of the above U.S. patents, U.S. patent application publications, U.S. patent applications, foreign patents, foreign patent applications and non-patent publications, including CAS numbers, referred to in this specification and/or listed in the Application Data Sheet are incorporated herein by reference, in their entirety.

What is claimed is:

1. A compound, or pharmaceutically acceptable salt thereof, of formula

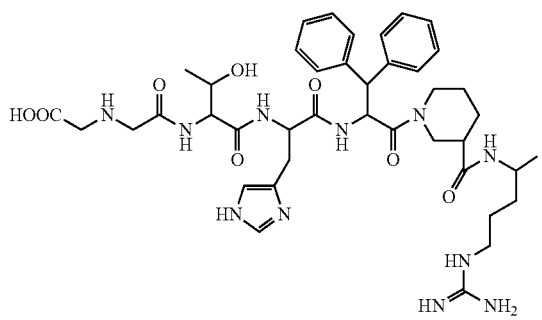

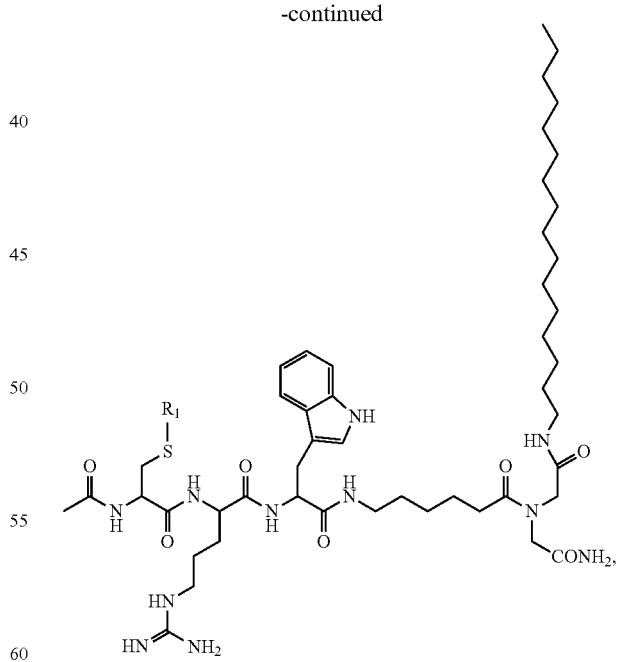

wherein $R_1$ is —S—$CH_3$ or H.

2. The compound, or pharmaceutically acceptable salt thereof, of claim 1, wherein $R_1$ is —S—$CH_3$.

3. The compound, or pharmaceutically acceptable salt thereof, of claim 1, wherein $R_1$ is H.

4. A pharmaceutical composition comprising a compound, or pharmaceutically acceptable salt thereof, of formula

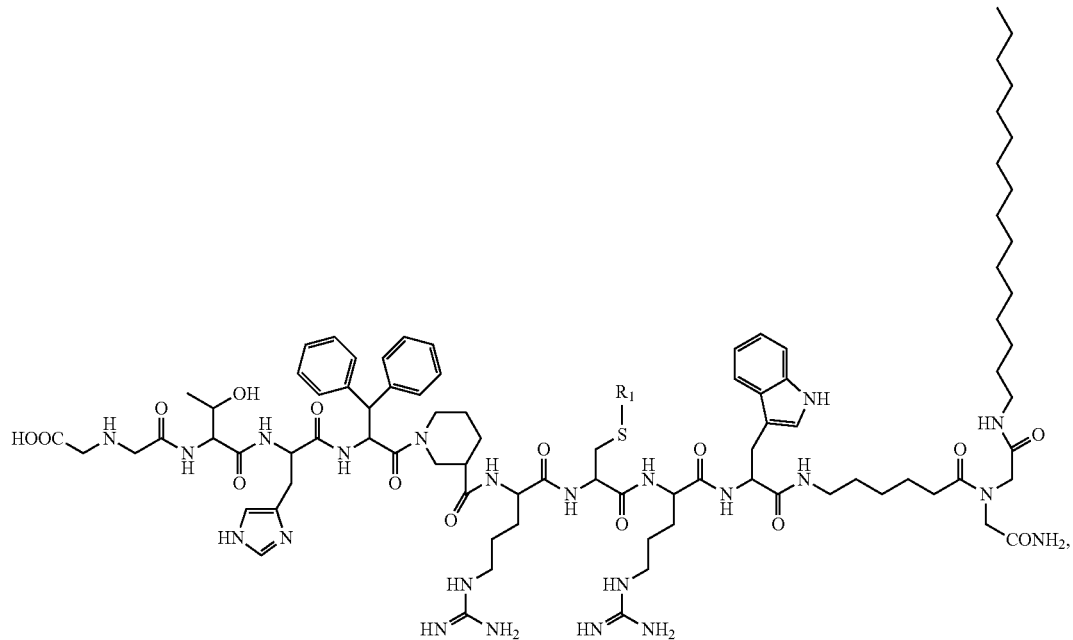

wherein $R_1$ is —S—CH$_3$ or H.

5. The pharmaceutical composition of claim 4 further comprising a pharmaceutically acceptable excipient.

6. The pharmaceutical composition of claim 4, wherein $R_1$ is —S—CH$_3$.

7. The pharmaceutical composition of claim 4, wherein $R_1$ is H.

8. A method of reducing serum iron concentration in a subject in need thereof comprising administering to the subject a pharmaceutical composition comprising a compound, or pharmaceutically acceptable thereof, of formula

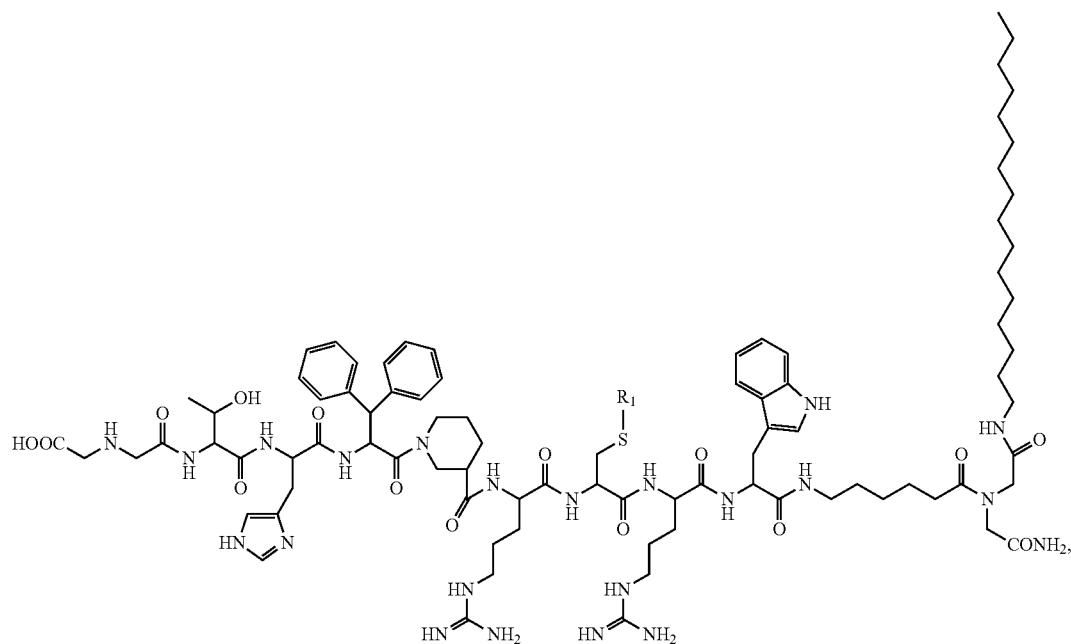

wherein $R_1$ is —S—CH$_3$ or H.

9. The method of claim 8, wherein $R_1$ is —S—$CH_3$.

10. The method of claim 8, wherein $R_1$ is H.

11. A method of therapeutic treatment for beta thalassemia comprising administering to a subject in need thereof a pharmaceutical composition comprising a compound, or pharmaceutically acceptable salt thereof, of formula

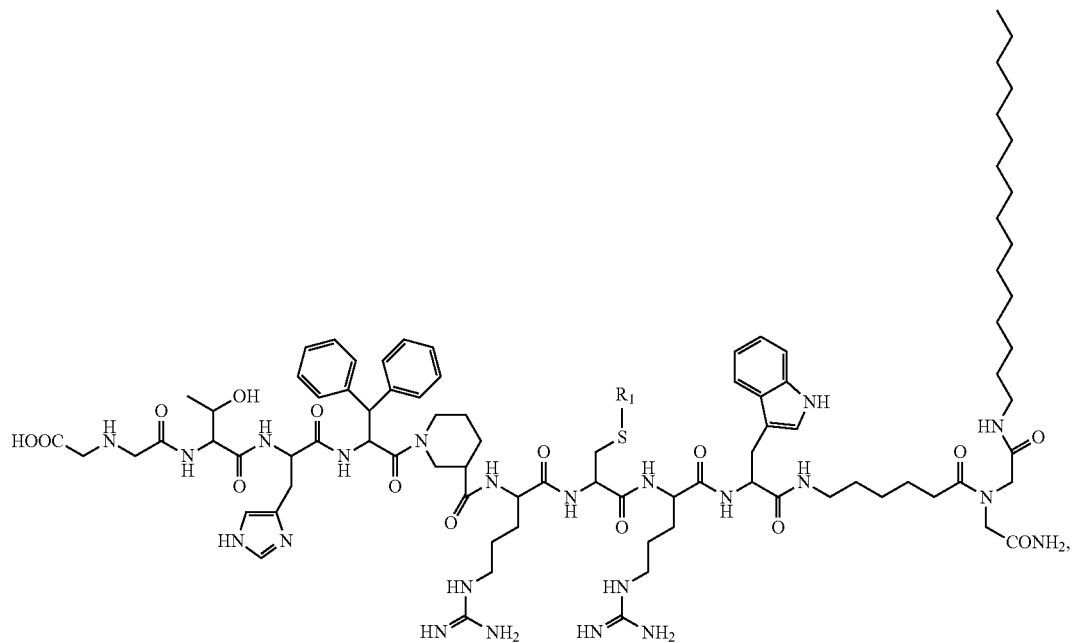

wherein $R_1$ is —S—$CH_3$ or H.

12. The method of claim 11, wherein $R_1$ is —S—$CH_3$.

13. The method of claim 11, wherein $R_1$ is H.

* * * * *